United States Patent
Giblin et al.

(10) Patent No.: US 9,309,254 B2
(45) Date of Patent: Apr. 12, 2016

(54) PYRIMIDINYL-DIAZOSPIRO COMPOUNDS

(71) Applicant: CONVERGENCE PHARMACEUTICALS LIMITED, London (GB)

(72) Inventors: Gerard M. P. Giblin, Cambridge (GB); David T. MacPherson, Cambridge (GB); David R. Witty, Cambridge (GB); Steven J. Stanway, Cambridge (GB)

(73) Assignee: Convergence Pharmaceuticals Limited, London (GB)

( * ) Notice: Subject to any disclaimer, the term of this patent is extended or adjusted under 35 U.S.C. 154(b) by 0 days.

(21) Appl. No.: 14/403,480

(22) PCT Filed: May 22, 2013

(86) PCT No.: PCT/GB2013/051336
§ 371 (c)(1),
(2) Date: Nov. 24, 2014

(87) PCT Pub. No.: WO2013/175206
PCT Pub. Date: Nov. 28, 2013

(65) Prior Publication Data
US 2015/0119404 A1 Apr. 30, 2015

Related U.S. Application Data

(60) Provisional application No. 61/773,710, filed on Mar. 6, 2013, provisional application No. 61/650,325, filed on May 22, 2012.

(30) Foreign Application Priority Data

May 22, 2012 (GB) .................................. 1209015.5

(51) Int. Cl.
*C07D 471/10* (2006.01)
*C07D 487/10* (2006.01)
*A61K 31/407* (2006.01)
*A61K 31/438* (2006.01)

(52) U.S. Cl.
CPC ............ *C07D 487/10* (2013.01); *A61K 31/407* (2013.01); *A61K 31/438* (2013.01); *C07D 471/10* (2013.01)

(58) Field of Classification Search
CPC .. C07D 471/10; C07D 487/10; A61K 31/407; A61K 31/438
USPC ........................... 544/242, 333, 335; 514/256
See application file for complete search history.

(56) References Cited

U.S. PATENT DOCUMENTS

| | | | |
|---|---|---|---|
| 7,655,693 B2 | 2/2010 | Alvaro et al. |
| 7,803,833 B2 | 9/2010 | Alvaro et al. |
| 7,855,218 B2 | 12/2010 | Alvaro et al. |
| 8,093,268 B2 | 1/2012 | Alvaro et al. |
| 8,143,306 B2 | 3/2012 | Alvaro et al. |
| 8,153,623 B2 | 4/2012 | Alvaro et al. |
| 8,153,681 B2 | 4/2012 | Alvaro et al. |
| 8,759,542 B2 | 6/2014 | Zajac |
| 2008/0293753 A1 | 11/2008 | Alvaro et al. |
| 2009/0318530 A1 | 12/2009 | Alvaro et al. |
| 2009/0326032 A1 | 12/2009 | Alvaro et al. |
| 2010/0105688 A1 | 4/2010 | Alvaro et al. |
| 2010/0130583 A1 | 5/2010 | Alvaro et al. |
| 2014/0350040 A1 | 11/2014 | Witty et al. |
| 2015/0166551 A1 | 6/2015 | Giblin et al. |
| 2015/0225400 A1 | 8/2015 | Witty et al. |

FOREIGN PATENT DOCUMENTS

| | | |
|---|---|---|
| WO | 2007042239 A1 | 4/2007 |
| WO | 2007042240 A1 | 4/2007 |
| WO | 2007042250 A1 | 4/2007 |
| WO | 2008090114 A1 | 7/2008 |
| WO | 2008122546 A1 | 10/2008 |
| WO | 2013093496 A1 | 6/2013 |
| WO | 2013093497 A1 | 6/2013 |
| WO | 2013179049 A1 | 12/2013 |

OTHER PUBLICATIONS

Eijkelkamp et al., Neurological perspectives on voltage-gated sodium channels, Brain: A Journal of Neurology, 135, pp. 2585-2612 (2012).*

Large, et al. "The Efficacy of Sodium Channel Blockers to Prevent Phencyclidine-Induced Cognitive Dysfunction in the Rat: Potential for Novel Treatments for Schizophrenia." J Pharmacol Exp Ther. Jul. 2011;338(1):100-113. doi: 10.1124/jpet.110.178475. Epub Apr. 12, 2011; PMID: 21487071 http://www.ncbi.nlm.nih.gov/pubmed/21487071.

Large et al. "The Relationship Between Sodium Channel Inhibition and Anticonvulsant Activity in a Model of Generalised Seizure in the Rat." Epilepsy Res. Jul. 2009;85(1):96-106. doi: 10.1016/j.eplepsyres2009.02.018. Epub Mar. 28, 2009. PMID: 19329281 http://www.ncbi.nlm.nih.gov/pubmed/19329281.

* cited by examiner

*Primary Examiner* — Deepak Rao
(74) *Attorney, Agent, or Firm* — Honigman Miller Schwartz and Cohn LLP; Kathryn D. Doyle; Jonathan P. O'Brien

(57) ABSTRACT

The invention relates to spiro derivatives, to the use of said derivatives in treating diseases and conditions mediated by modulation of voltage-gated sodium channels, to compositions containing said derivatives and processes for their preparation.

24 Claims, No Drawings

PYRIMIDINYL-DIAZOSPIRO COMPOUNDS

FIELD OF THE INVENTION

The invention relates to spiro derivatives, to the use of said derivatives in treating diseases and conditions mediated by modulation of voltage-gated sodium channels, to compositions containing said derivatives and processes for their preparation.

BACKGROUND OF THE INVENTION

Voltage-gated sodium channels are responsible for the initial phase of the action potential, which is a wave of electrical depolarisation usually initiated at the soma of the neuron and propagated along the axon to the terminals. At the terminals, the action potential triggers the influx of calcium and the release of neurotransmitter. Drugs, such as lidocaine, that block voltage-gated sodium channels are used as local anaesthetics. Other sodium channel blockers, such as lamotrigine and carbamazepine are used to treat epilepsy. In the latter case, partial inhibition of voltage-gated sodium channels reduces neuronal excitability and reduces seizure propagation. In the case of local anaesthetics, regional block of sodium channels on sensory neurons prevents the conduction of painful stimuli. A key feature of these drugs is their state-dependent mechanism of action. The drugs are thought to stabilise an inactivated conformation of the channel that is adopted rapidly after the channel opens. This inactivated state provides a refractory period before the channel returns to its resting (closed) state ready to be reactivated. As a result, state-dependent sodium channel blockers inhibit the firing of neurons at high frequency, for example in response to painful stimuli, and will help to prevent repetitive firing during periods of prolonged neuronal depolarisation that might occur, for example, during a seizure. Action potentials triggered at lower frequencies, for example in the heart, will not be significantly affected by these drugs, although the safety margin differs in each case, since at high enough concentrations each of these drugs is capable of blocking the resting or open states of the channels.

The voltage-gated sodium channel family is made up of 9 subtypes, four of which are found in the brain, NaV1.1, 1.2, 1.3 and 1.6. Of the other subtypes, NaV1.4 is found only in skeletal muscle, NaV1.5 is specific to cardiac muscle, and NaV1.7, 1.8, and 1.9 are found predominantly in sensory neurons. The hypothesised binding site for state-dependent sodium channel blockers is the local anaesthetic (LA) binding site in the inner vestibule of the pore on transmembrane S6 of domain IV. Critical residues are located in a highly conserved region among the different subtypes, thus presenting a challenge for the design of new subtype selective drugs. Drugs such as lidocaine, lamotrigine and carbamazepine do not distinguish between the subtypes. However, selectivity can be achieved, and can be further enhanced functionally, as a result of the different frequencies at which the channels operate.

Drugs that block voltage-gated sodium channels in a state-dependent manner are also used in the treatment of bipolar disorder, either to reduce symptoms of mania or depression, or as mood stabilisers to prevent the emergence of mood episodes. Clinical and preclinical evidence also suggests that state-dependent sodium channel blockers may help to reduce the symptoms of schizophrenia. For example, lamotrigine has been shown to reduce symptoms of psychosis induced by ketamine in healthy human volunteers, and furthermore, studies in patients suggest that the drug can augment the antipsychotic efficacy of some atypical antipsychotic drugs, such as clozapine or olanzapine. It is hypothesised that efficacy in these psychiatric disorders may result in part from a reduction of excessive glutamate release. The reduction in glutamate release is thought to be a consequence of sodium channel inhibition in key brain areas, such as the frontal cortex. However, interaction with voltage-gated calcium channels may also contribute to the efficacy of these drugs.

WO 2007/042240 (Glaxo Group Limited) describes a series of quaternary alpha-aminocarboxamide derivatives as modulators of voltage-gated sodium channels.

The object of the invention is to identify alternative compounds which modulate voltage-gated sodium channels.

SUMMARY OF THE INVENTION

According to a first aspect, the invention provides a compound of formula (I) or a pharmaceutically acceptable salt or solvate thereof:

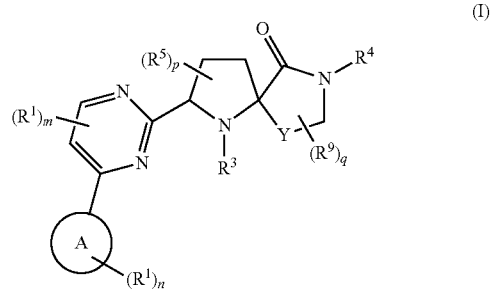

wherein:
Ring A represents a phenyl ring, a 5- or 6-membered aromatic heterocyclic ring or a 5- to 12-membered aromatic or non-aromatic bicyclic heterocyclic group;
n represents an integer selected from 0 to 4;
each $R^1$ independently represents $C_{1-6}$ alkyl, $C_{2-6}$ alkenyl, $C_{2-6}$ alkynyl, -Z—$C_{3-6}$cycloalkyl, halogen, halo$C_{1-6}$ alkyl, $C_{1-6}$ alkoxy, halo$C_{1-6}$ alkoxy, -Z-phenyl, -Z-Het, —CN, —CONR$^6$R$^7$, —NR$^6$R$^7$, -Z—$C_{1-3}$ alkyl, wherein said Het group represents a 5- or 6-membered aromatic heterocyclic ring or a 4- to 7-membered non-aromatic heterocyclic ring, wherein said phenyl or Het group of $R^1$ may be optionally substituted by one or more (e.g. 1, 2 or 3) $R^8$ groups and wherein n represents an integer greater than 1, said $R^1$ groups represent no more than one -Z-phenyl or one -Z-Het group;
Z represents a bond or a linker selected from —O—, —CH$_2$—, —CH$_2$—O— or —O—CH$_2$—;
$R^6$ and $R^7$ independently represent hydrogen or $C_{1-6}$ alkyl or $R^6$ and $R^7$ together with the nitrogen atom to which they are attached join to form a 4- to 7-membered nitrogen containing non-aromatic heterocyclic ring;
$R^8$ represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —CN or —NR$^6$R$^7$;
m represents an integer selected from 0 to 2;
each $R^2$ independently represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —CN or —NR$^7$R$^8$;
$R^3$ represents hydrogen or $C_{1-6}$ alkyl;
$R^4$ represents hydrogen or $C_{1-6}$ alkyl;
p represents an integer from 0 to 3;
each $R^5$ independently represents $C_{1-3}$ alkyl or fluoro;
Y represents —CH$_2$— or —(CH$_2$)$_2$—;
q represents an integer selected from 0 to 2; and
$R^9$ represents $C_{1-3}$ alkyl.

DETAILED DESCRIPTION OF THE INVENTION

According to one particular aspect of the invention, there is provided a compound of formula (I) or a pharmaceutically acceptable salt or solvate thereof:

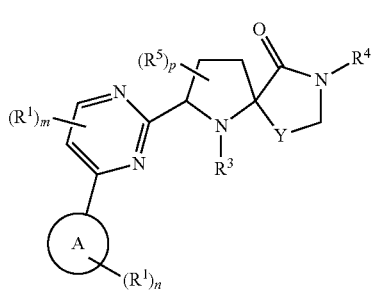

(I)

wherein:
Ring A represents a phenyl ring, a 5- or 6-membered aromatic heterocyclic ring or a 5- to 12-membered aromatic or non-aromatic bicyclic heterocyclic group;
n represents an integer selected from 0 to 4;
each $R^1$ independently represents $C_{1-6}$ alkyl, $C_{2-6}$ alkenyl, $C_{2-6}$ alkynyl, -Z—$C_{3-6}$cycloalkyl, halogen, halo$C_{1-6}$ alkyl, $C_{1-6}$ alkoxy, halo$C_{1-6}$ alkoxy, -Z-phenyl, -Z-Het, —CN, —CONR$^6$R$^7$, —NR$^6$R$^7$, -Z—$C_{1-3}$ alkyl, wherein said Het group represents a 5- or 6-membered aromatic heterocyclic ring or a 4- to 7-membered non-aromatic heterocyclic ring, wherein said phenyl or Het group of $R^1$ may be optionally substituted by one or more (e.g. 1, 2 or 3) $R^8$ groups and wherein n represents an integer greater than 1, said $R^1$ groups represent no more than one -Z-phenyl or one -Z-Het group;
Z represents a bond or a linker selected from —O—, —CH$_2$—, —CH$_2$—O— or O—CH$_2$—;
$R^6$ and $R^7$ independently represent hydrogen or $C_{1-6}$ alkyl or $R^6$ and $R^7$ together with the nitrogen atom to which they are attached join to form a 4- to 7-membered nitrogen containing non-aromatic heterocyclic ring;
$R^8$ represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —CN or —NR$^6$R$^7$;
m represents an integer selected from 0 to 2;
each $R^2$ independently represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —CN or —NR$^7$R$^8$;
$R^3$ represents hydrogen or $C_{1-6}$ alkyl;
$R^4$ represents hydrogen or $C_{1-6}$ alkyl;
each $R^5$ independently represents $C_{1-3}$ alkyl or fluoro;
Y represents —CH$_2$— or —(CH$_2$)$_2$—; and
p represents an integer from 0 to 3.

The term 'halo' or 'halogen' as used herein refers to fluorine, chlorine, bromine or iodine.

The term '$C_{1-3}$alkyl' as used herein as a group or part of a group refers to a linear or branched saturated hydrocarbon group containing from 1 to 3 carbon atoms. The term '$C_{1-6}$ alkyl' as used herein as a group or part of a group refers to a linear or branched saturated hydrocarbon group containing from 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term '$C_{2-6}$alkenyl' as used herein as a group or part of a group refers to a linear or branched hydrocarbon group containing from 2 to 6 carbon atoms and containing a carbon carbon double bond.

The term '$C_{2-6}$alkynyl' as used herein as a group or part of a group refers to a linear or branched hydrocarbon group having from 2 to 6 carbon atoms and containing a carbon carbon triple bond.

The term '$C_{1-6}$alkoxy' as used herein as a group or part of a group refers to an —O—$C_{1-6}$alkyl group wherein $C_{1-6}$alkyl is as defined herein. Examples of such groups include methoxy, ethoxy, propoxy, butoxy, and the like.

The term 'halo$C_{1-6}$alkyl' as used herein as a group or part of a group refers to a $C_{1-6}$alkyl group as defined herein wherein one or more than one hydrogen atom is replaced with a halogen. The term 'halo$C_{1-6}$alkyl' therefore includes monohalo$C_{1-6}$alkyl and also polyhalo$C_{1-6}$ alkyl. There may be one, two, three or more hydrogen atoms replaced with a halogen, so the halo$C_{1-6}$alkyl may have one, two, three or more halogens. Examples of such groups include fluoroethyl, fluoromethyl, trifluoromethyl or trifluoroethyl and the like.

The term 'halo$C_{1-6}$alkoxy' as used herein as a group or part of a group refers to a O—$C_{1-6}$ alkyl group as defined herein wherein one or more than one hydrogen atom is replaced with a halogen. The term 'halo$C_{1-6}$alkoxy' therefore includes monohalo$C_{1-6}$alkoxy, and also polyhalo$C_{1-6}$alkoxy. There may be one, two, three or more hydrogen atoms replaced with a halogen, so the halo$C_{1-6}$alkoxy may have one, two, three or more halogens. Examples of such groups include fluoroethyloxy, difluoromethoxy or trifluoromethoxy and the like.

The term 5- or 6-membered aromatic heterocyclic ring means a heterocyclyl group containing one or more carbon atoms, one or more hydrogen atoms and one or more heteroatoms such as nitrogen, oxygen and sulfur; the carbon and heteroatoms being interconnected to form a ring. Examples of five membered aromatic heterocyclic groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups. Examples of six membered aromatic heterocyclic groups include but are not limited to pyridine, pyrazine, pyridazine, pyrimidine and triazine.

The term 4- or 7-membered non-aromatic heterocyclic ring means a heterocyclyl group containing one or more carbon atoms, one or more hydrogen atoms and one or more heteroatoms such as nitrogen, oxygen and sulfur; the carbon and heteroatoms being interconnected to form a ring. The term "non-aromatic" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C═C, C≡C or N═C bond. The term "saturated" or "fully saturated" refers to rings where there are no multiple bonds between ring atoms. Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

The term 4- to 7-membered nitrogen containing non-aromatic heterocyclic ring means a non-aromatic heterocyclyl ring as defined herein wherein the ring must contain at least one ring nitrogen atom. Particular examples of nitrogen-containing non-aromatic heterocyclyl groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

Particular examples of 5- to 12-membered bicyclic heterocyclic groups typically comprise groups containing a five membered ring fused to another five membered ring and include but are not limited to imidazothiazole (e.g. imidazo[2,1-b]thiazole) and imidazoimidazole (e.g. imidazo[1,2-a]imidazole).

Particular examples of 5- to 12-membered bicyclic heterocyclic groups typically comprise groups containing a six membered ring fused to a five membered ring and include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of 5- to 12-membered bicyclic heterocyclic groups typically comprise groups containing two fused six membered rings and include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Particular examples of 5- to 12-membered bicyclic heterocyclic groups typically comprise groups containing an aromatic ring and a non-aromatic ring and include, tetrahydroisoquinoline, tetrahydroquinoline, dihydrobenzthiophene, dihydrobenzfuran, 2,3-dihydrobenzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine, and indoline groups.

For the avoidance of doubt, unless otherwise indicated, the term "substituted" means substituted by one or more defined groups. In the case where groups may be selected from a number of alternative groups, the selected groups may be the same or different.

For the avoidance of doubt, the term "independently" means that where more than one substituent is selected from a number of possible substituents, those substituents may be the same or different.

In one embodiment, Ring A represents a phenyl ring, a 5- or 6-membered aromatic heterocyclic ring (such as thiophenyl) or a 5- to 12-membered aromatic or non-aromatic bicyclic heterocyclic group (such as indolyl or benzodioxolyl). In a further embodiment, Ring A represents a phenyl ring.

In one embodiment, n represents an integer selected from 0 to 3. In a further embodiment, n represents an integer selected from 1 to 2. In one embodiment, n represents 1. In an alternative embodiment, n represents 2.

In one embodiment, $R^1$ independently represents $C_{1-6}$ alkyl (such as methyl, ethyl or isopropyl), halogen (such as fluorine or chlorine), halo$C_{1-6}$ alkyl (such as $CF_3$), $C_{1-6}$ alkoxy (such as —O-methyl, —O-ethyl, —O-propyl, —O-butyl, —O—CH(Me)$_2$ or —O—CH$_2$—CH(Me)$_2$), halo$C_{1-6}$ alkoxy (such as —O—CF$_3$, —OCHF$_2$ or —CH$_2$—O—CF$_3$), -Z-aryl (such as —O-phenyl, —O—CH$_2$-phenyl or —CH$_2$—O-phenyl), —CN, —CONR$^6$R$^7$ (such as CONH$_2$) or —NR$^6$R$^7$ (such as —N(Me)$_2$), wherein said phenyl groups are optionally substituted by one or more (e.g. 1, 2 or 3) $R^8$ groups such as halogen (e.g. fluorine) or halo$C_{1-6}$ alkoxy (e.g. —O—CF$_3$).

In a further embodiment, $R^1$ independently represents $C_{1-6}$ alkyl (such as methyl), halogen (such as fluorine or chlorine), halo$C_{1-6}$ alkyl (such as $CF_3$), $C_{1-6}$ alkoxy (such as —O-methyl, —O-ethyl or —O—CH(Me)$_2$), halo$C_{1-6}$ alkoxy (such as —O—CF$_3$ or —OCHF$_2$), —CN or —CONR$^6$R$^7$ (such as CONH$_2$).

In a yet further embodiment, $R^1$ independently represents halogen (such as fluorine or chlorine), halo$C_{1-6}$ alkyl (such as $CF_3$), $C_{1-6}$ alkoxy (such as —O-methyl, —O-ethyl or —O—CH(Me)$_2$) or halo$C_{1-6}$ alkoxy (such as —O—CF$_3$ or —OCHF$_2$).

In a yet further embodiment, $R^1$ independently represents halogen (such as fluorine), halo$C_{1-6}$ alkyl (such as $CF_3$), $C_{1-6}$ alkoxy (such as —O-ethyl) or halo$C_{1-6}$ alkoxy (such as —O—CF$_3$).

In a yet further embodiment, $R^1$ independently represents halo$C_{1-6}$ alkyl (such as $CF_3$).

In one embodiment, Z represents —O—, —CH$_2$—O— or —O—CH$_2$—.

In one embodiment, $R^6$ and $R^7$ independently represent hydrogen or $C_{1-6}$ alkyl. In a further embodiment, $R^6$ and $R^7$ independently represent hydrogen or methyl. In yet a further embodiment, $R^6$ and $R^7$ both represent hydrogen.

In one embodiment, $R^8$ represents halogen (e.g. fluorine or chlorine) or halo$C_{1-6}$ alkoxy (e.g. —O—CF$_3$).

In one embodiment, m represents an integer selected from 0 to 1. In one embodiment, m represents 1. In an alternative embodiment, m represents 0.

In one embodiment, $R^2$ independently represents $C_{1-6}$ alkyl, halogen, halo$C_{1-6}$ alkyl, $C_{1-6}$ alkoxy or halo$C_{1-6}$ alkoxy. In a further embodiment, $R^2$ independently represents $C_{1-6}$ alkyl (such as methyl), halogen (such as fluorine) or $C_{1-6}$ alkoxy (such as —OC(Me)$_3$). In a further embodiment, $R^2$ independently represents $C_{1-6}$ alkyl (such as methyl).

In one embodiment, $R^3$ represents hydrogen or methyl. In a further embodiment, $R^3$ represents hydrogen.

In one embodiment, $R^4$ represents hydrogen, methyl or ethyl. In a further embodiment, $R^4$ represents hydrogen or methyl.

When present, $R^5$ independently represents $C_{1-3}$ alkyl (such as methyl) or fluoro. In a further embodiment, $R^5$ represents methyl or fluoro. In a yet further embodiment, $R^5$ represents methyl. In an alternative embodiment, $R^5$ represents fluoro. In one embodiment, p represents 0 to 2. In a further embodiment, p represents 0. In an alternative embodiment, p represents 2. For the avoidance of doubt it should be stated that $R^5$ may be present at any position on either of the spiro rings.

In one embodiment, Y represents a —CH$_2$— group. In an alternative embodiment, Y represents a —(CH$_2$)$_2$— group.

In one embodiment, q represents 0 or 1. In a further embodiment, q represents 0. In an alternative embodiment, q represents 2.

In one embodiment, $R^9$ represents methyl.

According to a further aspect, the invention provides a compound of formula (I)$^a$ or a pharmaceutically acceptable salt or solvate thereof:

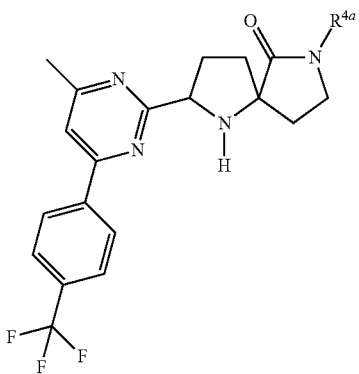

(I)$^a$ wherein R$^{4a}$ represents hydrogen or methyl. In one embodiment, the compound of formula (I)$^a$ is a compound selected from Example 7 and Examples 39 to 42. In a further embodiment, the compound of formula (I)$^a$ is a compound selected from Example 7, the free base of Example 7 and Examples 7a and 7b.

According to a further aspect, the invention provides a compound of formula (I)$^b$ or a pharmaceutically acceptable salt or solvate thereof:

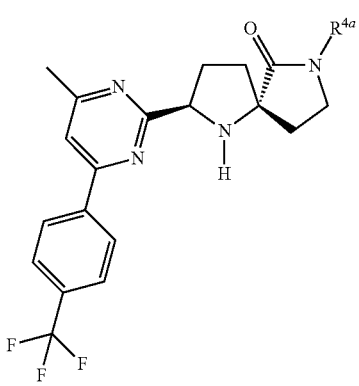

(I)$^b$ wherein R$^{4a}$ represents hydrogen or methyl. In one embodiment, the compound of formula (I)$^b$ is a compound selected from Example 7 and Example 39. In a further embodiment, the compound of formula (I)$^b$ is a compound selected from Example 7, the free base of Example 7 and Examples 7a and 7b.

In one embodiment, the compound of formula (I) is:
(2R,5S)-7-Methyl-2-[4-[4-(trifluoromethyl)phenyl]pyrimidin-2-yl]-1,7-diazaspiro[4.4]nonan-6-one hydrochloride (E1);
(2S,5S)-7-Methyl-2-[4-[4-(trifluoromethyl)phenyl]pyrimidin-2-yl]-1,7-diazaspiro[4.4]nonan-6-one hydrochloride (E2);
(2S,5R)-7-Methyl-2-[4-[4-(trifluoromethyl)phenyl]pyrimidin-2-yl]-1,7-diazaspiro[4.4]nonan-6-one hydrochloride (E3);
(2R,5R)-7-Methyl-2-[4-[4-(trifluoromethyl)-phenyl]-pyrimidin-2-yl]-1,7-diazaspiro[4.4]nonan-6-one hydrochloride (E4);
(2S,5R)-7-Methyl-2-[4-methyl-6-[4-(trifluoromethyl)phenyl]pyrimidin-2-yl]-1,7-diazaspiro[4.4]nonan-6-one hydrochloride (E5);
(2R,5R)-7-Methyl-2-[4-methyl-6-[4-(trifluoromethyl)phenyl]pyrimidin-2-yl]-1,7-diazaspiro[4.4]nonan-6-one hydrochloride (E6);
(2R,5S)-7-Methyl-2-[4-methyl-6-[4-(trifluoromethyl)-phenyl]pyrimidin-2-yl]-1,7-diazaspiro[4.4]nonan-6-one hydrochloride (E7);
(2R,5S)-7-Methyl-2-[4-methyl-6-[4-(trifluoromethyl)-phenyl]pyrimidin-2-yl]-1,7-diazaspiro[4.4]nonan-6-one sulfuric acid salt (E7a)
(2R,5S)-7-Methyl-2-[4-methyl-6-[4-(trifluoromethyl)-phenyl]pyrimidin-2-yl]-1,7-diazaspiro[4.4]nonan-6-one sulfuric acid salt hydrate (E7b)
(2S,5R)-2-[4-(5-Ethoxy-2-fluoro-phenyl)-6-methyl-pyrimidin-2-yl]-7-methyl-1,7-diazaspiro[4.4]nonan-6-one hydrochloride (E8);
(2R,5R)-2-[4-(5-Ethoxy-2-fluoro-phenyl)-6-methyl-pyrimidin-2-yl]-7-methyl-1,7-diazaspiro[4.4]nonan-6-one hydrochloride (E9);
(2R,5S)-2-[4-(5-Ethoxy-2-fluoro-phenyl)-6-methyl-pyrimidin-2-yl]-7-methyl-1,7-diazaspiro[4.4]nonan-6-one hydrochloride (E10);
(2S,5S)-2-[4-(5-Ethoxy-2-fluoro-phenyl)-6-methyl-pyrimidin-2-yl]-7-methyl-1,7-diazaspiro[4.4]nonan-6-one hydrochloride (E11);
(2R,6S)-2-[4-(5-Ethoxy-2-fluoro-phenyl)-6-methyl-pyrimidin-2-yl]-1,8-diazaspiro[4.5]decan-7-one hydrochloride (E12);
(2S,6S)-2-[4-(5-Ethoxy-2-fluoro-phenyl)-6-methyl-pyrimidin-2-yl]-1,8-diazaspiro[4.5]decan-7-one hydrochloride (E13);
(2R,5R)-2-[4-(5-Ethoxy-2-fluoro-phenyl)pyrimidin-2-yl]-7-methyl-1,7-diazaspiro[4.4]nonan-6-one hydrochloride (E14);
(2S,5R)-2-[4-(5-Ethoxy-2-fluoro-phenyl)pyrimidin-2-yl]-7-methyl-1,7-diazaspiro[4.4]nonan-6-one hydrochloride (E15);
(2S,5S)-2-[4-(5-Ethoxy-2-fluoro-phenyl)pyrimidin-2-yl]-7-methyl-1,7-diazaspiro[4.4]nonan-6-one hydrochloride (E16);
(2R,5S)-2-[4-(5-Ethoxy-2-fluoro-phenyl)pyrimidin-2-yl]-7-methyl-1,7-diazaspiro[4.4]nonan-6-one hydrochloride (E17);
(2R,5S)-7-Methyl-2-[4-[3-(trifluoromethoxy)phenyl]pyrimidin-2-yl]-1,7-diazaspiro[4.4]nonan-6-one hydrochloride (E18);
(2S,5S)-7-Methyl-2-[4-[3-(trifluoromethoxy)phenyl]pyrimidin-2-yl]-1,7-diazaspiro[4.4]nonan-6-one hydrochloride (E19);
(2S,5R)-7-Methyl-2-[4-[3-(trifluoromethoxy)phenyl]pyrimidin-2-yl]-1,7-diazaspiro[4.4]nonan-6-one hydrochloride (E20);
(2R,5R)-7-Methyl-2-[4-[3-(trifluoromethoxy)phenyl]pyrimidin-2-yl]-1,7-diazaspiro[4.4]nonan-6-one hydrochloride (E21);
(2S,5S)-7-Methyl-2-[4-methyl-6-[4-(trifluoromethyl)-phenyl]pyrimidin-2-yl]-1,7-diazaspiro[4.4]nonan-6-one hydrochloride (E22);
(2R,5R)-2-[4-(4-Isopropoxyphenyl)pyrimidin-2-yl]-7-methyl-1,7-diazaspiro[4.4]nonan-6-one hydrochloride (E23);
(2S,5R)-2-[4-(4-Isopropoxyphenyl)pyrimidin-2-yl]-7-methyl-1,7-diazaspiro[4.4]nonan-6-one hydrochloride (E24);
(2S,5S)-2-[4-(4-Isopropoxyphenyl)pyrimidin-2-yl]-7-methyl-1,7-diazaspiro[4.4]nonan-6-one hydrochloride (E25);

(2S,5S)-2-[4-(4-Isopropoxyphenyl)pyrimidin-2-yl]-7-methyl-1,7-diazaspiro[4.4]nonan-6-one hydrochloride (E26);
(2R,5S)-7-Methyl-2-[4-methyl-6-[4-(trifluoromethoxy)phenyl]pyrimidin-2-yl]-1,7-diazaspiro[4.4]nonan-6-one hydrochloride (E27);
(2S,5S)-7-Methyl-2-[4-methyl-6-[4-(trifluoromethoxy)phenyl]pyrimidin-2-yl]-1,7-diazaspiro[4.4]nonan-6-one hydrochloride (E28);
(2S,5R)-7-Methyl-2-[4-methyl-6-[4-(trifluoromethoxy)phenyl]pyrimidin-2-yl]-1,7-diazaspiro[4.4]nonan-6-one hydrochloride (E29);
(2R,5R)-7-Methyl-2-[4-methyl-6-[4-(trifluoromethoxy)phenyl]pyrimidin-2-yl]-1,7-diazaspiro[4.4]nonan-6-one hydrochloride (E30);
(2S,5S)-2-[4-[2-Fluoro-5-(trifluoromethoxy)phenyl]-6-methyl-pyrimidin-2-yl]-7-methyl-1,7-diazaspiro[4.4]nonan-6-one hydrochloride (E31);
(2R,5S)-2-[4-[2-Fluoro-5-(trifluoromethoxy)phenyl]-6-methyl-pyrimidin-2-yl]-7-methyl-1,7-diazaspiro[4.4]nonan-6-one hydrochloride (E32);
(2R,5R)-2-[4-[2-Fluoro-5-(trifluoromethoxy)phenyl]-6-methyl-pyrimidin-2-yl]-7-methyl-1,7-diazaspiro[4.4]nonan-6-one hydrochloride (E33);
(2S,5R)-2-[4-[2-Fluoro-5-(trifluoromethoxy)phenyl]-6-methyl-pyrimidin-2-yl]-7-methyl-1,7-diazaspiro[4.4]nonan-6-one hydrochloride (E34);
(2R,5S)-7-Methyl-2-[4-methyl-6-[3-(trifluoromethoxy)phenyl]pyrimidin-2-yl]-1,7-diazaspiro[4.4]nonan-6-one hydrochloride (E35);
(2S,5S)-7-Methyl-2-[4-methyl-6-[3-(trifluoromethoxy)phenyl]pyrimidin-2-yl]-1,7-diazaspiro[4.4]nonan-6-one hydrochloride (E36);
(2R,6R)-2-[4-(5-Ethoxy-2-fluoro-phenyl)-6-methyl-pyrimidin-2-yl]-1,8-diazaspiro[4.5]decan-7-one hydrochloride (E37);
(2S,6R)-2-[4-(5-Ethoxy-2-fluoro-phenyl)-6-methyl-pyrimidin-2-yl]-1,8-diazaspiro[4.5]decan-7-one hydrochloride (E38);
(2R,5S)-2-[4-Methyl-6-[4-(trifluoromethyl)phenyl]pyrimidin-2-yl]-1,7-diazaspiro[4.4]-nonan-6-one hydrochloride (E39);
(2S,5R)-2-[4-Methyl-6-[4-(trifluoromethyl)phenyl]-pyrimidin-2-yl]-1,7-diazaspiro[4.4]nonan-6-one hydrochloride (E40);
(2S,5S)-2-[4-Methyl-6-[4(trifluoromethyl)-phenyl]-pyrimidin-2-yl]-1,7-diazaspiro[4.4]nonan-6-one hydrochloride (E41);
(2R,5R)-2-[4-Methyl-6-[4-(trifluoromethyl)phenyl]pyrimidin-2-yl]-1,7-diazaspiro[4.4]nonan-6-one hydrochloride (E42);
(2R,5S)-8,8-Dimethyl-2-[4-methyl-6-[4-(trifluoromethyl)phenyl]pyrimidin-2-yl]-1,7-diazaspiro[4.4]nonan-6-one hydrochloride (E43);
(2S,5S)-8,8-Dimethyl-2-[4-methyl-6-[4-(trifluoromethyl)phenyl]pyrimidin-2-yl]-1,7-diazaspiro[4.4]nonan-6-one hydrochloride (E44);
(2S,5R)-8,8-Dimethyl-2-[4-methyl-6-[4-(trifluoromethyl)phenyl]pyrimidin-2-yl]-1,7-diazaspiro[4.4]nonan-6-one hydrochloride (E45); and
(2R,5R)-8,8-Dimethyl-2-[4-methyl-6-[4-(trifluoromethyl)phenyl]pyrimidin-2-yl]-1,7-diazaspiro[4.4]nonan-6-one hydrochloride (E46) or an alternative pharmaceutically acceptable salt, solvate or free base preparation thereof.

In a further embodiment, the compound of formula (I) is a compound of E1-E22 or an alternative pharmaceutically acceptable salt, solvate or free base preparation thereof.

In a further embodiment, the compound of formula (I) is (2R,5S)-7-methyl-2-[4-methyl-6-[4-(trifluoromethyl)-phenyl]pyrimidin-2-yl]-1,7-diazaspiro[4.4]nonan-6-one or a pharmaceutically acceptable salt or solvate thereof, such as (2R,5S)-7-methyl-2-[4-methyl-6-[4-(trifluoromethyl)-phenyl]pyrimidin-2-yl]-1,7-diazaspiro[4.4]nonan-6-one hydrochloride (E7). In an alternative embodiment, the compound of formula (I) is (2R,5S)-7-methyl-2-[4-methyl-6-[4-(trifluoromethyl)-phenyl]pyrimidin-2-yl]-1,7-diazaspiro[4.4]nonan-6-one mono sulfuric acid salt (E7a) or (2R,5S)-7-methyl-2-[4-methyl-6-[4-(trifluoromethyl)-phenyl]pyrimidin-2-yl]-1,7-diazaspiro[4.4]nonan-6-one monosulfuric acid salt hydrate (E7b). In an alternative embodiment, the compound of formula (I) is the free base of E7, i.e. (2R,5S)-7-methyl-2-[4-methyl-6-[4-(trifluoromethyl)-phenyl]pyrimidin-2-yl]-1,7-diazaspiro[4.4]nonan-6-one.

In one embodiment, the compound of formula (I) is other than 7-methyl-2-[4-methyl-6-[4-(trifluoromethyl)-phenyl]pyrimidin-2-yl]-1,7-diazaspiro[4.4]nonan-6-one or a pharmaceutically acceptable salt or solvate thereof, such as:
(2R,5S)-7-methyl-2-[4-methyl-6-[4-(trifluoromethyl)-phenyl]pyrimidin-2-yl]-1,7-diazaspiro[4.4]nonan-6-one;
(2R,5S)-7-methyl-2-[4-methyl-6-[4-(trifluoromethyl)-phenyl]pyrimidin-2-yl]-1,7-diazaspiro[4.4]nonan-6-one hydrochloride (E7);
(2R,5S)-7-methyl-2-[4-methyl-6-[4-(trifluoromethyl)-phenyl]pyrimidin-2-yl]-1,7-diazaspiro[4.4]nonan-6-one mono sulfuric acid salt (E7a);
(2R,5S)-7-methyl-2-[4-methyl-6-[4-(trifluoromethyl)-phenyl]pyrimidin-2-yl]-1,7-diazaspiro[4.4]nonan-6-one monosulfuric acid salt hydrate (E7b); and
(2R,5S)-7-methyl-2-[4-methyl-6-[4-(trifluoromethyl)-phenyl]pyrimidin-2-yl]-1,7-diazaspiro[4.4]nonan-6-one.

Thus, in a further embodiment, the compound of formula (I) is a compound of E1-E6 and E8-E46. In a further embodiment, the compound of formula (I) is a compound of E1-E6 or E8-E22.

A reference to a compound of the formula (I) and subgroups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, prodrugs, isotopes and protected forms thereof as defined in any aspect of the invention (except intermediate compounds in chemical processes) are referred to as "compounds of the invention".

Many compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as dichloromethane, 1,4-dioxane, ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-aminosalicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention. In one embodiment, the pharmaceutically acceptable solvates of the compounds of the invention include the hydrate thereof.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

In one embodiment, the invention provides compounds of formula (Ia)

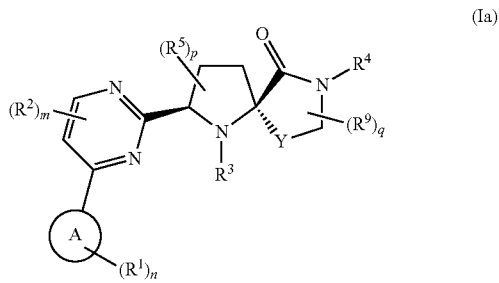

(Ia)

wherein $R^1$, $R^2$, $R^3$, $R^4$, $R^5$, $R^9$, m, n, p, q, Y and A are as defined herein for compounds of formula (I). In one embodiment of the compound of formula (Ia), q represents 0.

In one embodiment, the invention provides compounds of formula (Ib)

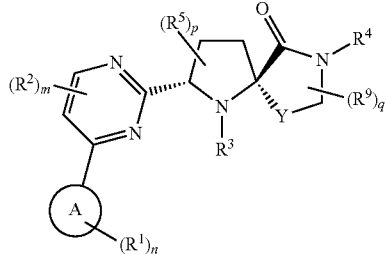

(Ib)

wherein $R^1$, $R^2$, $R^3$, $R^4$, $R^5$, $R^9$, m, n, p, q, A and Y are as defined herein for compounds of formula (I). In one embodiment of the compound of formula (Ib), q represents 0.

In one embodiment, the invention provides compounds of formula (Ic)

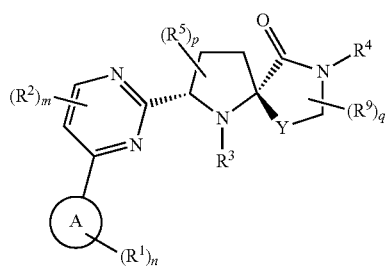

(Ic)

wherein $R^1$, $R^2$, $R^3$, $R^4$, $R^5$, $R^9$, m, n, p, q, A and Y are as defined herein for compounds of formula (I). In one embodiment of the compound of formula (Ic), q represents 0.

In one embodiment, the invention provides compounds of formula (Id)

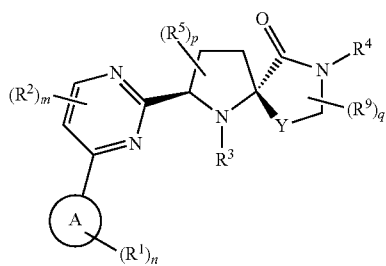

(Id)

wherein $R^1$, $R^2$, $R^3$, $R^4$, $R^5$, $R^9$, m, n, p, q, A and Y are as defined herein for compounds of formula (I). In one embodiment of the compound of formula (Id), q represents 0.

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2H$ (D) and $^3H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3H$ (T), and carbon-14, i.e. $^{14}C$, are particularly useful for this purpose in view of their ease of incorporation and ready means of detection.

Substitution with heavier isotopes such as deuterium, i.e. $^2H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

According to a further aspect of the invention there is provided a process for preparing a compound of formula (I) as herein defined which comprises:

(a) forming a compound of formula (I) wherein p represents 0 and $R^3$ represents hydrogen by performing a ring closure reaction of a compound of formula (II) followed by reduction of the resulting imine (IIA):

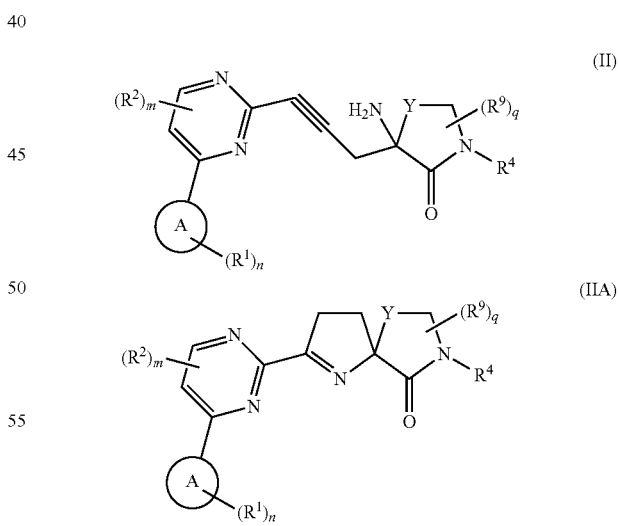

(II)

(IIA)

or a protected derivative thereof, wherein A, $R^1$, $R^2$, $R^4$, $R^9$, n, m, q and Y are as defined herein for compounds of formula (I);
(b) deprotection of a protected derivative of a compound of formula (I);
(c) interconversion of a compound of formula (I) or protected derivative thereof to a further compound of formula (I) or protected derivative thereof; and (d) optional formation of a pharmaceutically acceptable salt of a compound of formula (I).

Process (a) typically comprises treating the compound of formula (II) with a suitable reagent, such as silver trifluoromethanesulfonate (AgOTf), with stirring at a suitable temperature, such as 40° C., for a suitable time period, such as 3 to 7 days, followed by reduction of the resulting imine (IIA) by a hydride reducing agent such as sodium triacetoxyborohydride in a solvent system such as aqueous hydrochloride acid and dichloromethane, or by using borane or a modified borane such as tertiarybutylamine:borane complex, or hydrogenation over a suitable catalyst such as platinum.

Compounds of formula (II) wherein Y represents —$CH_2$— may be prepared in accordance with Scheme 1:

wherein A, $R^1$, $R^2$, $R^4$, $R^9$, n, m and q are as defined herein for compounds of formula (I), $L^1$ represents a suitable leaving group, such as a halogen atom (i.e. bromine) and $L^2$ represents a suitable leaving group, such as a halogen atom (i.e. iodine) and $P^1$ represents a suitable protecting group, such as Boc.

Step (i) typically comprises reacting a compound of formula (III) with a compound of formula (IV) in the presence of a suitable solvent, such as dichloroethane (DCE).

Step (ii) typically comprises reacting a compound of formula (V) with a compound of formula (VI) in the presence of a suitable base such as potassium tert-butoxide and a suitable solvent, such as tetrahydrofuran (THF).

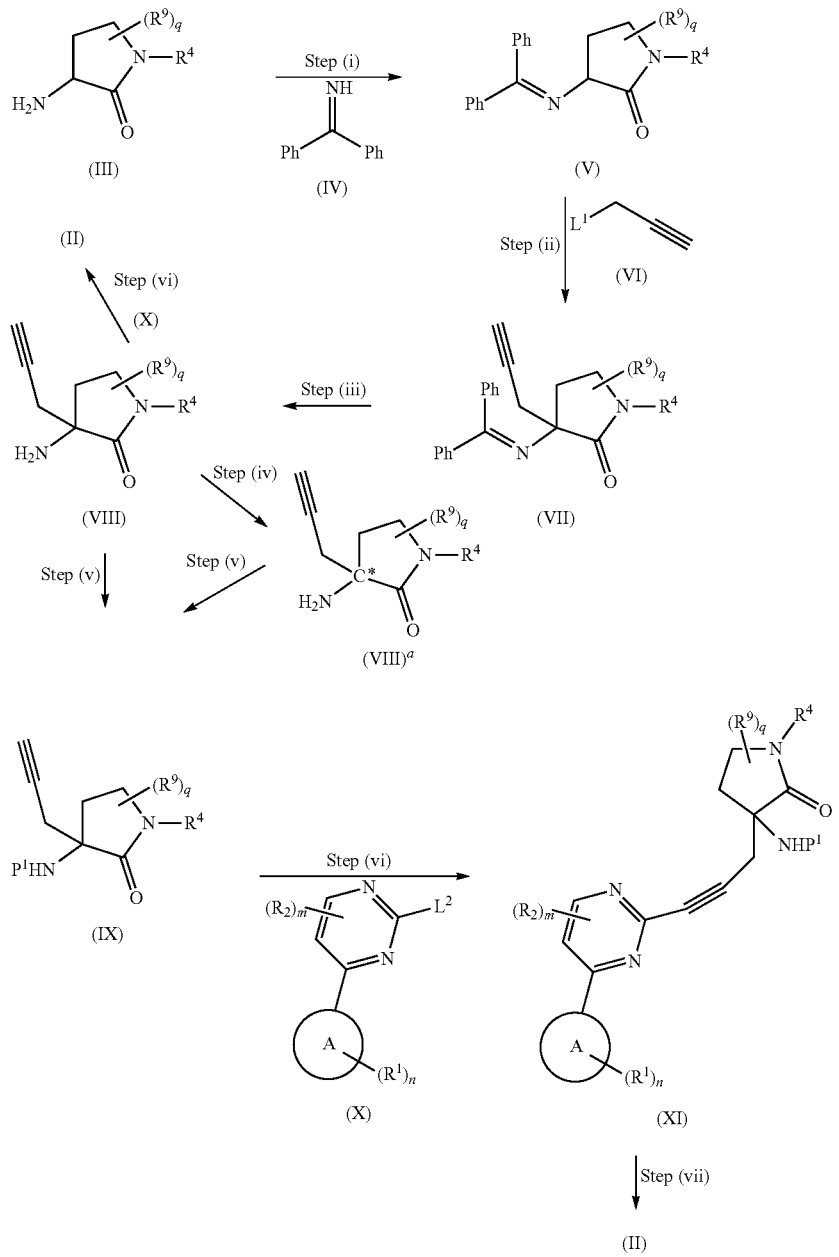

Scheme 1

Step (iii) typically comprises deprotecting a compound of formula (VII) with a suitable acidic reagent, such as citric acid.

Step (iv) comprises a chiral resolution in which one chiral diastereomeric salt form of (VIII) is crystallised and separated from a more soluble epimer, for example by fractional crystallisation of (VIII) with a chiral acid such as mandelic acid or 2-(6-methoxy-2-naphthyl)propanoic acid in a suitable solvent such as THF, acetonitrile or isopropyl alcohol. The chiral form (VIII)$^a$ may be liberated by treating the salt with a base, such as a resin-bound base, in a suitable solvent such as methanol.

Step (v) typically comprises treating a compound of formula (VIII) with a suitable amine protecting reagent, such as $Boc_2O$, in the presence of a suitable solvent, such as dichloromethane (DCM).

Step (vi) typically comprises reacting a terminal alkyne of formula (IX) or (VIII) with a compound of formula (X) in the presence of a suitable reagent, such as copper iodide, a suitable catalyst, such as $PdCl_2(Ph_3P)_2$, a suitable base, such as diethylamine ($Et_2NH$) or diisopropylamine and a suitable solvent, such as tetrahydrofuran, or tertiarybutyl methyl ether.

Step (vii) typically comprises deprotecting a compound of formula (XI) with a suitable acidic reagent, such as trifluoroacetic acid (TFA) in the presence of a suitable solvent, such as dichloromethane (DCM) or alternatively by using sulphuric acid in a solvent such as 1,4-dioxane.

Compounds of formula (II) wherein Y represents —$(CH_2)_2$— and $R^4$ represents hydrogen may be prepared in accordance with Scheme 2:

Scheme 2

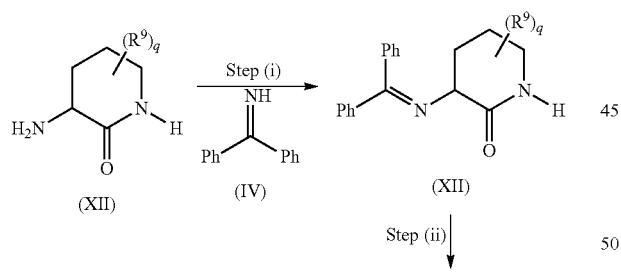

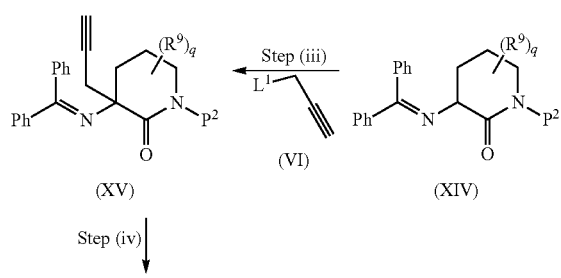

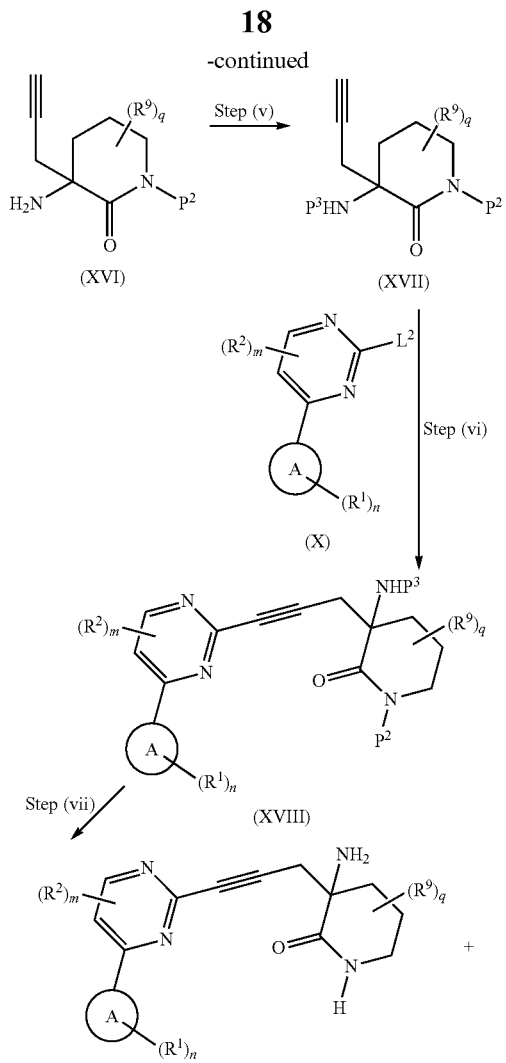

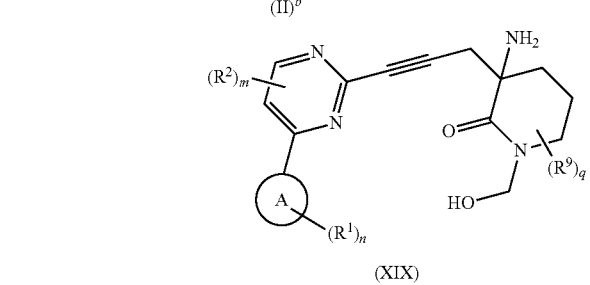

wherein A, $R^1$, $R^2$, $R^9$, n, m and q are as defined herein for compounds of formula (I), $L^1$ represents a suitable leaving group, such as a halogen atom (i.e. bromine) and $L^2$ represents a suitable leaving group, such as a halogen atom (i.e. iodine), $P^2$ represents a suitable protecting group, such as SEM and $P^3$ represents a suitable protecting group, such as $Boc_2O$.

Step (i) typically comprises reacting a compound of formula (XII) with a compound of formula (IV) in the presence of a suitable solvent, such as dichloroethane (DCE).

Step (ii) typically comprises introducing a protecting group by reacting a compound of formula (XIII) with, for example SEM-Cl, in the presence of potassium tert-butoxide and a suitable solvent, such as tetrahydrofuran (THF).

Step (iii) typically comprises reacting a compound of formula (XIV) with a compound of formula (VI) in the presence of potassium tert-butoxide and a suitable solvent, such as tetrahydrofuran (THF).

Step (iv) typically comprises deprotecting a compound of formula (XV) with a suitable acidic reagent, such as citric acid.

Step (v) typically comprises treating a compound of formula (XVI) with a suitable protecting group, such as Boc₂O, in the presence of a suitable solvent, such as dichloromethane (DCM).

Step (vi) typically comprises reacting a compound of formula (XVII) with a compound of formula (X) in the presence of a suitable reagent, such as copper iodide, a suitable catalyst, such as PdCl₂(Ph₃P)₂, a suitable base, such as diethylamine (Et₂NH) and a suitable solvent, such as tetrahydrofuran or tertiary butyl methyl ether.

Step (vii) typically comprises deprotecting a compound of formula (XVIII) with a suitable acidic reagent, such as trifluoroacetic acid (TFA) in the presence of a suitable solvent, such as dichloromethane (DCM). The hydroxymethyl compound (XIX) is only formed when P² is a SEM group.

Compounds of formula (X) may be prepared in accordance with Scheme 3:

Scheme 3

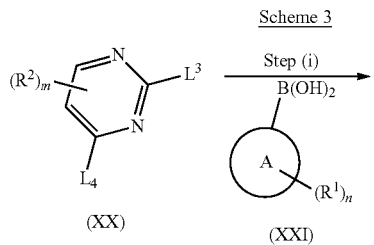

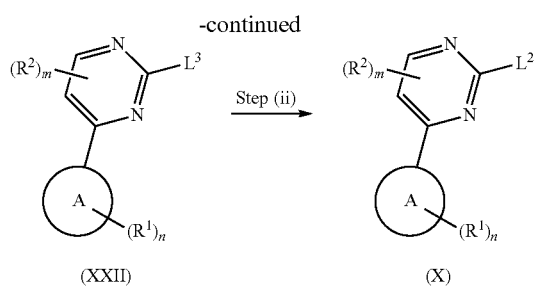

wherein R¹, R², m, n and A are as defined herein for compounds of formula (I), L² represents a suitable leaving group, such as a halogen atom (i.e. iodine), L³ represents a suitable leaving group, such as a halogen atom (i.e. chlorine) and L⁴ represents a suitable leaving group, such as a halogen atom (i.e. chlorine).

Step (i) typically comprises reacting a compound of formula (XX) with a compound of formula (XXI) in the presence of a suitable reagent, such as sodium carbonate, a suitable catalyst, such as PdCl₂(Ph₃P)₂, and a suitable solvent, such as dimethoxyethane/water.

When L³ represents chlorine and L² represents iodine, step (ii) typically comprises reacting a compound of formula (MI) with hydrogen iodide.

Compounds of formula (IIA)ᵃ may also be prepared in accordance with Scheme 4:

Scheme 4

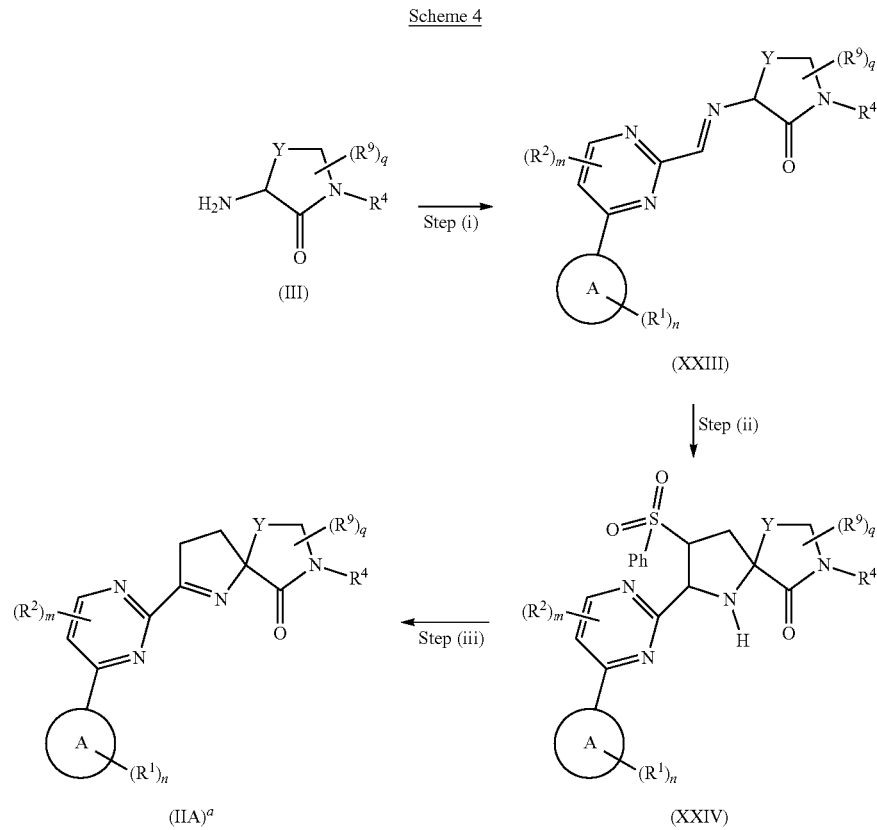

wherein $R^1$, $R^2$, $R^4$, $R^9$, m, n, q, A and Y are as defined herein for compounds of formula (I).

Step (i) typically comprises condensation of a compound of formula (III) with a carboxyaldehyde compound, including for example a compound of formula (XXVII) (the preparation of which is described below in Scheme 5), in the presence of a dehydrating agent such as magnesium sulfate, or molecular sieves, in a solvent such as dichloromethane.

Step (ii) typically comprises a [3+2] cycloaddition reaction with phenyl vinyl sulfone catalysed by a transition metal salt such as a silver or copper salt, in the presence of a base and optionally a chiral phosphine ligand.

Step (iii) typically comprises elimination of the phenyl vinyl sulfone typically with a strong base such as potassium tert-butoxide.

Carboxaldehyde compounds of formula (XXVII) suitable for reacting with compounds of formula (III) in Scheme 4, may be commercially available but may also be prepared according to Scheme 5:

Scheme 5

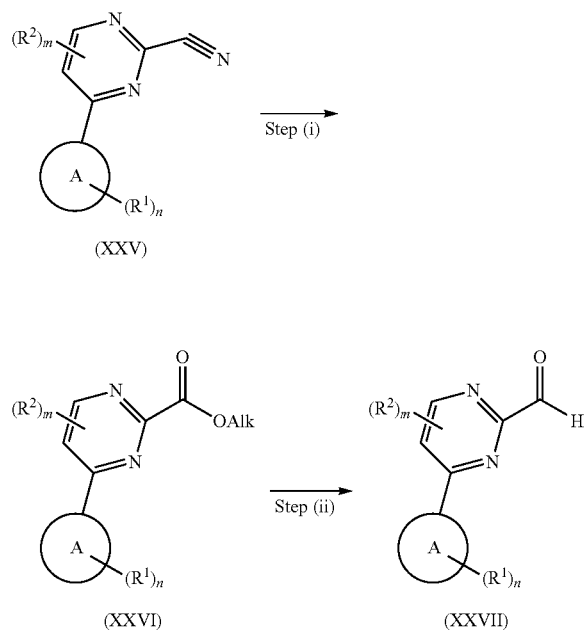

wherein A, $R^1$, $R^2$, n and m are as defined herein for compounds of formula (I)

Step (i) typically comprises an acid catalysed (for example hydrochloride acid) alkoholysis of a 2-cyanopyrimdine with, for example, methanol.

Step (ii) comprises a reduction to an aldehyde using a hindered hydride reducing agent, for example diisobutyl aluminium hydride, in a suitable solvent such as toluene or dichloromethane.

Compounds of formula (III) may be prepared in accordance with known methodology or, for example compounds of formula (III)$^a$ wherein Y represents —$CH_2$—, $R^4$ represents H, q represents 2 and $R^9$ represents methyl may be prepared in accordance with Scheme 6:

Scheme 6

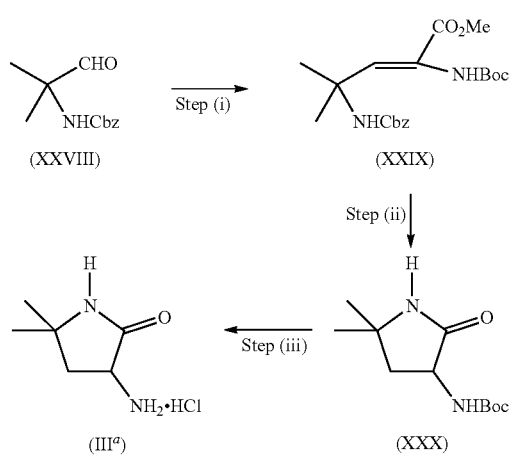

Step (i) typically comprises a Horner-Wadsworth-Emmons condensation reaction of an optionally substituted carbamate protected alpha aminocarboxaldehyde with an optionally substituted methyl 2-(tert-butoxycarbonylamino) phosphorylacetate in the presence of a catalyst such as 1,8-diazabicyclo(5.4.0)undec-7-ene.

Step (ii) typically comprises a hydrogenation such as continuous hydrogenation reaction performed in a flow system, for example by using a hydrogenation reactor such as an H-cube, and passing a flow of substrate through a packed catalyst cartridge.

Step (iii) typically comprises deprotection of the amine group with a strong acid such as HCl in a solvent such as dioxane. The salt form of (III) may be converted to the free base form by treatment with a base such as triethylamine in the course of a subsequent reaction.

Compounds of formulae (III), (IV), (VI), (XII), (XX), (XXI), (XXV) and (XXVIII) are either known or may be prepared in accordance with known methodology.

It will be appreciated by those skilled in organic synthesis that two or more chemical steps in the schemes above may be run sequentially without isolation of intermediate materials.

A wide range of well known functional group interconversions for process (c) are known by a person skilled in the art for converting a precursor compound to a compound of formula (I) and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described in Scheme 1-6 are followed or preceded by one or more reactions known to the skilled of the art and are performed in an appropriate order to achieve the requisite substitutions on $R^1$, $R^2$, $R^3$ and $R^4$, defined above to afford other compounds of formula (I). Non-limiting examples of such reactions whose conditions can be found in the literature include:

protection of reactive functions,
deprotection of reactive functions,
halogenation,
dehalogenation,
dealkylation, alkylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of esters groups,
Sonogashira arylation of an alkyne
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

One particular interconversion which may be mentioned includes alkylation of compounds of formula (I) wherein $R^4$ represents hydrogen to a compound of formula (I) wherein $R^4$ represents $C_{1-6}$ alkyl. Such an interconversion reaction typically comprises a suitable base such as sodium hydride to deprotonate the amide followed by treatment with an alkylating agent such as methyl iodide in a solvent such as DMF.

One further particular interconversion which may be mentioned includes alkylation of compounds of formula (I) wherein $R^3$ represents hydrogen to a compound of formula (I) wherein $R^3$ represents $C_{1-6}$ alkyl. Such an interconversion reaction typically comprises reductive alkylation with an aldehyde in the presence of a suitable mild hydride donor agent such as sodium triacetoxyborohydride.

It is recognised that the sequence of reactions involving aryl coupling and reduction may be varied. It is also recognised that a wide range of palladium based catalysts are suitable for conducting aryl coupling reactions.

It may also be recognised that isomer separation may occur at any suitable stage in the synthetic sequence. It should be stressed that such chiral separation forms a key aspect of the invention and that such separation may be conducted in accordance with the methodology described herein or may be conducted in accordance with known methodology. For example, a compound of formula (VIII), including the case where $R^4$=H, may be resolved into component enantiomers by resolution to form differentially soluble and separable diastereomeric crystalline salts with a chiral acid such as mandelic acid, 2-methoxy-2-phenylacetic acid, tartaric acid, camphor sulfonic acid or di-p-toluoyltartaric acid, followed by treatment with base to liberate the resolved free base form. It is also recognised that it may be beneficial to temporarily form a protected derivative of an intermediate in the synthesis, for example, a Boc-protected amine, or SEM-protected amide, in order to facilitate chromatographic separation, chiral resolution or to give improved solubility or yields in particular steps.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>0=0) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a t-butyl carbamate (—NHCO—OC(CH$_3$)$_3$, —NH-Boc); a 2-biphenyl-2-propyl carbamate (—NHCO—OC(CH$_3$)$_2$C$_6$H$_4$C$_6$H$_5$, —NH-Boc), as a 9-fluorenylmethyl carbamate (—NH-Fmoc), as a 6-nitroveratryl carbamate (—NH—Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulphonyl)ethyl carbamate (—NH—Psec).

Other protecting groups for amines, such as cyclic amines and heterocyclic N—H groups, include toluenesulphonyl (tosyl) and methanesulphonyl (mesyl) groups, benzyl groups such as a para-methoxybenzyl (PMB) group and tetrahydropyranyl (THP) groups.

As discussed hereinabove, it is believed that compounds of the invention may be useful for the treatment of diseases and conditions mediated by modulation of voltage-gated sodium channels.

In one embodiment, the compounds will be state-dependent sodium channel inhibitors.

In another embodiment, the compounds will be subtype NaV1.7 sodium channel state-dependent inhibitors.

In another embodiment, the compounds will be state-dependent sodium channel inhibitors which have a suitable developability profile on oral administration, for example in terms of exposure (Cmax) and/or bioavailability.

In one embodiment, the compounds will be sodium channel inhibitors.

In another embodiment, the compounds will be subtype NaV1.7 sodium channel inhibitors.

In another embodiment, the compounds will be sodium channel inhibitors which have a suitable developability profile on oral administration, for example in terms of exposure (Cmax) and/or bioavailability.

According to a further aspect of the invention, there is provided compounds of the invention for use as a medicament, preferably a human medicament.

According to a further aspect the invention provides the use of compounds of the invention in the manufacture of a medicament for treating or preventing a disease or condition mediated by modulation of voltage-gated sodium channels.

In one particular embodiment, compounds of the invention may be useful as analgesics. For example they may be useful in the treatment of chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention may be useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention may also be useful in the amelioration of inflammatory disorders, for example in the treatment of skin conditions (e.g. sunburn, burns, eczema, dermatitis, psoriasis); ophthalmic diseases; lung disorders (e.g. asthma, bronchitis, emphysema, allergic rhinitis, non-allergic rhinitis, cough, respiratory distress syndrome, pigeon fancier's disease, farmer's lung, chronic obstructive pulmonary disease, (COPD); gastrointestinal tract disorders (e.g. Crohn's disease, ulcerative colitis, coeliac disease, regional ileitis, irritable bowel syndrome, inflammatory bowel disease, gastroesophageal reflux disease); other conditions with an inflammatory component such as migraine, multiple sclerosis, myocardial ischemia.

In one embodiment, the compounds of the invention are useful in the treatment of neuropathic pain or inflammatory pain as described herein.

Without wishing to be bound by theory, other diseases or conditions that may be mediated by modulation of voltage-gated sodium channels are selected from the list consisting of [the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10)]:

i) Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

ii) Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

iii) Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

iv) Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9);

Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-lnduced Anxiety Disorder Sedative-, Hypnotic-, or Anxiolytic-lnduced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

v) Enhancement of cognition including the treatment of cognition impairment in other diseases such as schizophrenia, bipolar disorder, depression, other psychiatric disorders and psychotic conditions associated with cognitive impairment, e.g. Alzheimer's disease:

vi) Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

vi) Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50):

vii) Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

viii) Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

ix) Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9): and x) Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

xi) Impulse control disorder" including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

In another embodiment, diseases or conditions that may be mediated by modulation of voltage gated sodium channels are depression or mood disorders In another embodiment, diseases or conditions that may be mediated by modulation of voltage gated sodium channels are substance related disorders.

In a further embodiment, diseases or conditions that may be mediated by modulation of voltage gated sodium channels are Bipolar Disorders (including Bipolar I Disorder, Bipolar II Disorder (i.e. Recurrent Major Depressive Episodes with Hypomanic Episodes) (296.89), Cyclothymic Disorder (301.13) or Bipolar Disorder Not Otherwise Specified (296.80)).

In a still further embodiment, diseases or conditions that may be mediated by modulation of voltage gated sodium channels are Nicotine-Related Disorders such as Nicotine Dependence (305.1), Nicotine Withdrawal (292.0) or Nicotine-Related Disorder Not Otherwise Specified (292.9).

Compounds of the invention may also be useful in the treatment and/or prevention of disorders treatable and/or preventable with anti-convulsive agents, such as epilepsy including post-traumatic epilepsy, obsessive compulsive disorders (OCD), sleep disorders (including circadian rhythm disorders, insomnia & narcolepsy), tics (e.g. Giles de la Tourette's syndrome), ataxias, muscular rigidity (spasticity), and temporomandibular joint dysfunction.

Compounds of the invention may also be useful in the treatment of bladder hyperrelexia following bladder inflammation.

Compounds of the invention may also be useful in the treatment of neurodegenerative diseases and neurodegeneration such as dementia, particularly degenerative dementia (including senile dementia, Alzheimer's disease, Pick's disease, Huntington's chorea, Parkinson's disease and Creutzfeldt-Jakob disease, motor neuron disease); The compounds may also be useful for the treatment of amyotrophic lateral sclerosis (ALS) and neuroinflamation.

Compounds of the invention may also be useful in neuroprotection and in the treatment of neurodegeneration following stroke, cardiac arrest, pulmonary bypass, traumatic brain injury, spinal cord injury or the like.

Compounds of the invention may also be useful in the treatment of tinnitus, and as local anaesthetics.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

When used in the treatment or prophylaxis of pain, the compound of formula (I) or a pharmaceutically acceptable salt thereof may be used in combination with other medicaments indicated to be useful in the treatment or prophylaxis of pain of neuropathic origin including neuralgias, neuritis and back pain, and inflammatory pain including osteoarthritis, rheumatoid arthritis, acute inflammatory pain, back pain and migraine. Such therapeutic agents include for example COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO 99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the $\alpha_2\delta$-subunit of voltage gated calcium channels, such as gabapentin, pregabalin and solzira; tricyclic antidepressants such as amitriptyline; neurone stabilising antiepileptic drugs; cholinesterase inhibitors such as galantamine; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; nicotinic acetyl choline (nACh) receptor modulators; glutamate receptor modulators, for example modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at $P2X_3$, $P2X_{2/3}$, $P2X_4$, $P2X_7$ or $P2X_{4/7}$; KCNQ/Kv7 channel openers, such as retigabine; additional COX-2 inhibitors are disclosed in U.S. Pat. No. 5,474,995, U.S. Pat. No. 5,633,272, U.S. Pat. No. 5,466,823, U.S. Pat. No. 6,310,099 and U.S. Pat. No. 6,291,523; and in WO 96/25405, WO 97/38986, WO 98/03484, WO 97/14691, WO 99/12930, WO 00/26216, WO 00/52008, WO 00/38311, WO 01/58881 and WO 02/18374.

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example Iofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyproheptidine; ii) antidepressants; iii) antipsychotics; iv) zinc; and v) premenstrual agents for example pyridoxine and progesterones.

The compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstrual agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donepezil).

The compounds of the invention may be used in combination with the following agents to treat personality disorders: i) antipsychotics; ii) antidepressants; iii) mood stabilisers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and bupropion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, proclorperazine, trifluoperazine, thiothixene, haloperidol, molindone and loxapine); and Atypical Antipsychotics (for example clozapine, olanzapine, risperidone, quetiapine, aripiprazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

It will be appreciated that references herein to "treatment" extend to prophylaxis, prevention of recurrence and suppression or amelioration of symptoms (whether mild, moderate or severe) as well as the treatment of established conditions.

The compound of the invention may be administered as the raw chemical but the active ingredient is preferably presented as a pharmaceutical formulation.

According to a further aspect, the invention provides a pharmaceutical composition comprising a compound of the invention, in association with one or more pharmaceutically acceptable carrier(s), diluents(s) and/or excipient(s). The carrier, diluent and/or excipient must be "acceptable" in the sense of being compatible with the other ingredients of the composition and not deleterious to the recipient thereof.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter-sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, for example from 10-60% by weight, of the active material, depending on the method of administration. Where the compositions comprise dosage units, each unit will for example contain from 5-1000 mg of the active ingredient. The dosage as employed for adult human treatment may range from 10 to 3000 mg per day depending on the route and frequency of administration. For oral administration a typical dose may be in the range of 50 to 1500 mg per day, for example 120 to 1000 mg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The embodiments described for the first aspect similarly apply to these further aspects. The diseases and conditions described above extend, where appropriate, to these further aspects:

i) A compound of the invention for use in treating or preventing a disease or condition mediated by modulation of voltage-gated sodium channels.

ii) A method of treatment or prevention of a disease or condition mediated by modulation of voltage-gated sodium channels in a mammal comprising administering an effective amount of a compound of the invention.

iii) Use of a compound of the invention in the manufacture of a medicament to treat or prevent a disease or condition mediated by modulation of voltage-gated sodium channels.

iv) Use of a compound of the invention to treat or prevent a disease or condition mediated by modulation of voltage-gated sodium channels.

EXAMPLES

The invention is illustrated by the Examples described below.

In the procedures that follow, after each starting material, reference to a Description or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

The absolute configuration of the stereocentres within the spiro fused compounds prepared from achiral starting materials and resolved by use of chiral chromatography have been assigned using a combination of optical rotation and NMR spectroscopy (for determining the relative stereochemistry of adjacent stereocentres) and relating these to chiral intermediates and final compounds which have had their absolute configurations determined by single crystal X-ray crystallography. It will be appreciated that some uncertainty exists relating to the absolute configurations referred to herein which have been based primarily on inferred configurations. It will be apparent to the skilled person that absolute configurations can only be definitively characterised by specific analytical determinations, such as X-ray crystallography.

Compounds are named using ACD/Name PRO 6.02 chemical naming software (Advanced Chemistry Development Inc., Toronto, Ontario, M5H2L3, Canada), or using Lexichem's automatic chemical naming software Version 2.0.1 (OpenEye Scientific Software Inc. Santa Fe, N. Mex., USA).

Proton Magnetic Resonance (NMR) spectra are typically recorded on a Bruker instruments at 300, 400 or 500 MHz. Chemical shifts are reported in ppm (δ) using the residual solvent line as internal standard. Splitting patterns are designated as s, singlet; d, doublet; t, triplet; q, quartet; m, multiplet; br, broad. The NMR spectra were recorded at a temperature ranging from 25 to 90° C. When more than one conformer was detected the chemical shifts for the most abundant one is reported.

LC-MS Data (LC-MS) is typically generated on an Waters ZQ Mass Spectrometer, operating in switched ES+ and ES– ionization modes coupled to an Agilent 1100 Series HPLC system with in line Aglient 1100 UV-DAD and Sedere SEDEX 75 ELSD Detection. Instrument control and data acquisition is mediated through the Waters MassLynx-OpenLynx software suite. Separation was performed on a Waters SunFire C18 (30×4.6 mm, 3.5 μm) column Flow Rate: 3.0 mL/min. column temperature 30° C. Injection Volume: 5.0 μL. Mobile phase [A]: 3:97:0.05 (v/v/v) Acetonitrile:Water:Formic Acid. Mobile Phase [B]: 97:3:0.05 (v/v/v) Acetonitrile:Water:Formic Acid. Gradient: 97% [A] 3% [B] for 0.1 min. Ramp to 3% [A] 97% [B] at 4.0 min. Hold at 97% [B] to 5 min. Return to 97% [A] at 6 min. Detector parameters: UV-DAD: Range 190 to 450 nm, Interval 2 nm, Threshold 0.1 mAU. ELSD: Temperature 40° C., Range 8. Mass Spectrometer: ES+: Mass Range 125 to 625 in 0.50 sec. Interscan delay 0.25 sec. Capillary 4.0 kV. ES–: Mass Range 125 to 625 in 0.50 sec. Interscan delay 0.25 sec. Capillary 3.0 kV.

In the mass spectra only one peak in the molecular ion cluster is usually reported.

For reactions involving microwave irradiation, a Biotage Initiator was used.

Chiral chromatography was typically performed using a ChiralPak™ AD-H or IA column from Daicel® using heptane/ethanol or heptane/ethanol/methanol mixtures as eluent. Analytical chiral HPLC was carried out either on an Agilent 1100 series HPLC system or on a Gilson HPLC system using a 250×4.6 mm column and a flow rate of 1 ml/min. Preparative chiral HPLC was carried out using a Gilson preparative HPLC system on a 250×19 mm semipreparative column with a flow rate of 18 ml/min.

Flash silica gel chromatography was carried out on silica gel 230-400 mesh (supplied by Merck AG Darmstadt, Germany) or over pre-packed Biotage silica or NH silica cartridges.

Optical rotations were measured using an Optical Activity Ltd AA-10 automatic polarimeter (Cambridge, UK) using a cell of 10 cm path length and in chloroform solution unless otherwise indicated.

SCX cartridges are ion exchange solid phase extraction columns supplied by Varian. The eluent used with SCX cartridges is methanol followed by 0.2-2.0 M ammonia solution in methanol.

In most preparations, purification was performed using Biotage automatic flash chromatography (SP4 or Isolera) systems.

The following abbreviations are used herein:
AD-H ChiralPak AD-H semipreparative column
Boc tertButyloxycarbonyl
CBz Benzyloxycarbonyl
$CHCl_3$ Chloroform
Dppf 1,1'-Bis(diphenylphosphino)ferrocene
DBU 1,8-Diazabicyclo (5.4.0)undec-7-Ene
DCM Dichloromethane
DCE 1,2-Dichloroethane
DME Dimethoxyethane
DMF Dimethylformamide
DMSO Dimethylsulfoxide
EtOAc Ethyl Acetate
$Et_2O$ Ether
HCl Hydrochloric Acid
HPLC High-performance liquid chromatography
IA ChiralPak IA semipreparative column
IPA Isopropyl alcohol
$K_2CO_3$ Potassium carbonate
LC-MS Liquid chromatography-Mass spectrometry
MeCN Acetonitrile
MeOH Methanol
$MgSO_4$ Magnesium sulfate
$Na_2CO_3$ Sodium carbonate
NMR Nuclear Magnetic Resonance
NaOH Sodium hydroxide
$Na_2SO_4$ Sodium sulfate
$PdCl_2(Ph_3P)_2$ Bis(triphenylphosphine)palladium(II) chloride
SEM trimethylsilylethyloxymethyl
$SiO_2$ Silica gel
TFA Trifluoroacetic acid
TFAA Trifluoroacetic anhydride
THF Tetrahydrofuran Preparation of Intermediates Description 1

3-(Benzhydrylidene-amino)-1-methyl-pyrrolidin-2-one (D1)

Method 1:

Benzophenone imine [CAS: 1013-88-3] (16.67 g, 91.98 mmol) was added dropwise to a solution of 3-amino-1-methylpyrrolidine-2-one [CAS 119329-48-5] (10 g, 87.60 mmol) in DCE (100 mL) under $N_2$ and the reaction was heated at reflux for 18 hours. The solvent was evaporated to afford an amber oil. This was purified using flash silica in a large sinter funnel, eluting with 4:1 to 3:7 i-hexane:EtOAc. An incomplete separation was achieved. 3-(Benzhydrylidene-amino)-1-methyl-pyrrolidin-2-one (D1) was isolated (25 g) with approximately 11% of an impurity present, but was used in the next step without further purification;

300 MHz NMR $\delta_H$ ($CDCl_3$) 2.15-2.49 (2H, m), 2.90 (3H, s), 3.26-3.34 (1H, abq), 3.52 (1H, dt), 4.23 (1H, t), 7.30-7.49 (8H, m), 7.63-7.67 (2H, m).

Method 2:

Benzophenone imine (200.04 g, 1103.8 mmol) was added dropwise over 20 minutes to a stirred solution of 3-amino-1-methylpyrrolidine-2-one (120 g, 1051.2 mmol) in DCE (1000 mL) at ambient temp under nitrogen in a 2 L flask fitted with a magnetic stirrer bar. The reagent was washed with further DCE (100 mL). The stirred solution was heated at reflux on a heat-on block at a block temp of 95° C. for 7 h, using a N₂ bubbler with exhaled gas passing through a safety trap then into 2 L of water via an upturned funnel (for scrubbing NH₃ gas, estimated to be approx 23 L). The reaction was left to stand at ambient temp overnight under N₂. The mixture was evaporated to a thick, off-white oil. To this was added Et₂O (700 ml) and to this stirred solution, as it began to crystallize, was added iso-hexane (700 ml) over 2 minutes. The mixture was stirred for 1 h then filtered under suction and washed with Et₂O/iso-hexane (1:1) (500 ml). The white solid was dried at 35° C. under vacuum for 3 h to afford 3-(benzhydrylidene-amino)-1-methyl-pyrrolidin-2-one (D1) (259.4 g, 88.6%). The NMR was consistent with pure material.

Description 2

3-(Benzhydrylidene-amino)-1-methyl-3-prop-2-ynyl-pyrrolidin-2-one (D2)

Method 1:
Potassium tert-butoxide 1.7M in THF (32.8 mL, 55.76 mmol) was added dropwise over a period of 80 minutes (by syringe pump) to a solution of the 3-(benzhydrylidene-amino)-1-methyl-pyrrolidin-2-one (14.11 g, 50.692 mmol) (which may be prepared as described in Description 1) and propargyl bromide (6.78 mL, 60.83 mmol) in THF (250 mL) at 0° C. under nitrogen. The reaction was stirred for 2 hours. Additional KOᵗBu (5 ml) was added dropwise and stirring was continued for 15 mins. The reaction was quenched by the addition of satd. aq. NaHCO₃ and diluted with EtOAc. The phases were separated, the organic layer was dried (Na₂SO₄) and the solvent evaporated to afford a crude brown oil which solidified on standing. This waxy-solid was suspended in IPA (approx. 30 ml) and stirred for 1 hr. The solid was filtered off, washed with a little IPA to afford 3-(benzhydrylidene-amino)-1-methyl-3-prop-2-ynyl-pyrrolidin-2-one (D2) as a light brown solid (6.26 g);

300 MHz NMR $\delta_H$ (CDCl₃) 1.95 (1H, t), 2.14-2.24 (1H, m), 2.44 (3H, s), 2.45-2.64 (2H, m), 2.94 (2H, t), 3.11 (1H, dt), 7.23-7.48 (8H, m), 7.55-7.59 (2H, m).

Method 2:
Potassium tert-butoxide 1.7M in THF (602.08 mL, 1023.5 mmol) was added dropwise over a period of 2.5 h to a stirred solution of 3-(benzhydrylidene-amino)-1-methyl-pyrrolidin-2-one (259 g, 930.48 mmol)) (which may be prepared as described in Description 1) and 80% solution propargyl bromide in toluene (124.37 mL, 1116.6 mmol) in 3A-molecular-sieve-dried reagent grade THF (1900 mL) at −65° C. under nitrogen, in a 5 L flask equipped with an overhead stirrer. After the addition was complete, the mixture was stirred at −65° C. for a further 1 h. The cooling bath was removed and a saturated solution of NaHCO₃ (140 ml) was added over 1 minute (at −60° C.). After a further 5 mins more sat NaHCO₃ solution (1.4 L) was added followed by Et₂O (1.4 L). The mixture was stirred for 1 h then transferred to a separating funnel and water (1.4 L) was added to dissolve all solids. The layers were separated and the aqueous further extracted with Et₂O (2×1 L). The combined organic extracts were re-washed with sat. brine (700 ml), diluted with water (700 ml). The organic layer was dried (MgSO₄) and evaporated to a volume of approx. 500-600 ml whereupon crystallization started to occur. To this stirred mixture was then added iso-hexane (1.6 L). After standing for 15 mins the cream solid was filtered under suction and washed with iso-hexane (500 ml) and dried at 50° C. under vacuum for 5 h. This afforded 3-(benzhy-drylidene-amino)-1-methyl-3-prop-2-ynyl-pyrrolidin-2-one (D2) (274 g, 93%). This was pure by NMR but contains some additional water.

Description 3

(3S)-3-Amino-1-methyl-3-prop-2-ynyl-pyrrolidin-2-one (D3S) and (3R)-3-Amino-1-methyl-3-prop-2-ynyl-pyrrolidin-2-one (D3R)

Method 1:
Citric acid monohydrate (10.39 g, 49.46 mmol) was added to a solution of 3-(benzhydrylidene-amino)-1-methyl-3-prop-2-ynyl-pyrrolidin-2-one (6.26 g, 19.79 mmol) (which may be prepared as described in Description 2) in THF (150 mL) and the reaction was stirred at room temperature for 18 hours. A colourless solid precipitated out. The solvent was evaporated to give a gummy white solid. This was triturated with Et₂O and the solid was washed with further Et₂O. The solid was suspended in water/MeOH and purified by SCX (70 g Silca), eluting with water/MeOH, MeOH and finally 0.5M NH₃ in MeOH. Fractions containing product were evaporated to afford 3-amino-1-methyl-3-prop-2-ynyl-pyrrolidin-2-one (3.23 g, 21.223 mmol) as a pale yellow oil;

300 MHz NMR $\delta_H$ (CDCl₃) 1.65 (2H, br.s), 1.94-2.05 (2H, m), 2.31-2.39 (1H, m), 2.41-2.55 (2H, m), 2.89 (3H, Me), 3.33-3.39 (2H, m).

Method 2:
To a stirred solution of 3-(benzhydrylideneamino)-1-methyl-3-prop-2-ynyl-pyrrolidin-2-one (274 g, 865.99 mmol) (which may be prepared as described in Description 2) in a 5 L flask equipped with an overhead stirrer, in THF (2.7 L) was added citric acid monohydrate (363.96 g, 1732 mmol) in one portion. The solution was stirred at room temperature for 18 h, giving a thick white precipitate with some sticky solid adhering to the sides of the flask. This sticky solid was loosened with a spatula, then diethyl ether (1.3 L) was added and rapid stirring was continued for a further 1 h. The solid was then filtered under suction and washed efficiently with Et₂O (2×1 L) and dried at 50° C. under vacuum for 3 hours. This produced 268 g of material. This was recrystallized from hot MeOH (1.9 L); hot solution was filtered under suction to give a clear pale yellow solution. The solution was left to stand for 1 h and Et₂O (3 L) was added with stirring. After standing for a further 1 h, the mixture was filtered and washed with MeOH:Et₂O (1:2) (1 L) and the solid pressed dry and further dried at 50° C. under vacuum for 6 hours to afford 312 g of the citrate salt, contaminated with methanol. In a separate container, Ambersep 900 (OH) ion exchange resin (2.31 kg) was stirred for 5 minutes with MeOH (2 L) to pre-wash the resin. The suspended resin was filtered under suction and the moist pre-washed resin was added to a stirred suspension of the previously prepared citrate salt in methanol (3 L) in a 10 L vessel equipped with an overhead stirrer. The mixture was stirred for a total of 1.5 h at ambient temp then filtered under suction. The filtered resin was washed with MeOH (2×1.5 L). The filtrate and washings were evaporated in vacuo to an oil which was redissolved in DCM (1.5 L) and dried (Na₂SO₄), filtered, evaporated to a pale yellow oil, which was dried at RT overnight to give 3-amino-1-methyl-3-prop-2-ynyl-pyrrolidin-2-one (106.9 g, 79.9%). NMR showed this to be pure material identical to that prepared in Description 3, Method 1. A portion of this material (1.75 g, 11.5 mmol) was separated on chiral HPLC using a semi-prep AD-H column, eluting with 20% EtOH/heptane at 18 ml/min. Peaks were identified at 215 nm:

(3S)-3-amino-1-methyl-3-prop-2-ynyl-pyrrolidin-2-one D3S 549 mg retention time=13.7 mins; Optical rotation α[D/22]=−81.0 (c=0.975, CHCl₃).

(3R)-3-amino-1-methyl-3-prop-2-ynyl-pyrrolidin-2-one D3R 407 mg retention time=17.9 mins; Optical rotation α[D/22]=+78.8 (c=0.965, CHCl₃).

Method 3:

A controlled lab reactor with heater/cooler jacket and an overhead paddle-stirrer was charged with IPA (2250 mL) and (2S)-2-(6-methoxy-2-naphthyl)propanoic acid (84.72 g, 367.92 mmol) was added. The suspension was stirred and warmed to 75° C. giving a solution. A solution of 3-amino-1-methyl-3-prop-2-ynyl-pyrrolidin-2-one (which may be prepared as described in Description 3, Method 2) (55.99 g, 367.92 mmol) in IPA (1100 mL) was then added dropwise over 1.5 hours. In a cooling process, the reaction mixture was stirred at 75° C. for 1 hr then cooled to 55° C. over 1 hr. The reaction was seeded with pure (S) isomer salt at every 1 degree drop in temperature until the seed remained out of solution (ca. 71° C.). The reaction mixture crystallised and was stirred at 55° C. for 1 hr. The mixture was then cooled to 40° C. over approximately 20 minutes and filtered under suction into a pre-warmed filter funnel over a fast filter paper. The vessel was rinsed out with IPA (600 mL) pre-warmed to 40° C. and this was used to wash the collected solids. The solids were dried under suction until no more solvent came out and then were dried in a vacuum oven at 50° C. to give a white solid, 59.37 g (3S)-1-methyl-2-oxo-3-prop-2-ynyl-pyrrolidin-3-yl]ammonium (2S)-2-(6-methoxy-2-naphthyl)propanoate. A portion of this material was removed and dissolved in methanol, passed down an SCX column, washed with methanol and then eluted with 0.5M ammonia in methanol. The ammonia eluent was evaporated to a pale yellow gum, which was analysed by chiral HPLC (20:80 EtOH:heptane, IA column) showing S-isomer 99.5% and R-isomer 0.5%. Ambersep 900-OH (500 g) was stirred in methanol (1000 mL) for 5 minutes, then filtered and dried under suction until no more liquid came out. The washed resin was added to a stirred suspension of S-isomer salt (59.37 g, 155.24 mmol) in methanol (1000 mL). The mixture was stirred for 1 hr, then filtered. The resin was resuspended in methanol (1000 mL) and stirred for an hour and then filtered. The combined filtrates were evaporated to give a slightly cloudy yellow oil. The oil was dissolved in dichloromethane (ca. 200 mL) and dried over magnesium sulphate, filtered and evaporated to give a clear yellow oil (3S)-3-amino-1-methyl-3-prop-2-ynyl-pyrrolidin-2-one (D3S) (22.729 g). This material was characterised as identical to that prepared by chiral chromatography in Method 2.

Method 4:

Enriched recrystallisation mother liquors containing, for example, a 91:9 ratio of (3R)-3-amino-1-methyl-3-prop-2-ynyl-pyrrolidin-2-one (2S)-2-(6-methoxy-2-naphthyl)propanoic acid salt and its (3S) enantiomer, (27 g) (which may be obtained from the fractional crystalisation procedure described in Description 3 Method 3) were evaporated and dissolved in acetonitrile at 30±5° C. The reaction mass was heated to 70±5° C. and stirred for 10 minutes then slowly cooled to 40±2° C. A seed of the R-amine-(2S)-2-(6-methoxy-2-naphthyl)propanoic acid salt was introduced and the reaction mixture maintained at 40±2° C. for 1 hr. The reaction mass was cooled to 30±5° C. and filtered. The isolated salt was washed with acetonitrile and dried under vacuum at 47.5±2.5° C. for 6±1 hours to give 18.2 g of the salt with a 99.8% enantiomeric excess of the R isomer. The material was then converted to the free base form as described for the S-enantiomer in Method 3 to give the title compound (D3R). This material was characterised as identical to that prepared by chiral chromatography in Method 2.

Description 4 tert-Butyl N-[(3S)-1-methyl-2-oxo-3-prop-2-ynyl-pyrrolidin-3-yl]carbamate (D4)

Method 1:

Boc₂O (944.75 mg, 4.33 mmol) was added to a solution of (3S)-3-amino-1-methyl-3-prop-2-ynyl-pyrrolidin-2-one (which may be prepared as described in Description 3) (549 mg, 3.61 mmol) in DCM (20 mL) at 20° C. and the reaction was stirred for 18 hrs. The solvent was evaporated and the residue purified on a Biotage Isolera with a 25 g SNAP cartridge, eluting with 0 to 100% EtOAc/i-hexane to afford tert-butyl N-[(3S)-1-methyl-2-oxo-3-prop-2-ynyl-pyrrolidin-3-yl]carbamate (D4) (849 mg, 3.365 mmol, 93.3% yield) as a pale yellow solid.

Method 2:

Boc₂O (2.77 g, 12.69 mmol) was added to a solution of (3S)-3-amino-1-methyl-3-prop-2-ynyl-pyrrolidin-2-one (which may be prepared as described in Description 3) (1.61 g, 10.58 mmol) in DCM (40 mL) at 20° C. and the reaction was stirred for 18 h. The reaction was warmed to 40° C. and stirred for a further 3 days. The solvent was evaporated and the residue purified using a Biotage Isolera with a 25 g SNAP cartridge eluting with 0 to 80% EtOAc/i-hexane to afford tert-butyl N-[(3S)-1-methyl-2-oxo-3-prop-2-ynyl-pyrrolidin-3-yl]carbamate (D4) (2.52 g, 9.9877 mmol, 94.4% yield) as a pale yellow solid;

300 MHz NMR $\delta_H$ (CDCl₃) 1.45 (9H, s), 2.02 (1H, t), 2.48-2.59 (3H, m), 2.27-2.35 (1H, br.s), 2.92 (3H, s), 2.38-2.44 (2H, m), 5.23 (1H, br.s);

Optical rotation α[D/22]=−2 (c=1.01, CHCl₃).

Method 3:

To a solution of (3S)-3-amino-1-methyl-3-prop-2-ynyl-pyrrolidin-2-one (which may be prepared as described in Description 3) (72.66 g, 477.4 mmol) in DCM (1000 mL) was added a solution of Boc₂O (125.03 g, 572.88 mmol) in DCM (700 mL) in one portion. The reaction was then stirred at 40° C. (bath temp. not internal temp.) over 5 hrs, then at room temperature over the weekend. The reaction was concentrated in vacuo, and the residue was suspended in a mixture of Et₂O and isohexane (1:1, 250 mL) and stirred for 30 minutes. The suspension was filtered, and the solid was washed with a mixture of Et₂O and isohexane (1:1, 250 mL), followed by isohexane (3×250 mL). The solid was then dried in a vacuum oven for 2 hours (40° C.) to give a white solid, tert-butyl N-[(3S)-1-methyl-2-oxo-3-prop-2-ynyl-pyrrolidin-3-yl]carbamate (D4) (99.25 g);

300 MHz NMR $\delta_H$ (CDCl₃) 1.43 (9H, s), 2.01 (1H, app.t), 2.45-2.59 (3H, m), 2.78, 2.82 (1H, 2×br.s), 2.81 (3H, s), 3.35-3.45 (2H, m), 5.23 (1H, br.s).

A second crop was isolated from the filtrate to give a further batch, 5.535 g of similar purity.

Description 5

2-Chloro-4-[4-(trifluoromethyl)phenyl]pyrimidine (D5)

To a solution of 2,4-dichloropyrimidine (10 g, 67.12 mmol) in 1,2-dimethoxyethane (75 mL) and water (50 mL) was added sodium carbonate (21343 mg, 201.38 mmol), and 4-(trifluoromethyl)-phenylboronic acid (12111 mg, 63.77 mmol). Bis(triphenylphosphine)palladium (II) dichloride (2355.6 mg, 3.36 mmol) was then added and the reaction was heated to 90° C. for 2 hours, then allowed to cool to room temperature overnight. The reaction was partitioned between water (300 mL) and EtOAc (300 mL). The organics were washed with brine (100 mL), dried over MgSO$_4$ and concentrated in vacuo to give 20 g of crude product. Multiple recrystallisations from EtOAc gave 6 g of a pale orange solid which was purified over silica (100 g, SNAP), eluting with EtOAc:isohexane 0%->50% to give the desired product 2-chloro-4-[4-(trifluoromethyl)phenyl]pyrimidine (D5) (5020 mg, 19.41 mmol, 28.9% yield) as colourless crystals.

300 MHz NMR $\delta_H$(CDCl$_3$) 7.72 (1H, d), 7.81 (2H, d), 8.24 (2H, d), 8.74 (1H, d).

Description 6

2-Iodo-4-[4-(trifluoromethyl)phenyl]pyrimidine (D6)

2-Chloro-4-[4-(trifluoromethyl)phenyl]pyrimidine (which may be prepared as described in Description 5) (1.22 g, 4.72 mmol) was added portionwise to HI (57% in water) (4.98 mL, 37.74 mmol) at 0° C. and the dark mixture was stirred for 40 mins. Dichloromethane (5 mL) was added and the resultant light brown mixture was stirred at 0° C. for 18.25 hrs. Additional dichloromethane (5 mL) was added followed by HI (57% in water) (1.87 mL, 14.15 mmol) and vigorous stirring was continued at 0° C. for a further 18 hrs. The mixture was quenched by the addition of satd. aq. K$_2$CO$_3$ (care: gas evolved). After basification, satd. sodium metabisulphite was added and stirring was continued for 5 mins. The mixture was diluted with further DCM and the phases were separated. The organic layer was dried (Na$_2$SO$_4$) and the solvent evaporated to afford the 2-iodo-4-[4-(trifluoromethyl)phenyl]pyrimidine (D6) (1.57 g, 4.48 mmol, 95.1% yield) as a yellow solid.

300 MHz NMR $\delta_H$(CDCl$_3$) 7.74 (1H, d), 7.79 (2H, d), 8.20 (2H, d), 8.55 (1H, d).

Description 7 tert-Butyl N-[(3S)-1-methyl-2-oxo-3-[3-[4-[4-(trifluoromethyl)phenyl]pyrimidin-2-yl]prop-2-ynyl]pyrrolidin-3-yl]carbamate (D7)

Copper iodide (25.51 mg, 0.1300 mmol), followed by PdCl$_2$(Ph$_3$P)$_2$ (47.01 mg, 0.0700 mmol) was added portionwise to a solution of 2-iodo-4-[4-(trifluoromethyl)phenyl]pyrimidine (which may be prepared as described in Description 6) (703.46 mg, 2.01 mmol), tert-butyl N-[(3S)-1-methyl-2-oxo-3-prop-2-ynyl-pyrrolidin-3-yl]carbamate (which may be prepared as described in D4) (338 mg, 1.34 mmol) and Et$_2$NH (0.69 mL, 6.7 mmol) in THF (10 mL) under N$_2$ and the reaction was stirred at 20° C. for 18 hrs. The reaction was diluted with EtOAc and water was added. The phases were separated and the organic layer was dried (Na$_2$SO$_4$) and the solvent evaporated to afford a brown oil. This was purified by using a Biotage SP4, with a 25 g SNAP cartridge, eluting with 0 to 100% EtOAc in i-hexane to afford tert-butyl N-[(3S)-1-methyl-2-oxo-3-[3-[4-[4-(trifluoromethyl)phenyl]pyrimidin-2-yl]prop-2-ynyl]pyrrolidin-3-yl]carbamate (D7) (555 mg, 1.17 mmol, 87.3% yield) as a yellow oil.

300 MHz NMR $\delta_H$ (CDCl$_3$) 1.49 (9H, s), 2.48-2.68 (2H, m), 2.89 (2H, dt), 3.00 (1H, s), 3.17-3.22 (1H, br.d), 3.39-3.49 (1H, m), 3.66-3.74 (1H, m), 3.38 (1H, br.s), 5.4 (1H, br.s) 7.68 (1H, d), 7.80 (2H, d), 8.23 (2H, d), 8.80 (1H, d).

Optical rotation α[D/22]=−81.0 (c=1.09, CHCl$_3$).

Description 8

(3S)-3-Amino-1-methyl-3-[3-[4-[4-(trifluoromethyl)phenyl]pyrimidin-2-yl]prop-2-ynyl]pyrrolidin-2-one (D8)

Trifluoroacetic acid (2 mL, 26.9 mmol) was added to a solution of tert-butyl N-[(3S)-1-methyl-2-oxo-3-[3-[4-[4-(trifluoromethyl)phenyl]pyrimidin-2-yl]prop-2-ynyl]pyrrolidin-3-yl]carbamate (which may be prepared as described in Description 7) (555 mg, 1.17 mmol) in dichloromethane (10 mL) at 20° C. and the reaction was stirred for 1 hr. The reaction was quenched by the addition of sat. NaHCO$_3$ and the phases were separated. The organic layer was dried (Na$_2$SO$_4$) and the solvent evaporated to afford the (3S)-3-amino-1-methyl-3-[3-[4-[4-(trifluoromethyl)phenyl]pyrimidin-2-yl]prop-2-ynyl]pyrrolidin-2-one (D8) (340 mg, 0.9082 mmol, 77.6% yield) as a yellow oil.

300 MHz NMR $\delta_H$ (CDCl$_3$) 1.7 (2H, br.s), 2.06-2.16 (1H, m), 2.49 (1H, ddd), 2.24-2.39 (2H, abq), 2.94 (3H, s), 3.38-3.54 (2H, m), 7.67 (1H, d), 7.79 (2H, d), 8.22 (2H, d), 8.80 (1H, d).

Description 9

(5S)-7-Methyl-2-[4-[4-(trifluoromethyl)phenyl]pyrimidin-2-yl]-1,7-diazaspiro[4.4]non-1-en-6-one (D9)

Silver trifluoromethanesulphonate (23.34 mg, 0.0900 mmol) was added to a solution of (3S)-3-amino-1-methyl-3-[3-[4-[4-(trifluoromethyl)phenyl]pyrimidin-2-yl]prop-2-ynyl]pyrrolidin-2-one (which may be prepared as described in Description 8) (340 mg, 0.9100 mmol) in MeCN (10 mL) and the reaction was stirred at 20° C. for 18 hrs. Additional AgOTf (0.1 eq) was added and stirring was continued for 3 days. Additional AgOTf was added and stirring was continued for a further 3 days. The solvent was evaporated and the residue was dissolved in EtOAc/satd. NaHCO$_3$. The phases were separated and the organic layer was dried (Na$_2$SO$_4$) and the solvent evaporated to afford (5S)-7-methyl-2-[4-[4-(trifluoromethyl)phenyl]pyrimidin-2-yl]-1,7-diazaspiro[4.4]non-1-en-6-one (D9) (340 mg, 0.9082 mmol, 100% yield) as an amber oil.

300 MHz NMR $\delta_H$ (CDCl$_3$) 2.20-2.38 (2H, m), 2.60-2.74 (2H, m), 2.91 (3H, s), 3.34-3.45 (1H, m), 3.56-3.69 (3H, m), 7.74 (2H, d), 7.92 (1H, d), 8.16 (2H, d), 9.05 (1H, d).

Description 10 tert-Butyl N-[(3R)-1-methyl-2-oxo-3-prop-2-ynyl-pyrrolidin-3-yl]carbamate (D10)

Boc$_2$O (777.8 mg, 3.56 mmol) was added to a solution of (3R)-3-amino-1-methyl-3-prop-2-ynyl-pyrrolidin-2-one (which may be prepared as described in Description 3) (452 mg, 2.97 mmol) in DCM (20 mL) at 20° C. and the reaction was stirred for 18 hrs. The solvent was evaporated and the residue purified using a Biotage Isolera, with a 25 g SNAP cartridge, eluting with 0 to 100% EtOAc/i-hexane to afford the tert-butyl N-[(3R)-1-methyl-2-oxo-3-prop-2-ynyl-pyrrolidin-3-yl]carbamate (D10) (688 mg, 2.73 mmol, 91.8% yield) as a pale yellow solid. The NMR was identical to its stereoisomer D4.

Description 11

2-Chloro-4-methyl-6-[4-(trifluoromethyl)phenyl]pyrimidine (D11)

Method 1:
To a solution of 2,4-dichloro-6-methyl-pyrimidine (5 g, 30.67 mmol) in 1,2-dimethoxyethane (35 mL) and water (25 mL) was added sodium carbonate (9.75 g, 92.03 mmol), and 4-(trifluoromethyl)-phenylboronic acid (5.53 g, 29.14 mmol). This was degassed with nitrogen for 5 minutes. The bis(triphenylphosphine)palladium (II) dichloride (1.08 g, 1.53 mmol) was then added and the reaction was heated to 90° C. overnight. The solvent was evaporated and the residue was partitioned between water (300 mL) and EtOAc (300 mL). The organics were washed with brine (100 mL), dried over MgSO$_4$ and concentrated in vacuo to afford a yellow oil. The material was purified using a Biotage SP4, 0 to 50% i-hexane/EtOAc and the fractions containing the lower (major) spot were collected and the solvent evaporated to afford the 2-chloro-4-methyl-6-[4-(trifluoromethyl)-phenyl]pyrimidine (D11) (4.65 g, 17.06 mmol, 55.6% yield) as a colourless solid.

300 MHz NMR δ$_H$(CDCl$_3$) 2.65 (3H, s), 7.57 (1H, s), 7.79 (2H, d), 8.21 (2H, d).

Method 2:

To a solution of 4-(trifluoromethyl)phenylboronic acid (116.52 g, 613.5 mmol) in 1,2-dimethoxyethane (1200 mL) was added 2,4-dichloro-6-methylpyrimidine (100 g, 613.5 mmol). To this stirring solution was added a solution of sodium carbonate (195.07 g, 1840.5 mmol) dissolved in water (600 mL) giving some precipitation of the base and then bis(triphenylphosphine)palladium (II) dichloride (2.15 g, 3.07 mmol). The mixture was brought to 50° C. over about 1 hr then stirred at this temperature overnight. The reaction mixture cooled to approx. 30° C., filtered and washed with DCM (approx. 500 mL). The filtrate was evaporated to remove the bulk of the organic solvents. To the residues was added DCM (250 mL) and the phases were separated. The aqueous phase was extracted with DCM (2×250 mL) and the combined extracts were washed with brine (250 mL), dried over magnesium sulphate, filtered and evaporated to a brown gummy solid. The solid was stirred in iso-hexane (150 mL) at 60° C. until the solid had dissolved. The heat was turned off and the flask allowed to cool in the heat-on block naturally. When the solution was at 30° C. seed crystals were added causing immediate crystallisation. The mixture was stood overnight then the crystalline material was crushed and filtered. The solids were washed with cold iso-hexane (2×50 mL) and dried to give the title compound (D11) as a slightly sticky tan solid, (96.17 g) consistent by NMR with that prepared by Method 1.

Description 12

2-Iodo-4-methyl-6-[4-(trifluoromethyl)phenyl]pyrimidine (D12)

Method 1:

Hydroiodic acid (57% in water, 9.68 mL, 73.41 mmol) was added portionwise to 2-chloro-4-methyl-6-[4-(trifluoromethyl)phenyl]pyrimidine (which may be prepared as described in Description 11) (1.38 g, 5.06 mmol) in DCM (30 mL) at 20° C. and the dark mixture was stirred for 18 hrs. The mixture was quenched by the addition of sat. aq. K$_2$CO$_3$ (care: gas evolved). After basification, satd. aq. sodium metabisulphite was added and stirring was continued for 5 mins. The mixture was diluted with further DCM and the phases were separated. The organic layer was dried (Na$_2$SO$_4$) and the solvent evaporated to afford 2-iodo-4-methyl-6-[4-(trifluoromethyl)phenyl]pyrimidine (D12) (1.58 g, 4.34 mmol, 85.7% yield) a yellow solid, containing about 20% of the reduced H-compound.

300 MHz NMR δ$_H$(CDCl$_3$) 2.59 (3H, s), 7.58 (1H, s), 7.77 (2H, d), 8.17 (2H, d)

Method 2:

To a solution of 2-chloro-4-methyl-6-[4-(trifluoromethyl)phenyl]pyrimidine (which may be prepared as described in Description 11) (167.5 g, 614.34 mmol) in DCM (1325 mL) was added HI (57% in water) (405.23 mL, 3071.7 mmol) dropwise. The reaction was then stirred at room temperature overnight. Additional DCM (500 mL) was added, and the reaction was filtered. The solid was dried then transferred into a beaker containing water (1 L) and EtOAc (1.25 L). The aqueous was basified to pH 10 with K$_2$CO$_3$, and the layers were stirred until all the solid dissolved. Sodium metabisulfite (8.75 g) was added and the layers were stirred until all solid dissolved. The layers were separated, and the aqueous was re-extracted with EtOAc (200 mL). The combined organics were then dried over MgSO$_4$, filtered and concentrated in vacuo to give the title material (D12) (205.68 g, 564.9 mmol, 92% yield) as a pale orange solid. NMR indicated this was >95% pure.

Description 13 tert-Butyl N-[(3R)-1-methyl-3-[3-[4-methyl-6-[4-(trifluoromethyl)phenyl]pyrimidin-2-yl]prop-2-ynyl]-2-oxo-pyrrolidin-3-yl]carbamate (D13)

Copper iodide (22.64 mg, 0.1200 mmol), followed by PdCl$_2$(Ph$_3$P)$_2$ (41.73 mg, 0.060 mmol) was added portionwise to a solution of tert-butyl N-[(3R)-1-methyl-2-oxo-3-prop-2-ynyl-pyrrolidin-3-yl]carbamate (which may be prepared as described in Description 10) (300 mg, 1.19 mmol), 2-iodo-4-methyl-6-[4-(trifluoromethyl)phenyl]pyrimidine (which may be prepared as described in Description 12) (584.44 mg, 1.61 mmol) and Et$_2$NH (0.62 mL, 5.95 mmol) in THF (10 mL) under N$_2$ and the reaction was stirred at 20° C. for 18 hrs. The solvent was evaporated and the residue was purified by Biotage SP4, using a 25 g SNAP cartridge, eluting with 0 to 100% EtOAc/i-hexane affording tert-butyl N-[(3R)-1-methyl-3-[3-[4-methyl-6-[4-(trifluoromethyl)phenyl]pyrimidin-2-yl]prop-2-ynyl]-2-oxo-pyrrolidin-3-yl]carbamate (D13) (482 mg, 0.987 mmol, 83.0% yield) as a pale yellow foam.

300 MHz NMR δ$_H$ (CDCl$_3$) 1.46 (9H, s), 2.5-2.75 (2H, m), 2.62 (3H, s), 2.79-2.85 (1H, br.d), 2.98 (3H, s), 3.13-3.19 (1H, br.d), 3.40-3.47 (1H, br.t), 3.63-3.72 (1H, m), 5.35 (1H, br.s), 7.53, 1H, s), 7.78 (2H, d), 8.19 (2H, d).

Description 13a tert-Butyl N-[(3S)-1-methyl-3-[3-[4-methyl-6-[4-(trifluoromethyl)phenyl]pyrimidin-2-yl]prop-2-ynyl]-2-oxo-pyrrolidin-3-yl]carbamate (D13a)

Method 1:

Copper Iodide (149.46 mg, 0.7800 mmol), followed by PdCl$_2$(Ph$_3$P)$_2$ (275.41 mg, 0.3900 mmol) was added portionwise to a solution of 2-iodo-4-methyl-6-[4-(trifluoromethyl)phenyl]pyrimidine (4 g, 10.99 mmol) (which may be prepared as described in Description 12), tert-butyl N-[(3S)-1-methyl-2-oxo-3-prop-2-ynyl-pyrrolidin-3-yl]carbamate (1.98 g, 7.85 mmol) (which may be prepared as described in Description 4) and Et$_2$NH (4.06 mL, 39.24 mmol) in THF (50 mL) under N$_2$ and the reaction was stirred at 20° C. for 18 hrs. The solvent was evaporated and the residue was suspended in EtOAc and washed with water/sat. aq. NaHCO$_3$. The organics were collected, dried (Na$_2$SO$_4$) and the solvent evaporated to afford a brown oil. This was purified using a Biotage SP4, with a 100 g SNAP cartridge, eluting with 50 to 100% EtOAc/i-hexane to afford tert-butyl N-[(3S)-1-methyl-3-[3-[4-methyl-6-[4-(trifluoromethyl)phenyl]pyrimidin-2-yl]prop-2-ynyl]-2-oxo-pyrrolidin-3-yl]carbamate (D13a) (4.09 g, 8.3726 mmol) as a pale yellow foam. The NMR was the same as that for the R isomer produced in Description 13 but also contained traces of ethyl acetate and impurities.

Method 2:

In a 5 L three-necked flask with overhead paddle stirrer and a nitrogen inlet. tert-butyl N-[(3S)-1-methyl-2-oxo-3-prop-2-ynyl-pyrrolidin-3-yl]carbamate (which may be prepared as described in Description 4) (104.79 g, 415.32 mmol) was suspended in tert-Butyl methyl ether (2100 mL). 2-Iodo-4-methyl-6-[4-(trifluoromethyl)phenyl]pyrimidine (which may be prepared as described in Description 12) (166.34 g, 456.85 mmol) was added followed by diisopropylamine (174.63 mL, 1246 mmol) and the mixture was stirred over 20 mins. To the suspension was added copper iodide (1.58 g, 8.31 mmol) followed by bis(triphenyl-phosphine)palladium (II) dichloride (2.92 g, 4.15 mmol) and the mixture was stirred at room temperature for 3 hours. Water (1000 mL) was added and the mixture stirred for 30 mins. The phases were separated and the organic phase, washed with water (2×500 mL), dried over magnesium sulphate, filtered and evaporated to a tan foam, 230 g. The material was purified in three batches of approximately 75 g by column chromatography using an 800 g (Biotage 75L) column and eluting with a gradient of acetone in iso-hexane. This gave the title compound (D13a) (179.3 g) in good purity by NMR and consistent spectroscopically with that produced by Method 1 and the R isomer in Description 13.

Description 14

(3R)-3-Amino-1-methyl-3-[3-[4-methyl-6-[4-(trifluoromethyl)phenyl]pyrimidin-2-yl]prop-2-ynyl]pyrrolidin-2-one (D14)

Trifluoroacetic acid (2 mL, 26.92 mmol) was added to a solution of tert-butyl N-[(3R)-1-methyl-3-[3-[4-methyl-6-[4-(trifluoromethyl)phenyl]pyrimidin-2-yl]prop-2-ynyl]-2-oxo-pyrrolidin-3-yl]carbamate (which may be prepared as described in Description 13) (482 mg, 0.99 mmol) in DCM (10 mL) at 20° C. and the reaction was stirred for 1 hour. Solid $K_2CO_3$ was added to quench the TFA present (care: gas evolved) and the resultant solid was filtered off and washed five times with DCM. The solvent was evaporated to give (3R)-3-amino-1-methyl-3-[3-[4-methyl-6-[4-(trifluoromethyl)phenyl]pyrimidin-2-yl]prop-2-ynyl]pyrrolidin-2-one (D14) (343 mg, 0.883 mmol, 89.5% yield) as a yellow oil. 300 MHz NMR $\delta_H$ (CDCl$_3$) 1.95 (2H, br.s), 2.07-2.17 (1H, m), 2.44-2.53 (1H, m), 2.63 (3H, s), 2.72-2.88 (2H, abq), 2.94 (3H, s), 3.38-3.53 (2H, m), 7.53 (1H, s), 7.78 (2H, d), 8.20 (2H, d).

Description 14a (3S)-3-Amino-1-methyl-3-[3-[4-methyl-6-[4-(trifluoromethyl)phenyl]pyrimidin-2-yl]prop-2-ynyl]pyrrolidin-2-one (D14a)

Method 1:

Trifluoroacetic acid (5 mL, 67.31 mmol) was added to a solution of tert-butyl N-[(3S)-1-methyl-3-[3-[4-methyl-6-[4-(trifluoromethyl)phenyl]pyrimidin-2-yl]prop-2-ynyl]-2-oxo-pyrrolidin-3-yl]carbamate (3.83 g, 7.84 mmol) (which may be prepared as described in Description 13a) in DCM (50 mL) at 20° C. and the reaction was stirred overnight. The reaction was concentrated and a further portion of trifluoroacetic acid (2 ml) added. Stirring was continued for 3 hrs then solid $K_2CO_3$ was added (care: gas evolved) and the mixture was diluted with water. The phases were separated and the organic layer was dried (Na$_2$SO$_4$). The solvent was evaporated to give (3S)-3-amino-1-methyl-3-[3-[4-methyl-6-[4-(trifluoromethyl)phenyl]pyrimidin-2-yl]prop-2-ynyl]pyrrolidin-2-one (D14a) (2.71 g, 6.9775 mmol, 89% yield) as a yellow oil. The NMR was the same as that produced by the R isomer in Description 14 but with some impurities present.

Method 2:

To a solution of tert-butyl N-[(3S)-1-methyl-3-[3-[4-methyl-6-[4-(trifluoromethyl)-phenyl]pyrimidin-2-yl]prop-2-ynyl]-2-oxo-pyrrolidin-3-yl]carbamate (which may be prepared as described in Description 13a) (99.5 g, 203.68 mmol) in 1,4-dioxane (750 mL) cooled with an ice/water bath to an internal temperature of 15° C. was added conc. sulphuric acid (75 mL, 1407 mmol) dropwise maintaining internal temperature below 20° C. over approximately 35 minutes. After complete addition, the reaction mixture was stirred at room temperature over 30 minutes. The reaction was poured into a beaker and washed in with ethyl acetate (400 mL) and a little water. The mixture was cooled to 15° C. and a solution of sodium carbonate (160 g in 1200 mL water) was added over 5 minutes. The mixture was filtered over a pad of celite and the remaining solids washed with ethyl acetate (400 mL). The filtrate phases were separated and the aqueous phase was extracted with ethyl acetate (2×400 mL). The combined organics were washed with brine (500 mL), dried over magnesium sulphate, filtered and evaporated to yield a foaming amber oil. This was twice dissolved in acetonitrile (100 mL) and evaporated and the resulting yellow foam dried under vacuum to give the title material (D14a) in good purity by NMR, consistent spectroscopically with that produced by Method 1 and with the R isomer of Description 14.

Description 14b

3-Amino-1-methyl-3-[3-[4-methyl-6-[4-(trifluoromethyl)phenyl]pyrimidin-2-yl]prop-2-ynyl]pyrrolidin-2-one (D14b)

To a stirred solution of 3-amino-1-methyl-3-prop-2-ynyl-pyrrolidin-2-one (which may be prepared as described in Description 3) (2.3 g, 15.11 mmol) in tert-butyl methyl ether (50 mL) was added 2-iodo-4-methyl-6-[4-(trifluoromethyl)-phenyl]pyrimidine (which may be prepared as described in Description 12) (6.05 g, 16.62 mmol). diisopropylamine (6.35 mL, 45.34 mmol) was then added, followed by copper iodide (57.56 mg, 0.300 mmol) and bis(triphenylphosphine) palladium (II) dichloride (106.07 mg, 0.1500 mmol). The reaction was then stirred at room temperature for 5 days. The reaction mixture was transferred to a separating funnel and the flask washed with an additional quantity of tert-butyl methyl ether (15 ml). The organic solution was washed with water (2×50 mL) and brine (50 mL). The organic phase was dried over magnesium sulphate, filtered, and then the magnesium sulphate washed with dichloromethane (30 ml). The filtrate was concentrated at reduced pressure to give a yellow foam. The product was purified by silica gel chromatography eluting with ethyl acetate followed by an increasing percentage of a solution of 10% 0.880 ammonia in methanol, to give the title compound (D14b) as a yellow foam (4.71 g). This racemate was consistent by NMR and mass spectroscopy with the R isomer prepared in Description 14.

Description 15

(5R)-7-Methyl-2-[4-methyl-6-[4-(trifluoromethyl)phenyl]pyrimidin-2-yl]-1,7-diazaspiro[4.4]non-1-en-6-one (D15)

Silver trifluoromethanesulphonate (22.69 mg, 0.09 mmol) was added to a solution of (3R)-3-amino-1-methyl-3-[3-[4-methyl-6-[4-(trifluoromethyl)phenyl]pyrimidin-2-yl]prop-2-ynyl]pyrrolidin-2-one (which may be prepared as described in Description 14) (343 mg, 0.88 mmol) in MeCN (20 mL) at 20° C. and the reaction was stirred for 18 hrs. The reaction was heated to 40° C. and stirring was continued for 3 days. Additional AgOTf (10 mol %) was added and stirring was continued at 40° C. for 18 hrs. The solvent was evaporated and the residue was purified using a Biotage Isolera with a 25 g SNAP cartridge, eluting with 0 to 100% (mixture of 1% of 2M $NH_3$ in MeOH; 9% MeOH; 90% EtOAc)/EtOAc affording (5R)-7-methyl-2-[4-methyl-6-[4-(trifluoromethyl)phenyl]pyrimidin-2-yl]-1,7-diazaspiro[4.4]non-1-en-6-one (D15) (359 mg, 0.924 mmol) as a light brown solid with a few % of impurities present. 300 MHz NMR $\delta_H$ ($CDCl_3$) 1.89-2.00 (1H, m), 2.16-2.25 (1H, m), 2.59-2.72 (2H, m), 2.72 (3H, s), 2.92 (3H, s), 3.30-3.45 (2H, m), 3.55-3.78 (2H, m), 7.64 (1H, s), 7.79 (2H, d), 8.26 (2H, d).

Description 15a

(5S)-7-Methyl-2-[4-methyl-6-[4-(trifluoromethyl)phenyl]pyrimidin-2-yl]-1,7-diazaspiro[4.4]non-1-en-6-one (D15a)

Method 1:

Silver trifluoromethanesulphonate (358.56 mg, 1.4 mmol) was added to a solution of (3S)-3-amino-1-methyl-3-[3-[4-methyl-6-[4-(trifluoromethyl)phenyl]pyrimidin-2-yl]prop-2-ynyl]pyrrolidin-2-one (2.71 g, 6.98 mmol) (which may be prepared as described in Description 14a) in MeCN (60 mL) at 50° C. and the reaction was stirred for 3 days. Additional AgOTf (10 mol %) was added and stirring was continued for 24 hrs. The solvent was evaporated and the residue was suspended in EtOAc. The organics were washed with water, dried ($Na_2SO_4$) and the solvent evaporated to afford a light brown oil. This was purified using a Biotage Isolera with a 100 g SNAP cartridge, eluting with 0 to 100% (mixture of 1% of 2M $NH_3$ in MeOH; 9% MeOH; 90% EtOAc) in EtOAc, affording the (5S)-7-methyl-2-[4-methyl-6-[4-(trifluoromethyl)phenyl]pyrimidin-2-yl]-1,7-diazaspiro[4.4]non-1-en-6-one (D15a) (2.51 g, 6.4626 mmol, 92.6% yield) as a light brown solid. The NMR was the same is as that for the R isomer produced in Description 15 but also contained traces of impurities.

Method 2:

Silver trifluoromethanesulphonate (9.39 g, 36.56 mmol) was added in a single batch to a solution of (3S)-3-amino-1-methyl-3-[3-[4-methyl-6-[4-(trifluoromethyl)phenyl]-pyrimidin-2-yl]prop-2-ynyl]pyrrolidin-2-one (which may be prepared as described in Description 14a) (71 g, 182.81 mmol) in MeCN (1000 mL) and the reaction was heated at 80° C. for 22 hours. The solvent was evaporated and the residue dissolved in DCM (1000 mL). Saturated $NaHCO_3$ (500 ml) and water (500 ml) were added and the mixture shaken. The phases were separated and the organic layer treated with a solution of cysteine (100 g, 825.35 mmol) in water (1500 ml). This mixture was stirred vigorously for 30 minutes. The mixture was filtered through a pad of celite, and the celite washed with DCM (2×100 ml). The phases were separated and the organic layer placed in a large beaker. To this was added a solution of cysteine (50 g, 412.68 mmol) in water (500 ml) and the mixture was stirred for a further 30 minutes. The phases were separated and the organic layer was washed with a mixture of sat. brine (500 ml) and water (500 ml). The organic layer was dried ($MgSO_4$) and the solvent evaporated to afford a dark brown foam. To the foam was added acetone (50 ml) and almost immediately a thick precipitate formed. This was swirled for about 5 minutes prior to slow addition of $Et_2O$ (150 ml) over approx. 10 minutes. After addition, the suspension was left to stand for 30 minutes. The solid was filtered off and washed with ether (3×30 ml) to afford the title material as a light brown solid (D15a) (49.24 g), pure by NMR and consistent with that produced by Method 1;

Optical Rotation α[D/20]=−141.5 (c=1.12 in $CHCl_3$).

The mother liquors were evaporated to afford a dark foam. This was dissolved in acetone (20 ml) and allowed to stand, with a seeding crystal, for about 15 minutes. Slow crystallization occurred. The mixture was diluted carefully with $Et_2O$ (40 ml) and left in a fridge for 18 hours. The supernatant was decanted and the crystalline solid washed with $Et_2O$ (3×6 ml) to afford an additional crop of (D15a) as a light orange solid (5.31 g) consistent spectroscopically with the earlier batch.

Description 16

2-Chloro-4-(5-ethoxy-2-fluoro-phenyl)-6-methyl-pyrimidine (D16)

To a solution of 2,4-dichloro-6-methyl-pyrimidine (2.66 g, 16.31 mmol) and (5-ethoxy-2-fluoro-phenyl)boronic acid (2 g, 10.87 mmol) in 1,2-dimethoxyethane (25 mL) and water (15 mL) was added sodium carbonate (3.46 g, 32.62 mmol). This was degassed with nitrogen for 5 minutes. Bis(triphenylphosphine)palladium (II) dichloride (0.38 g, 0.54 mmol) was then added and the reaction was heated to 80° C. overnight. The solvent was evaporated and the residue was partitioned between water (300 mL) and EtOAc (300 mL). The organics were washed with brine (100 mL), dried over $MgSO_4$ and concentrated in vacuo to afford a yellow oil. The material was purified using a Biotage SP4 eluting with 0 to 30% i-hexane/EtOAc and the product containing fractions were collected and the solvent evaporated to give a colourless solid (2.8 g) mainly 2-chloro-4-(5-ethoxy-2-fluoro-phenyl)-6-methyl-pyrimidine (D16)

300 MHz NMR $\delta_H$ ($CDCl_3$) 1.44 (3H, t), 2.60 (3H, s), 4.10 (2H, q), 6.98-7.20 (2H, m) 7.66-7.70 (2H, m)

Description 17

4-(5-Ethoxy-2-fluoro-phenyl)-2-iodo-6-methyl-pyrimidine (D17)

Hydroiodic acid (57% in water, 8 mL, 106.39 mmol) was added portionwise to 2-chloro-4-(5-ethoxy-2-fluoro-phenyl)-6-methyl-pyrimidine (which may be prepared as described in Description 16) (2.18 g, 8.17 mmol) in DCM (30 mL) at 20° C. and the dark mixture was stirred for 18 hrs. The mixture was filtered and washed with a little DCM. The yellow solid was suspended in water/DCM and quenched by the addition of satd. aq. $K_2CO_3$ (care: gas evolved). After basification, satd. aq. sodium metabisulphite was added and stirring was continued for 5 mins. The mixture was diluted with further DCM and the phases were separated. The organic layer was dried ($Na_2SO_4$) and the solvent evaporated to afford 4-(5-ethoxy-2-fluoro-phenyl)-2-iodo-6-methyl-pyrimidine (D17) (1.68 g, 4.6908 mmol, 57.4% yield) as a colourless oil.

300 MHz NMR $\delta_H$ ($CDCl_3$) 1.45 (3H, t), 2.55 (3H, s), 4.10 (2H, q), 6.96-7.12 (2H, m), 7.64-7.70 (2H, m).

Description 18 tert-Butyl N-[(3R)-3-[3-[4-(5-ethoxy-2-fluoro-phenyl)-6-methyl-pyrimidin-2-yl]prop-2-ynyl]-1-methyl-2-oxo-pyrrolidin-3-yl]carbamate (D18)

Copper iodide (26.27 mg, 0.14 mmol), followed by PdCl$_2$(Ph$_3$P)$_2$ (48.41 mg, 0.07 mmol) was added portionwise to a solution of the tert-butyl N-[(3R)-1-methyl-2-oxo-3-prop-2-ynyl-pyrrolidin-3-yl]carbamate (which may be prepared as described in Description 10) (348 mg, 1.38 mmol), 4-(5-ethoxy-2-fluoro-phenyl)-2-iodo-6-methyl-pyrimidine (which may be prepared as described in D17) (642.17 mg, 1.79 mmol) and Et$_2$NH (0.71 mL, 6.9 mmol) in THF (10 mL) under N$_2$ and the reaction was stirred at 20° C. for 18 hrs. The solvent was evaporated and the residue was dissolved in EtOAc and washed with water. The organic layer was dried (Na$_2$SO$_4$) and the solvent was evaporated to afford an oil. This was purified on a Biotage SP4 using a 25 g SNAP cartridge, eluting with 50 to 100% EtOAc/i-hexane affording the tert-butyl N-[(3R)-3-[3-[4-(5-ethoxy-2-fluoro-phenyl)-6-methyl-pyrimidin-2-yl]prop-2-ynyl]-1-methyl-2-oxo-pyrrolidin-3-yl]carbamate (D18) (605 mg, 1.2538 mmol, 90.9% yield) as a pale yellow foam.

300 MHz NMR $\delta_H$ (CDCl$_3$) 1.44 (3H, t), 1.45 (9H, s), 2.52-2.60 (1H, m), 2.58 (3H, s), 2.68-2.82 (2H, m), 2.98 (3H, s), 3.14 (1H, br.d), 3.42 (1H, br.t), 3.67 (1H, br.q), 4.07-4.14 (2H, abq), 5.34 (1H, br.s), 6.95-7.10 (1H, m), 7.10 (1H, t), 7.61-7.66 (2H, m).

Description 19

(3R)-3-Amino-3-[3-[4-(5-ethoxy-2-fluoro-phenyl)-6-methyl-pyrimidin-2-yl]prop-2-ynyl]-1-methyl-pyrrolidin-2-one (D19)

Trifluoroacetic acid (3 mL, 40.39 mmol) was added to a solution of tert-butyl N-[(3R)-3-[3-[4-(5-ethoxy-2-fluoro-phenyl)-6-methyl-pyrimidin-2-yl]prop-2-ynyl]-1-methyl-2-oxo-pyrrolidin-3-yl]carbamate (which may be prepared as described in Description 18) (605 mg, 1.25 mmol) in DCM (15 mL) at 20° C. and the reaction was stirred for 1 hour. Solid K$_2$CO$_3$ was added to quench the TFA present (care: gas evolved) and the resultant solid was filtered off and washed five times with DCM. The solvent was evaporated to give the (3R)-3-amino-3-[3-[4-(5-ethoxy-2-fluoro-phenyl)-6-methyl-pyrimidin-2-yl]prop-2-ynyl]-1-methyl-pyrrolidin-2-one (D19) (447 mg, 1.1688 mmol, 93.2% yield) as a yellow oil.

300 MHz NMR $\delta_H$ (CDCl$_3$) 1.45 (3H, t), 1.8 (2H,br.s), 2.04-2.14 (1H, m), 2.44-2.53 (1H, m), 2.59 (3H, s), 2.71-2.87 (2H, abq), 2.94 (3H, s), 34.6-3.53 (2H, m), 4.07-4.18 (2H, m), 6.96-7.01 (1H, s), 7.09 (1H, q), 7.61-7.67 (2H, d).

Description 20

(5R)-2-[4-(5-Ethoxy-2-fluoro-phenyl)-6-methyl-pyrimidin-2-yl]-7-methyl-1,7-diazaspiro[4.4]non-1-en-6-one (D20)

Silver trifluoromethanesulphonate (60.06 mg, 0.23 mmol) was added to a solution of (3R)-3-amino-3-[3-[4-(5-ethoxy-2-fluoro-phenyl)-6-methyl-pyrimidin-2-yl]prop-2-ynyl]-1-methyl-pyrrolidin-2-one (which may be prepared as described in Description 19) (447 mg, 1.17 mmol) in MeCN (20 mL) at 20° C. and the reaction was stirred for 66 hrs. An additional 10 mol % AgOTf was added, stirring was continued for an additional 3 days then the mixture was heated to 40° C. until no starting material remained. The solvent was evaporated and the residue was partitioned between water and EtOAc. The organic layer was dried (Na$_2$SO$_4$) and the solvent was evaporated to afford a brown oil. This was purified using a Biotage Isolera with a 25 g SNAP cartridge, eluting with a 0 to 50% mixture (9% MeOH; 89% EtOAc and 2% 880 NH$_3$) in EtOAc affording the (5R)-2-[4-(5-ethoxy-2-fluoro-phenyl)-6-methyl-pyrimidin-2-yl]-7-methyl-1,7-diazaspiro[4.4]non-1-en-6-one (D20) (335 mg, 0.876 mmol, 74.9% yield) as a light brown solid.

300 MHz NMR $\delta_H$ (CDCl$_3$) 1.46 (3H, t), 1.86-1.97 (1H, m), 2.13-2.24 (1H, m), 2.58-2.72 (2H, m), 2.69 (3H, s), 2.94 (3H, s), 3.28-3.42 (2H, m), 3.54-3.66 (1H, m), 3.72-3.79 (1H, m), 4.10 (2H, q), 6.96-7.20 (1H, m), 7.11 (1H, t), 7.74-7.78 (2H, m).

Description 21

3-(Benzhydrylideneamino)piperidin-2-one (D21)

Benzophenone imine (3 mL, 17.87 mmol) was added to a solution of 3-aminopiperidin-2-one [CAS 1892-22-4] (2 g, 17.52 mmol) and molecular sieves in DCE (50 mL) under nitrogen and the reaction was warmed to 80° C. for 18 hours. The solvent was evaporated and the residue applied to a 100 g SNAP column, eluting with 50 to 100% EtOAc/ihexane to afford 3-(benzhydrylideneamino)-piperidin-2-one (D21) (3.84 g, 13.796 mmol, 78.7% yield) as a colourless solid.

300 MHz NMR $\delta_H$ (CDCl$_3$) 1.65-1.80 (1H, m), 1.82-1.92 (1H, m), 2.01-2.13 (2H, m), 3.28-3.36 (1H, m), 3.42-3.51 (1H, m), 4.06 (1H, dd), 5.89 (1H, br.s), 7.30-7.50 (8H, m), 7.63-7.77 (2H, m).

Description 22

3-(Benzhydrylideneamino)-1-(2-trimethylsilylethoxymethyl)piperidin-2-one (D22)

KO$^t$Bu 1.7M in THF (8 mL, 13.59 mmol) was added dropwise over approx. 30 mins (using a syringe pump) to a solution of the 3-(benzhydrylideneamino)piperidin-2-one (which may be prepared as described in Description 21) (3.44 g, 12.36 mmol) in THF (100 mL) at 0° C. under nitrogen and the reaction was stirred at 0° C. for a further 10 mins. To the now orange/red solution was added the SEM-Cl (2.62 mL, 14.83 mmol) over 2 minutes and stirring was continued for 1 hr. The reaction was quenched by the addition of satd. aq. NaHCO$_3$ and EtOAC was added. The phases were separated and the organic layer was dried (Na$_2$SO$_4$) and the solvent evaporated to give an oil. This was purified using a Biotage SP4 with a 100 g SNAP cartridge, eluting with 0 to 100% EtOAc/i-hexane to afford the 3-(benzhydrylideneamino)-1-(2-trimethylsilylethoxy-methyl)piperidin-2-one (D22) (2.34 g, 5.7267 mmol, 46.3% yield) as a pale yellow oil.

300 MHz NMR $\delta_H$ (CDCl$_3$) 0.02 (9H, br.s), 0.87-1.02 (2H, m), 1.70-1.94 (2H, m), 2.00-2.21, (2H, m), 3.39-3.63 (4H, m), 4.09 (1H, dd), 4.75, 5.00 (2H, 2xd), 7.30-7.50 (8H, m), 7.71-7.69 (2H, m).

Description 23

3-(Benzhydrylideneamino)-3-prop-2-ynyl-1-(2-trimethylsilylethoxymethyl)piperidin-2-one (D23)

KO$^t$Bu 1.7M in THF (4.32 mL, 7.34 mmol) was added dropwise to a solution of 3-(benzhydrylideneamino)-1-(2- trimethylsilylethoxymethyl)piperidin-2-one (which may be prepared as described in Description 22) (2.5 g, 6.12 mmol) and propargyl bromide 80 wt % in toluene (0.95 mL, 8.57 mmol) in THF (100 mL) at 0° C. under $N_2$. The reaction was stirred for 40 mins. The reaction was quenched by the addition of satd. aq. $NaHCO_3$ and then diluted with EtOAc. The phases were separated, the organic layer was dried ($Na_2SO_4$) and the solvent was evaporated to afford an oil. The material was purified by SP4, 100 g SNAP, 0 to 50% EtOAc/i-hexane to afford product: 3-(benzhydrylideneamino)-3-prop-2-ynyl-1-(2-trimethylsilylethoxymethyl)-piperidin-2-one (D23) (897 mg, 2.0082 mmol, 32.8% yield) as a pale yellow oil.

300 MHz NMR $\delta_H$ (CDCl$_3$) −0.02 (9H, s), 0.77-0.97 (2H, m), 1.84-2.11 (4H, m), 2.46-2.55 (1H, m), 2.69-2.77 (1H, m), 2.91 (2H, dt), 3.28-3.57 (4H, m), 4.90 (1H, d), 7.20-7.41 (8H, m), 7.55-7.59 (2H, m).

In addition 940 mg, 38% of starting material was recovered.

Description 24

(3S)-3-Amino-3-prop-2-ynyl-1-(2-trimethylsilylethoxymethyl)piperidin-2-one (D24S) and (3R)-3-Amino-3-prop-2-ynyl-1-(2-trimethylsilylethoxymethyl)-piperidin-2-one (D24R)

Citric acid monohydrate (1.58 g, 7.5 mmol) was added to a solution of 3-(benzhydrylideneamino)-3-prop-2-ynyl-1-(2-trimethylsilylethoxymethyl)piperidin-2-one (which may be prepared as described in Description 23) (1.34 g, 3 mmol) in THF (30 mL) at 20° C. and the reaction was stirred for 5 days. The solution was evaporated and loaded onto an SCX cartridge (10 g) then eluted with MeOH, followed by 2M $NH_3$ in MeOH. The fractions containing the desired product were collected and evaporated to afford 3-amino-3-prop-2-ynyl-1-(2-trimethylsilylethoxymethyl)piperidin-2-one (658 mg, 2.3296 mmol, 77.7% yield) as a yellow oil.

300 MHz NMR $\delta_H$ (CDCl$_3$) 0.01 (9H, s), 0.94 (2H, t), 1.75-2.09 (6H, m), 2.27-2.25 (1H, m), 2.62 (2H, dq), 3.42, 3.55 (4H, 2×t), 4.74, 4.97 (2H, 2×d).

This material was separated by chiral HPLC: AD-H (semi-prep) using 15% EtOH/Heptane over 15 mins;

Fast isomer (retention time approx. 7.5 mins) assigned: (3R)-3-amino-3-prop-2-ynyl-1-(2-trimethylsilylethoxymethyl)-piperidin-2-one (254 mg) (D24R).

Slow isomer (retention time approx. 9 mins) assigned: (3S)-3-amino-3-prop-2-ynyl-1-(2-trimethylsilylethoxymethyl)-piperidin-2-one (239 mg) (D24S).

Description 25 tert-Butyl N-[(3S)-2-oxo-3-prop-2-ynyl-1-(2-trimethylsilylethoxymethyl)-3-piperidyl]carbamate (D25)

Boc$_2$O (221.61 mg, 1.02 mmol) was added to a solution of (3S)-3-amino-3-prop-2-ynyl-1-(2-trimethylsilylethoxymethyl)piperidin-2-one (which may be prepared as described in Description 24) (239 mg, 0.85 mmol) in DCM (10 mL) at 20° C. and the reaction was stirred for 18 hrs. Washed with water, sat. NaHCO$_3$, dried (Na$_2$SO$_4$) and the solvent evaporated to afford the tert-butyl N-[(3S)-2-oxo-3-prop-2-ynyl-1-(2-trimethylsilylethoxymethyl)-3-piperidyl]carbamate (D25) (330 mg, 0.8626 mmol) as a pale yellow oil.

300 MHz NMR $\delta_H$ (CDCl$_3$) 0.02 (9H, s), 0.91-0.98 (2H, m), 1.44 (9H, s), 1.83-1.85 (2H, m), 2.13 (1H, t), 2.28-3.37 (1H, m), 2.45-2.55 (1H, m), 2.78 (2H, dq), 3.34-3.68 (4H, m), 4.33, 4.42 (2H, 2×d), 5.27 (1H, br.s).

Description 26 tert-Butyl N-[(3S)-3-[3-[4-(5-ethoxy-2-fluoro-phenyl)-6-methyl-pyrimidin-2-yl]prop-2-ynyl]-2-oxo-1-(2-trimethylsilylethoxymethyl)-3-piperidyl]carbamate (D26)

Copper iodide (17.27 mg, 0.09 mmol), followed by PdCl$_2$(Ph$_3$P)$_2$ (31.83 mg, 0.05 mmol) was added portionwise to a solution of 4-(5-ethoxy-2-fluoro-phenyl)-2-iodo-6-methyl-pyrimidine (which may be prepared as described in Description 17) (389.81 mg, 1.09 mmol), tert-butyl N-[(3S)-2-oxo-3-prop-2-ynyl-1-(2-trimethylsilylethoxymethyl)-3-piperidyl]carbamate (which may be prepared as described in D25) (347 mg, 0.9100 mmol) and Et$_2$NH (0.47 mL, 4.54 mmol) in THF (10 mL) under N$_2$ and the reaction was stirred at 20° C. for 90 hrs. The solvent was evaporated and the residue was purified using a Biotage SP4 with a 25 g SNAP cartridge, eluting with 0 to 50% EtOAc/i-hexane affording the tert-butyl N-[(3S)-3-[3-[4-(5-ethoxy-2-fluoro-phenyl)-6-methyl-pyrimidin-2-yl]prop-2-ynyl]-2-oxo-1-(2-trimethylsilylethoxymethyl)-3-piperidyl]carbamate (D26) (397 mg, 0.6478 mmol, 71.4% yield) as a dark yellow oil.

300 MHz NMR $\delta_H$ (CDCl$_3$) 0.02 (9H, m), 0.89-0.97 (2H, m), 1.39-1.48 (12H, m), 1.89-1.99 (2H, m), 2.43-2.63 (5H, m), 2.98 (1H, d), 3.39-3.70 (5H, m), 4.11 (2H, q), 4.83-4.97 (2H, m), 5.39 (1H, br.s), 6.96-7.14 (2H, m), 7.63-7.68 (2H, m).

Description 27

(3S)-3-Amino-3-[3-[4-(5-ethoxy-2-fluoro-phenyl)-6-methyl-pyrimidin-2yl]prop-2-ynyl]-1-(hydroxymethyl)piperidin-2-one (D27)

Trifluoroacetic acid (2 mL, 26.92 mmol) was added to a solution of the tert-butyl N-[(3S)-3-[3-[4-(5-ethoxy-2-fluoro-phenyl)-6-methyl-pyrimidin-2-yl]prop-2-ynyl]-2-oxo-1-(2-trimethylsilylethoxymethyl)-3-piperidyl]carbamate (which may be prepared as described in Description 26) (345 mg, 0.56 mmol) in DCM (10 mL) at 20° C. and the reaction was stirred for 18 hrs. The reaction was quenched by the addition of solid K$_2$CO$_3$ and stirred for 5 mins. This mixture was diluted with DCM and water and the phases were separated. The organic layer was dried (Na$_2$SO$_4$) and the solvent evaporated to afford an amber solid (253 mg). The material was dissolved in MeOH and 0.880 NH$_3$ was added. This mixture was stirred for 3 days. The solvent was evaporated and the residue applied to an SCX (5 g) cartridge, eluting with MeOH followed by 2% aq. NH$_3$ in MeOH (product eluted). The solvent was evaporated to afford an amber glass (173 mg). An LCMS analysis indicated that there were two major components, the slower eluting component being (3S)-3-amino-3-[3-[4-(5-ethoxy-2-fluoro-phenyl)-6-methyl-pyrimidin-2yl]prop-2-ynyl]-1-(hydroxymethyl)piperidin-2-one (D27) and the faster (3S)-3-amino-3-[3-[4-(5-ethoxy-2-fluoro-phenyl)-6-methyl-pyrimidin-2-yl]prop-2-ynyl]-1-(hydroxymethyl)piperidin-2-one. This crude material was used in the next step.

Fast component m/z: 414 (70%, M+H$^+$), 404, 383, 367 (100%)

Slow component (D27) m/z: 383 (100%, M+H$^+$)

Description 28

(6S)-2-[4-(5-Ethoxy-2-fluoro-phenyl)-6-methyl-pyrimidin-2-yl]-1,8-diazaspiro[4.5]dec-1-en-7-one (D28)

Silver trifluoromethanesulphonate (10.78 mg, 0.040 mmol) was added to a mixture of (3S)-3-amino-3-[3-[4-(5-ethoxy-2-fluoro-phenyl)-6-methyl-pyrimidin-2-yl]prop-2-ynyl]-1-(hydroxymethyl)-piperidin-2-one (173 .mg, 0.4200 mmol) and (3S)-3-amino-3-[3-[4-(5-ethoxy-2-fluoro-phenyl)-6-methyl-pyrimidin-2-yl]prop-2-ynyl]piperidin-2-one (which may be prepared as described in Description 27) (173 mg) in MeCN (10 mL) and the reaction was stirred at 40° C. for 18 hrs. The solvent was evaporated and the residue was partitioned between water/CHCl$_3$. The organic layer was collected, dried (Na$_2$SO$_4$) and the solvent evaporated to afford a purple oil. This was purified using a Biotage Isolera equipped with a 25 g SNAP cartridge, eluting with 0 to 50% (89% EtOAc/9% MeOH/2% 0.880 NH$_3$)/EtOAc to afford (6S)-2-[4-(5-ethoxy-2-fluoro-phenyl)-6-methyl-pyrimidin-2-yl]-1,8-diazaspiro[4.5]dec-1-en-7-one (D28) as a light brown oil.

300 MHz NMR $\delta_H$ (CDCl$_3$) 1.46 (3H, t), 1.81-2.09 (4H, m), 2.26-2.45 (2H, m), 2.69 (3H, s), 3.29-3.69 (4H, m), 4.10 (2H, q), 5.72 (1H, br.s), 6.95-7.01 (1H, m), 7.12 (1H, t), 7.72-7.79 (2H, m).

Description 29

Methyl 4-methyl-6-[4-(trifluoromethyl)phenyl]pyrimidine-2-carboxylate (D29)

Concentrated aq. hydrochloric acid (42 mL, 491.4 mmol) was added to a stirred suspension of 4-methyl-6-[4-(trifluoromethyl)phenyl]pyrimidine-2-carbonitrile [CAS: 951232-17-0] (8.3 g, 31.53 mmol) in methanol (248 mL). The stirred mixture was heated at block temperature of 80° C. for 20 h. The reaction mixture was cooled to ambient temperature, diluted with DCM (500 ml) and Na$_2$CO$_3$ solid was added with stirring. Water (500 ml) was added and the mixture transferred to a separating funnel and shaken (aqueous phase had pH10). The aq. phase was re-extracted with DCM (200 ml) and the combined organic layers were dried (Na$_2$SO$_4$) and evaporated to an oil which solidified, to give 7.6 g after drying. This was dissolved in DCM (30 ml) and the solution was applied to a 340 g silica cartridge which was then eluted on a Biotage SP4 system with a gradient of EtOAc/iso-hexane from 0-75% to give methyl 4-methyl-6-[4-(trifluoromethyl)phenyl]pyrimidine-2-carboxylate (D29) (6.1 g, approximately 94% pure, contaminated with decarboxylated material);

300 MHz NMR $\delta_H$(CDCl$_3$) 2.76 (3H, s), 4.10 (3H, s), 7.76 (1H, s), 7.80 (2H, d), 8.28 (2H, d).

Description 30

4-Methyl-6-[4-(trifluoromethyl)phenyl]pyrimidine-2-carbaldehyde (D30)

To a solution of methyl 4-methyl-6-[4-(trifluoromethyl)phenyl]pyrimidine-2-carboxylate (which may be prepared by the method described in Description 29) (6.1 g, 20.59 mmol) in dry THF (120 mL) cooled to −75° C. was added diisobutylaluminium hydride (1M in toluene) (41.18 mL, 41.18 mmol) drop-wise over 10 minutes. The solution was stirred at the same temperature for 1.75 h then EtOH (0.96 ml) was added. After 1 minute the reaction mixture was poured into saturated Rochelle salt solution, (250 ml) and water (250 ml). EtOAc (250 ml) was added and the mixture stirred vigorously for 0.5 h then filtered under suction through celite. The filtrate was transferred to a separating funnel and the layers separated. The aqueous fraction was further extracted with EtOAc (200 ml) and the combined organic extracts were dried (MgSO$_4$) and evaporated to a pale yellow, sticky solid. This was stirred with iso-hexane (30 ml) for 5 minutes then sonicated for 5 minutes. It was filtered, washed with iso-hexane (10 ml) and dried at RT under vacuum for 2 hours to give 4-methyl-6-[4-(trifluoromethyl)phenyl]pyrimidine-2-carbaldehyde (D30) (4.66 g);

Analytical LCMS showed 2 peaks at 2.03 and 2.65 minutes, both with m/z=267 (M+H$^+$): which correspond to the eluting aldehyde hydrate;

300 MHz NMR $\delta_H$(CDCl$_3$) 2.78 (3H, s), 7.79 (1H, s), 7.82 (2H, d), 8.32 (2H, d), 10.20 (1H, s).

Description 31

2-[4-Methyl-6-[4-(trifluoromethyl)phenyl]pyrimidin-2-yl]-1,7-diazaspiro[4.4]non-1-en-6-one (D31)

3A Molecular sieves (10 g, 5.63 mmol) were dried under vacuum then treated with a solution of 4-methyl-6-[4-(trifluoromethyl)phenyl]pyrimidine-2-carbaldehyde (which may be prepared as described in Description 30) (1.5 g, 5.63 mmol) in dry DCM (45 mL), added under nitrogen, followed by 3-aminopyrrolidin-2-one (564.12 mg, 5.63 mmol). The mixture was gently stirred under N$_2$ at ambient temp for 4 h. The reaction mixture was filtered through celite under suction and washed with DCM (5×20 ml). The filtrate was evaporated to an almost colourless oil which was dissolved in dry THF (60 mL) placed under nitrogen and treated with phenyl vinyl sulfone (947.7 mg, 5.6 mmol) then silver acetate (940.4 mg, 5.6 mmol). The mixture was wrapped in foil, stirred at ambient temperature for 3 minutes, then DBU (0.84 mL, 5.63 mmol) was added dropwise over a further 3 minutes and the mixture left to stir for 22 h. The reaction mixture was filtered through celite and washed through with THF (5×20 ml). The filtrate was evaporated to a dark residue, dried then dissolved in DCM (20 ml) and was applied to a 100 g silica cartridge which was initially eluted on a Biotage SP4 system with a gradient of methanol in ethyl acetate, then finally with 1M NH$_3$-MeOH:EtOAc 1:9 to give 2-[4-methyl-6-[4-(trifluoromethyl)-phenyl]-pyrimidin-2-yl]-1,7-diazaspiro[4.4]non-1-en-6-one (D31) (774 mg);

300 MHz NMR $\delta_H$ (CDCl$_3$) 1.98 (1H, m), 2.30 (1H, m), 2.60-2.84 (2H, m), 2.73 (3H, s), 3.33-3.48 (2H, m), 3.59 (1H, m), 3.75 (1H, q), 6.0 (1H, br.s), 7.64 (1H, s), 7.79 (2H, d), 8.27 (2H, d).

Description 32

2-(Benzyloxycarbonylamino)-2-methyl-propanoic acid (D32)

To a solution of 2-amino-2-methyl-propanoic acid (10 g, 96.97 mmol) in water (75 mL) was added triethylamine (13.48 mL, 96.97 mmol) followed by the dropwise addition of a solution of benzyl (2,5-dioxopyrrolidin-1-yl) carbonate (24.17 g, 96.97 mmol) in MeCN (30 mL). The pH was monitored during the addition and afterwards was adjusted with triethylamine (1.5 mL) from pH 7 to 8. The mixture was stirred at room temperature overnight. The reaction mixture was concentrated by removal of MeCN. To the aqueous was added saturated aqueous sodium bicarbonate (2 mL) which gave a suspension. This was filtered and the solid kept to one side. The filtrate was extracted with ether (three times). The aqueous phase was acidified to pH 3 with approximately 1 M aqueous potassium bisulphate and then extracted into EtOAc (three times). The combined EtOAc extracts were dried over magnesium sulphate, filtered and evaporated to yield 2-(benzyloxycarbonylamino)-2-methyl-propanoic acid (D32) as a waxy white solid, (18.001 g);

300 MHz $^1$H NMR $\delta_H$ (CDCl$_3$) 1.60 (6H, s), 5.1 (2H, s), 5.4 (1H, br s), 7.35-7.42 (5H, m), 8.9 (1H, br s).

Description 33

Ethyl 2-(benzyloxycarbonylamino)-2-methyl-propanoate (D33)

To a solution of 2-(benzyloxycarbonylamino)-2-methyl-propanoic acid (which may be prepared as described in Description 32) (5000 mg, 21.08 mmol) in toluene (50 mL) was added ethanol (5 mL) and p-toluenesulfonic acid (400.89 mg, 2.11 mmol). The solution was stirred at 80° C. overnight. The reaction mixture was evaporated and the residues dissolved in EtOAc and washed with saturated aqueous sodium bicarbonate. The aqueous phase was back extracted into EtOAc. The combined organics were dried over magnesium sulphate, filtered and evaporated to yield the title compound (D33) as a light yellow oil (4.667 g);

300 MHz $^1$H NMR $\delta_H$ (CDCl$_3$) 1.27 (3H, q), 1.60 (6H, s), 4.19 (2H, t), 5.11 (2H, s), 5.4 (1H, br s), 7.38 (5H, s).

Description 34

Benzyl N-(1,1-dimethyl-2-oxo-ethyl)carbamate (D34)

To a solution of ethyl 2-(benzyloxycarbonylamino)-2-methyl-propanoate (which may be prepared as described in Description 33) (4667 mg, 17.59 mmol) in toluene (100 mL) cooled to −78° C. was added diisobutyl aluminium hydride (1 M in toluene) (61.57 mL, 61.57 mmol) as a thin stream over approximately 2 minutes. The mixture was stirred at −78° C. over 30 minutes then allowed to warm to 0° C. and stirred over 1.5 hours. The reaction mixture was quenched by addition of a saturated solution of Rochelle's salt. The quenched mixture was stirred over 1 hour, then extracted into ether (3 times). The combined ethereal extracts were dried over magnesium sulphate, filtered and evaporated to a clear oil. The oil was dissolved in DCM (60 mL) and 4A molecular sieves (4 g) and pyridinium dichromate (16544.34 mg, 43.98 mmol) were added and the mixture stirred at room temperature overnight. The reaction mixture was filtered over kieselguhr and the filtrate evaporated to a dark brown oil. Purification by silica gel column chromatography (20% EtOAc in isohexane) yielded benzyl N-(1,1-dimethyl-2-oxo-ethyl)carbamate (D34) (1840 mg, 8.3164 mmol, 47.3% yield) as a clear oil;

300 MHz $^1$H NMR $\delta_H$ (CDCl$_3$) 1.40 (6H, s), 5.11 (2H, s), 5.3 (1H, br s), 7.35-7.45 (5H, m), 9.43 (1H, s).

Description 35

Methyl 4-(benzyloxycarbonylamino)-2-(tert-butoxycarbonylamino)-4-methyl-pent-2-enoate (D35)

To a solution of benzyl N-(1,1-dimethyl-2-oxo-ethyl)carbamate (which may be prepared as described in Description 34) (1740 mg, 7.86 mmol) in DCM (70 mL) was added methyl 2-(tert-butoxycarbonylamino)-2-dimethoxyphosphoryl-acetate (4675.23 mg, 15.73 mmol) and DBU (2.35 mL, 15.73 mmol). The solution was stirred at room temperature overnight. The reaction mixture was quenched with saturated aqueous ammonium chloride and extracted into DCM. The combined extracts were passed over a hydrophobic frit to yield a pale yellow oil (4.843 g). Purification by silica gel column chromatography (0-100% EtOAc in iso-hexane) yielded methyl 4-(benzyloxycarbonylamino)-2-(tert-butoxycarbonylamino)-4-methyl-pent-2-enoate (D35) (2499 mg, 6.3677 mmol, 81% yield) as a clear oil;

300 MHz $^1$H NMR $\delta_H$ (CDCl$_3$) 1.44 (9H, s), 1.56 (6H, s), 3.78 (3H, s), 5.07 (3H, s), 6.70 (1H, br s), 6.60 (1H, br s), 7.37 (5H, br s).

Description 36 tert-Butyl N-(5,5-dimethyl-2-oxo-pyrrolidin-3-yl) carbamate (D36)

A solution of methyl 4-(benzyloxycarbonylamino)-2-(tert-butoxycarbonylamino)-4-methyl-pent-2-enoate (which may be prepared as described in Description 35) (2499 mg, 6.37 mmol) in methanol (125 mL) was passed over a 10% Pd/C cartridge on an H-Cube under full hydrogen flow at 25° C. The methanol solution evaporated to give tert-butyl N-(5,5-dimethyl-2-oxo-pyrrolidin-3-yl)carbamate (D36) (1307 mg, 5.7252 mmol, 89.9% yield);

300 MHz $^1$H NMR $\delta_H$ (CDCl$_3$) 1.29, 1.33, (6H, 2s), 1.45 (9H, s), 1.67-1.82 (2H, m), 2.60 (1H, br t), 4.35 (1H, br s), 6.1 (1H, br s).

Description 37

3-Amino-5,5-dimethyl-pyrrolidin-2-one hydrochloride (D37)

To a solution of tert-butyl N-(5,5-dimethyl-2-oxo-pyrrolidin-3-yl)carbamate (which may be prepared as described in Description 36) (1307 mg, 5.73 mmol) in DCM (5 mL) was added 4 M HCl in dioxane (2.86 mL, 11.45 mmol). The solution (which immediately started to evolve gas) was stirred at room temperature over 1 hour. The reaction mixture heavily precipitated. It was diluted with ether (approximately 50 mL) and the solid filtered under vacuum, washed with ether and dried in the vacuum oven to afford 3-amino-5,5-dimethyl-pyrrolidin-2-one hydrochloride (D37) (917 mg, 5.5701 mmol, 97.3% yield) as a white solid;

300 MHz $^1$H NMR $\delta_H$ (DMSO) 1.20, 1.25 (6H, 2s), 1.82 (1H, t), 2.28 (1H, dd), 4.07 (1H, br s), 8.5 (4H, br s).

Description 38

(5S)-8,8-Dimethyl-2-[4-methyl-6-[4-(trifluoromethyl)phenyl]pyrimidin-2-yl]-1,7-diazaspiro[4.4]non-1-en-6-one (D38S) and (5R)-8,8-Dimethyl-2-[4-methyl-6-[4-(trifluoromethyl)phenyl]pyrimidin-2-yl]-1,7-diazaspiro[4.4]non-1-en-6-one (D38R)

To a solution of 4-methyl-6-[4-(trifluoromethyl)phenyl]pyrimidine-2-carbaldehyde (which may be prepared as described in Description 30) (100 mg, 0.3800 mmol) in toluene (4 mL) was added phenyl vinyl sulfone (63.18 mg, 0.3800 mmol), triethylamine (0.1 mL, 0.7500 mmol) and 3-amino-5,5-dimethyl-pyrrolidin-2-one hydrochloride (which may be prepared as described in Description 37) (61.84 mg, 0.3800 mmol). The mixture was stirred at 100° C. for 25 minutes then allowed to cool. The reaction mixture was evaporated and the residues dissolved in DCM (20 ml) and washed with water (20 ml), dried over (Na$_2$SO$_4$), filtered and evaporated to give an orange oil. To a solution of this material in THF (4 mL) was added DBU (0.06 mL, 0.3800 mmol) at ambient temp under N$_2$ followed by silver acetate (62.69 mg, 0.3800 mmol). The solution was stirred at ambient temp under N$_2$ for approx. 60 hours then filtered under suction through celite and washed through with THF (3×3 ml). The filtrate was evaporated to an oil, which was purified by chromatography on a 10 g silica cartridge eluted on a Biotage SP4 system with a gradient of methanolic ammonia in ethyl acetate to give a racemic mixture of the title materials as a slightly coloured foam;

300 MHz $^1$H NMR $\delta_H$ (CDCl$_3$) 1.40 (3H, s), 1.50 (3H, s), 2.03 (1H, m), 2.18 (1H, d), 2.78 (1H, m), 2.72 (3H, s), 2.87 (1H, d), 3.38 (1H, ddd), 3.57 (1H, m), 5.70 (1H, br.s), 7.63 (1H, s), 7.79 (2H, d), 8.27 (2H, d).

This was separated on an IA ChiralPak preparative column eluting with ethanol in heptanes to give a faster running isomer (5R)-8,8-dimethyl-2-[4-methyl-6-[4-(trifluoromethyl)phenyl]-pyrimidin-2-yl]-1,7-diazaspiro[4.4]non-1-en-6-one (D38R) (65 mg);

m/z 403 (M+H$^+$); Optical Rotation α[D/20]=+60.0 (c=0.9, CHCl$_3$).

Also a slower eluting component (5S)-8,8-dimethyl-2-[4-methyl-6-[4-(trifluoromethyl)phenyl]-pyrimidin-2-yl]-1,7-diazaspiro[4.4]non-1-en-6-one (D38S) (65 mg);

m/z 403 (M+H$^+$); Optical Rotation α[D/20]=−69.0 deg (c=0.9, CHCl$_3$).

PREPARATION OF EXAMPLES

Examples 1, 2

(2R,5S)-7-Methyl-2-[4-[4-(trifluoromethyl)phenyl]pyrimidin-2-yl]-1,7-diazaspiro[4.4]nonan-6-one hydrochloride (E1) and (2S,5S)-7-Methyl-2-[4-[4-(trifluoromethyl)phenyl]pyrimidin-2-yl]-1,7-diazaspiro[4.4]nonan-6-one hydrochloride (E2)

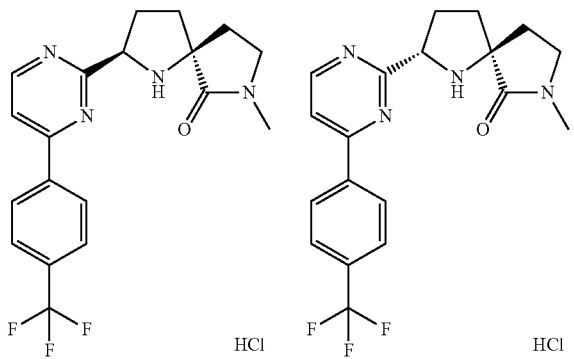

Concentrated aq. HCl (71.99 μL, 0.84 mmol) was added to a solution of (5S)-7-methyl-2-[4-[4-(trifluoromethyl)phenyl]pyrimidin-2-yl]-1,7-diazaspiro[4.4]non-1-en-6-one (which may be prepared as described in Description 9) (314 mg, 0.84 mmol) in DCM (10 mL) at 0° C. Sodium triacetoxyborohydride (533.3 mg, 2.52 mmol) was added in a single portion and the resulting mixture was stirred allowing warming to room temperature. After 90 minutes the reaction was quenched by the addition of sat. aq. Na$_2$CO$_3$ and the resultant mixture was filtered. The phases were separated, the organic layer was dried (Na$_2$SO$_4$) and the solvent was evaporated to afford a brown oil. This was purified using a Biotage SP4 with a 25 g SNAP cartridge, eluting with 0 to 20% MeOH in EtOAc. This gave two products; the first to elute: (2R,5S)-7-methyl-2-[4-[4-(trifluoromethyl)phenyl]pyrimidin-2-yl]-1,7-diazaspiro[4.4]nonan-6-one (68 mg, 0.1807 mmol, 21.5% yield) was obtained as a yellow oil.

TLC (10% MeOH/EtOAc): Rf=0.25;

300 MHz NMR $\delta_H$ (CDCl$_3$) 1.6 (1H, br.s), 1.89-1.99 (1H, s), 2.10-2.32 (4H, m), 2.59-2.69 (1H, m), 2.93 (3H, s), 3.28-3.42 (2H, m), 4.39-4.45 (1H, m), 7.61, (1H, d), 7.79 (2H, d), 8.24 (2H, d), 8.82 (1H, d).

1M HCl in Et$_2$O (0.18 mL, 0.1800 mmol) was added to a solution of this material in DCM (1 mL) and the solution stood for one minute. The solvent was then blown off with a stream of nitrogen to afford the (2R,5S)-7-methyl-2-[4-[4-(trifluoromethyl)phenyl]pyrimidin-2-yl]-1,7-diazaspiro[4.4]nonan-6-one hydrochloride (E1) (72 mg, 0.19 mmol) an orange solid.

m/z: 377 (M+H$^+$)

The slower to elute material was obtained impure but was re-purified using chiral HPLC (AD-H), eluting with 20% EtOH/heptanes to afford (2S,5S)-7-methyl-2-[4-[4-(trifluoromethyl)-phenyl]-pyrimidin-2-yl]-1,7-diazaspiro[4.4]nonan-6-one (21 mg, 0.0558 mmol, 6.7% yield) as an off-white solid;

300 MHz NMR $\delta_H$ (CDCl$_3$) 1.82-1.91 (1H, m), 2.05-2.30 (4H, m), 2.47-2.57 (1H, m), 2.95 (3H, s), 3.30-3.46 (2H, m), 3.80 (1H, br.s), 4.58 (1H, t), 7.62 (1H, d), 7.79 (2H, d), 8.30 (2H, d), 8.83 (1H, d).

1M HCl in Et$_2$O (0.05 mL, 0.05 mmol) was added to a solution of a portion of this material (17 mg, 0.05 mmol) in DCM (1 mL) and the solution stood for one minute. The solvent was then blown off with a stream of nitrogen to afford the (2S,5S)-7-methyl-2-[4-[4-(trifluoromethyl)phenyl]pyrimidin-2-yl]-1,7-diazaspiro[4.4]nonan-6-one hydrochloride (E2) (19 mg, 0.0505 mmol) an off-white solid;

m/z: 377 (M+H$^+$).

Examples 3, 4

| Example Number | Structure | Name | Analysis | Method |
|---|---|---|---|---|
| E3 | 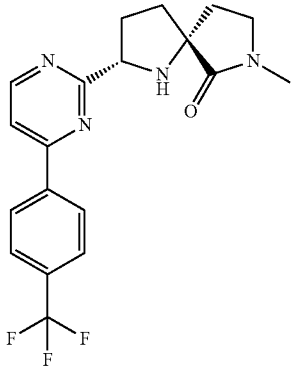 | (2S,5R)-7-Methyl-2-[4-[4-(trifluoromethyl)phenyl]pyrimidin-2-yl]-1,7-diazaspiro[4.4]nonan-6-one hydrochloride | m/z: 377 (M + H$^+$) | Using the method described for Example 1 but using D10 in place of D4 in Description 7 |

| Example Number | Structure | Name | Analysis | Method |
|---|---|---|---|---|
| E4 | 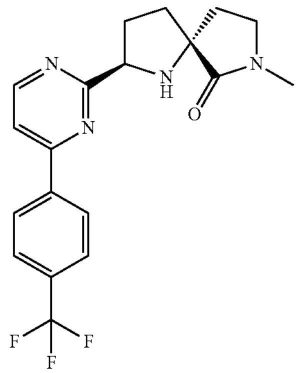 | (2R,5R)-7-Methyl-2-[4-[4-(trifluoromethyl)-phenyl]-pyrimidin-2-yl]-1,7-diazaspiro[4.4]nonan-6-one hydrochloride | m/z: 377 (M + H⁺) | Using the method described for Example 2 but using D10 in place of D4 in Description 7 |

Examples 5, 6

(2S,5R)-7-Methyl-2-[4-methyl-6-[4-(trifluoromethyl)phenyl]pyrimidin-2-yl]-1,7-diazaspiro[4.4]nonan-6-one hydrochloride (E5) and (2R,5R)-7-Methyl-2-[4-methyl-6-[4-(trifluoromethyl)phenyl]pyrimidin-2-yl]-1,7-diazaspiro[4.4]nonan-6-one hydrochloride (E6)

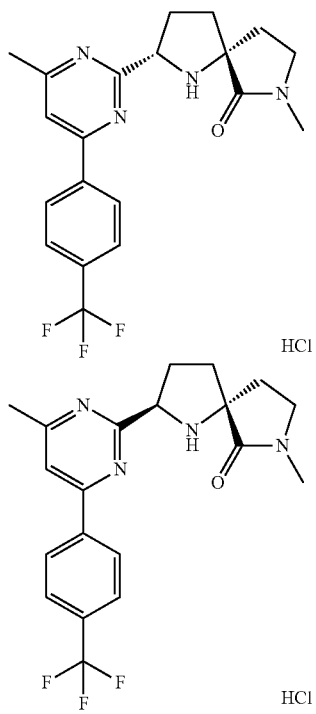

Concentrated aq. HCl (79.33 µL, 0.92 mmol) was added to a solution of (5R)-7-methyl-2-[4-methyl-6-[4-(trifluoromethyl)phenyl]pyrimidin-2-yl]-1,7-diazaspiro[4.4]non-1-en-6-one (which may be prepared as described in Description 15) (359 mg, 0.9200 mmol) in DCM (10 mL) at 0° C. Finally, sodium triacetoxyborohydride (587.71 mg, 2.77 mmol) was added in a single portion and the resulting mixture was stirred for 90 mins. The reaction was quenched by the addition of sat. aq. $Na_2CO_3$ and the resultant mixture was stirred for 5 mins. The phases were separated, the organic layer was dried ($Na_2SO_4$) and the solvent was evaporated to afford a brown oil. This material was purified using a Biotage SP4 with a 50 g SNAP cartridge eluting with 0 to 70% [MeOH/EtOAc/880 $NH_3$; 20:80:2] in EtOAc. With a partial separation the faster eluting anti isomer (2S,5R)-7-methyl-2-[4-methyl-6-[4-(trifluoromethyl)phenyl]pyrimidin-2-yl]-1,7-diazaspiro[4.4]nonan-6-one was isolated as a yellow oil (77 mg);

300 MHz NMR $\delta_H$ (CDCl₃) 1.86-1.97 (1H, m), 2.10-2.31 (4H, m), 2.59-2.68 (1H, m), 2.62 (3H, s), 2.92 (3H, s), 3.10 (1H br.s), 3.27-3.43 (2H, m), 4.85 (1H, t), 7.46 (1H, s), 7.77 (2H, d), 8.21 (2H, d).

A further sample of this material (181 mg, 0.46 mmol) was dissolved in DCM (2 mL) at 20° C. To this was added 1M HCl in ether (0.46 mL, 0.46 mmol) and the reaction was stood for 5 mins. The solvent was evaporated to afford the (2S,5R)-7-methyl-2-[4-methyl-6-[4-(trifluoromethyl)phenyl]-pyrimidin-2-yl]-1,7-diazaspiro[4.4]nonan-6-one hydrochlorde (E5) (176 mg) as a light brown solid;

m/z: 391 (M+H⁺).

Mixed fractions from the free base separation were collected and evaporated to afford a yellow oil (181 mg) and this material was separated by chiral HPLC (AD-H, semi-prep eluting with 50/50 heptane:EtOH) to afford the pure anti isomer (retention time approx. 8 mins) as a colourless oil and the cis isomer (2R,5R)-7-Methyl-2-[4-methyl-6-[4-(trifluoromethyl)phenyl]pyrimidin-2-yl]-1,7-diazaspiro[4.4]nonan-6-one as a pale yellow oil (19 mg);

300 MHz NMR $\delta_H$ (CDCl₃) 1.6 (1H, br.s), 1.81-1.93 (1H, m), 2.05-2.30 (4H, m), 2.45-2.55 (1H, m), 2.61 (3H, s), 2.95 (3H, s), 2.29-3.48 (2H, m), 4.52 (1H, t), 7.48 (1H, s), 7.78 (2H, d), 8.28 (2H, d).

This was dissolved in DCM (1 mL) at 20° C. and to this was added 1M HCl in ether (0.05 mL, 0.05 mmol) and the reaction was stood for 5 mins. The solvent was evaporated to afford the (2R,5R)-7-methyl-2-[4-methyl-6-[4-(trifluoromethyl)phenyl]pyrimidin-2-yl]-1,7-diazaspiro[4.4]nonan-6-one hydrochloride (E6) (19 mg, 0.0487 mmol) as a light brown solid;

m/z: 391 (M+H⁺).

Example 7

(2R,5S)-7-Methyl-2-[4-methyl-6-[4-(trifluoromethyl)-phenyl]pyrimidin-2-yl]-1,7-diazaspiro[4.4]nonan-6-one hydrochloride (E7)

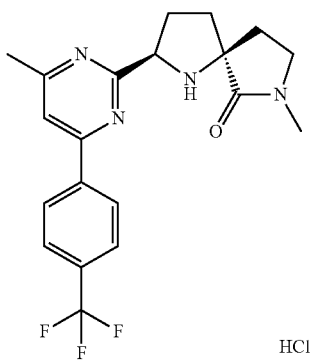

Concentrated aq. HCl (554.67 µL, 6.46 mmol) was added to a solution of the (5S)-8-methyl-3-[4-methyl-6-[4-(trifluoromethyl)phenyl]pyrimidin-2-yl]-4,8-diazaspiro[4.4]non-3-en-9-one (2.51 g, 6.46 mmol) (which may be prepared as described in Description 15a) in DCM (60 mL) at 0° C. Finally, Sodium triacetoxyborohydride (4.11 g, 19.39 mmol) was added in a single portion and the resulting mixture was stirred for 90 mins. The reaction was quenched by the addition of sat. aq. $Na_2CO_3$ and stirring was continued for 5 mins. The phases were separated, the organic layer was dried ($Na_2SO_4$) and the solvent was evaporated to afford an amber oil (2.15 g). This was dissolved in DCE (60 ml) and $Boc_2O$ (2.4 g, 11.01 mmol) was added and the reaction was stirred at 50° C. for 18 hrs. The solvent was evaporated to afford a crude brown oil. This was purified using a Biotage SP4 with a 100 g SNAP cartridge, eluting with EtOAc (8 CV) to elute the faster Syn isomer A, followed by 0 to 10% MeOH/EtOAc to elute the slower anti isomer B. The syn isomer A: tert-butyl (2S,5S)-7-methyl-2-[4-methyl-6-[4-(trifluoromethyl)phenyl]pyrimidin-2-yl]-6-oxo-1,7-diazaspiro[4.4]-nonane-1-carboxylate (0.6580 g, 1.3414 mmol, 24.4% yield) was obtained as a foam;

m/z 491 (M+H$^+$).

The anti isomer B: tert-butyl (2R,5S)-7-methyl-2-[4-methyl-6-[4-(trifluoromethyl)-phenyl]pyrimidin-2-yl]-6-oxo-1,7-diazaspiro[4.4]nonane-1-carboxylate (1.9 g, 3.8734 mmol, 70.3% yield), was obtained as a foam;

m/z 491 (M+H$^+$),

4M HCl in dioxane (9.68 mL, 38.73 mmol) was added to a solution of the anti isomer B, tert-butyl (2R,5S)-7-methyl-2-[4-methyl-6-[4-(trifluoromethyl)phenyl]pyrimidin-2-yl]-6-oxo-1,7-diazaspiro[4.4]nonane-1-carboxylate (1.9 g, 3.87 mmol) in DCM (20 mL) at 20° C. and the reaction stirred for 18 hrs. The solvent was evaporated and the residue was suspended in EtOAc. This was treated with sat. $NaHCO_3$ and the phases separated. The organic layer was dried ($Na_2SO_4$) and the solvent evaporated to afford a light brown oil (1.47 g). This material was dissolved in MeOH and applied to a SCX (10 g) cartridge. The column was eluted with MeOH, followed by 2M $NH_3$ in MeOH to afford the (2R,5S)-7-methyl-2-[4-methyl-6-[4-(trifluoromethyl)phenyl]pyrimidin-2-yl]-1,7-diazaspiro[4.4]nonan-6-one (1.2 g, 3.0738 mmol, 79.4% yield) as a light brown oil;

300 MHz NMR $\delta_H$ (CDCl$_3$) 1.86-1.97 (1H, m), 2.10-2.31 (4H, m), 2.59-2.68 (1H, m), 2.62 (3H, s), 2.92 (3H, s), 3.10 (1H br.s), 3.27-3.43 (2H, m), 4.85 (1H, t), 7.46 (1H, s), 7.77 (2H, d), 8.21 (2H, d).

1M HCl in Et$_2$O (3.07 mL, 3.07 mmol) was added to a solution of the (2R,5S)-7-methyl-2-[4-methyl-6-[4-(trifluoromethyl)phenyl]pyrimidin-2-yl]-1,7-diazaspiro[4.4]nonan-6-one (1.2 g, 3.07 mmol) in DCM (20 mL) at 20° C. and the reaction stirred for 5 mins. The solvent was evaporated and the residue was triturated from Et$_2$O and dried under vacuum at 40° C. to afford the (2R,5S)-7-methyl-2-[4-methyl-6-[4-(trifluoromethyl)phenyl]pyrimidin-2-yl]-1,7-diazaspiro[4.4]nonan-6-one hydrochloride (E7) (1.07 g, 2.7408 mmol, 89.2% yield) as an off white solid with 5 mol % ether present;

300 MHz NMR $\delta_H$ (MeOD) 2.26-2.57 (4H, m), 2.61-1.71 (1H, m), 2.69 (3H, s), 2.87-2.98 (1H, s), 2.98 (3H, s), 3.53-3.59 (2H, m), 5.84 (1H, t), 7.88 (2H, d), 8.02 (1H, s), 8.95 (2H, d);

m/z 391 (M+H$^+$); Optical Rotation α[D/20]=+12.1 (c=0.995, MeOH).

Example 7a

(2R,5S)-7-Methyl-2-[4-methyl-6-[4-(trifluoromethyl)-phenyl]pyrimidin-2-yl]-1,7-diazaspiro[4.4]nonan-6-one sulfuric acid salt (E7a)

(5S)-7-Methyl-2-[4-methyl-6-[4-(trifluoromethyl)phenyl]pyrimidin-2-yl]-1,7-diazaspiro[4.4]non-1-en-6-one (which may be prepared as described in Description 15a) (78.34 g, 201.7 mmol) was added to a 5 L three necked round bottomed flask containing an overhead stirrer, 500 ml pressure-equalising dropping funnel with a nitrogen inlet and thermometer. To this was added DCM (1000 mL) and the stirred mixture cooled to approx. −70° C. The dropping funnel was charged with a pre-sonicated solution of borane tert-butylamine (19.3 g, 221.87 mmol) in DCM (200 mL). The borane complex was added slowly maintaining the temperature below −70° C. over approx. 30 minutes. After addition the reaction was stirred at below −70° C. for 90 minutes. The dropping funnel was charged with 6M HCl (400 ml) and this was added dropwise over approx. 15 minutes. The reaction temperature warmed to −50° C. during the addition. After addition was complete the acetone/dry-ice bath was removed and the reaction mixture warmed to room temperature then stirred for a further 30 minutes. In a separate 10 L flask was added sodium carbonate (200 g) and water (1 L). To this flask was added an overhead stirrer. The reaction mixture was carefully added (note: gas evolution) to the sodium carbonate solution and stirring was maintained until gas evolution ceased. The mixture was transferred to a 6 L separating funnel and the phases were separated. The aqueous layer was washed with DCM (2×200 ml) and the combined organics were dried (MgSO$_4$). The solvent was evaporated to afford 7-methyl-2-[4-methyl-6-[4-(trifluoromethyl)-phenyl]pyrimidin-2-yl]-1,7-diazaspiro[4.4]nonan-6-one as an amber oil (77.8 g), a 96:4 ratio of (2R,5S) and (2S,5S) isomers.

A similarly prepared sample was recrystallised from diethyl ether and isohexane to give the free base form of the title material as a colorless solid with a melting point of 66-67° C. Similarly prepared 7-methyl-2-[4-methyl-6-[4-(trifluoromethyl)-phenyl]pyrimidin-2-yl]-1,7-diazaspiro[4.4]nonan-6-one with a diastereomeric excess of approximately 92% (49 g, 125.51 mmol) in MeCN (700 mL) was suction filtered through a shallow pad of Hyflo to give a clear yellow solution. To this rapidly stirred solution at 50° C. was added 7.5M sulphuric acid (17.6 mL, 132 mmol) over 5 seconds to give a solution which quickly crystallized. The mixture was left to stand at ambient temperature for 2 h then filtered and washed with acetonitrile/Et₂O (1:1) (200 ml) then Et₂O (150 ml) and dried 50° C. to give the title material (E7a) in an 82:1 ratio of (2R,5S) and (2S,5S) isomers (50.6 g) assessed by NMR.

300 MHz NMR $\delta_H$ (MeOD) 2.26-2.56 (4H, m), 2.64-2.74 (1H, m), 2.69 (3H, s), 2.88-2.98 (1H, m), 2.98 (3H, s), 3.53-3.59 (2H, m), 5.35 (1H, t), 7.78 (2H, d), 8.02 (1H, s), 8.46 (2H, d);

m/z 391 (M+H⁺).

A similarly prepared sample was recrystallised from acetonitrile to give the title compound as a cream solid with a melting point of 227-228° C.

Example 7b (2R,5S)-7-Methyl-2-[4-methyl-6-[4-(trifluoromethyl)-phenyl]pyrimidin-2-yl]-1,7-diazaspiro[4.4] nonan-6-one sulfuric acid salt hydrate (E7b)

(2R,5S)-7-Methyl-2-[4-methyl-6-[4-(trifluoromethyl)-phenyl]pyrimidin-2-yl]-1,7-diazaspiro[4.4]nonan-6-one sulfuric acid salt (which may be formed as described in Example 7a) (10 mg) was recrystallised by slow cooling in a dewer flask from hot acetone (2 ml), with sufficient added water to cause solubilisation, to form the title compound (E7b), the crystalline monohydrate. This was shown to have the (2R, 5S)-configuration by single crystal X-ray crystallography.

Examples 8, 9

(2S,5R)-2-[4-(5-Ethoxy-2-fluoro-phenyl)-6-methyl-pyrimidin-2-yl]-7-methyl-1,7-diazaspiro[4.4]nonan-6-one hydrochloride (E8) and (2R,5R)-2-[4-(5-Ethoxy-2-fluoro-phenyl)-6-methyl-pyrimidin-2-yl]-7-methyl-1,7-diazaspiro[4.4]nonan-6-one hydrochloride (E9)

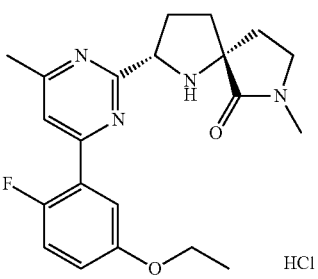

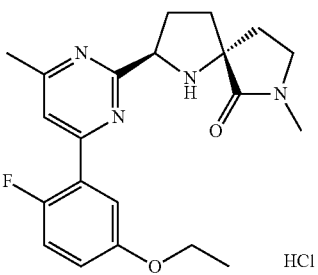

Concentrated aq. HCl (75.18 μL, 0.88 mmol) was added to a solution of the (5R)-2-[4-(5-ethoxy-2-fluoro-phenyl)-6-methyl-pyrimidin-2-yl]-7-methyl-1,7-diazaspiro[4.4]non-1-en-6-one (which may be prepared as described in Description 20) (335 mg, 0.88 mmol) in DCM (20 mL) at 0° C. Finally, sodium triacetoxyborohydride (556.96 mg, 2.63 mmol) was added in a single portion and the resulting mixture was stirred for 90 mins. The reaction was quenched by the addition of sat. Na₂CO₃ and the resultant mixture was stirred for 5 mins. The phases were separated, the organic layer was dried (Na₂SO₄) and the solvent was evaporated to afford a brown oil. The material was purified using a Biotage SP4 with a 25 g SNAP cartridge, eluting with 0 to 20% MeOH/EtOAc over 20 column volumes. A partial separation was achieved. Faster running fractions were collected and evaporated to afford (2S, 5R)-2-[4-(5-ethoxy-2-fluoro-phenyl)-6-methyl-pyrimidin-2-yl]-7-methyl-1,7-diazaspiro[4.4]nonan-6-one as a light brown oil (97 mg)

300 MHz NMR $\delta_H$ (CDCl₃) 1.45 (3H, t), 1.83-1.97 (1H, m), 2.06-2.34 (5H, m), 2.58 (3H, s), 2.54-2.68 (1H, m), 2.92 (3H, s), 3.26-3.42 (2H, m), 4.09 (2H, q), 4.83 (1H, t), 6.94-6.99 (1H, m), 7.09 (1H, t), 7.55 (1H, d), 7.68-7.71 (1H, m).

A further round of chromatographic purification of impure fractions yielded a total of 168 mg of this material.

This material (168 mg, 0.44 mmol) was dissolved in DCM (2 mL) at 20° C. To this was added 1M HCl in ether (0.44 mL, 0.44 mmol) and the reaction was stood for 5 mins. The solvent was evaporated to afford the (2S,5R)-2-[4-(5-ethoxy-2-fluoro-phenyl)-6-methyl-pyrimidin-2-yl]-7-methyl-1,7-diazaspiro[4.4]nonan-6-one hydrochloride (E8) (176 mg, 0.4578 mmol) as a light brown solid.

m/z: 385 (M+H⁺).

The remaining mixed isomer free base fractions from the initial preparation were subjected to purification by chiral HPLC with a preparative IA column, eluting with 20% EtOH/ Heptane. Two peaks observed at 11.25 and 16.03 mins. The slower to elute component was identical with the free base form of E8 and the faster component, assigned as (2R,5R)-2-[4-(5-ethoxy-2-fluoro-phenyl)-6-methyl-pyrimidin-2-yl]-7-methyl-1,7-diazaspiro[4.4]nonan-6-one, was isolated (56 mg);

300 MHz NMR $\delta_H$ (CDCl₃) 1.44 (3H, t), 1.77-1.88 (1H, m), 2.02-2.28 (4H, m), 2.39-2.52 (1H, m), 2.57 (3H, s), 2.42 (3H, s), 3.27-3.44 (2H, m), 3.7 (1H, br.s), 4.14 (2H, q), 4.48 (1H, t), 6.93-6.97 (1H, m), 7.06 (1H, dd), 7.57 (1H, d), 7.83-7.87 (1H, m).

This material was dissolved in DCM (2 mL) at 20° C. To this was added 1M HCl in ether (0.15 mL, 0.15 mmol) and the reaction was stood for 5 mins. The solvent was evaporated to afford (2R,5R)-2-[4-(5-ethoxy-2-fluoro-phenyl)-6-methyl-pyrimidin-2-yl]-7-methyl-1,7-diazaspiro[4.4]nonan-6-one hydrochloride (E9) (59 mg, 0.1535 mmol) as a light brown solid;

m/z: 385 (M+H⁺).

Examples 10, 11

| Example Number | Structure | Name | Analysis | Method |
|---|---|---|---|---|
| E10 | 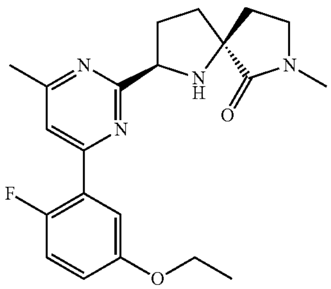 | (2R,5S)-2-[4-(5-Ethoxy-2-fluoro-phenyl)-6-methyl-pyrimidin-2-yl]-7-methyl-1,7-diazaspiro[4.4]nonan-6-one hydrochloride | m/z: 385 (M + H⁺) | Using the method of Example 8 but using D4 in place of D10 in Description 18 |
| E11 | 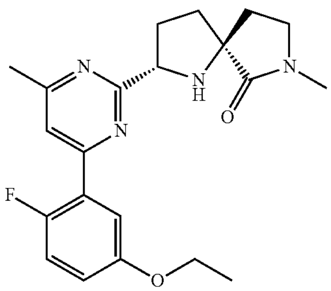 | (2S,5S)-2-[4-(5-Ethoxy-2-fluoro-phenyl)-6-methyl-pyrimidin-2-yl]-7-methyl-1,7-diazaspiro[4.4]nonan-6-one hydrochloride | m/z: 385 (M + H⁺) | Using the method of Example 9 but using D4 in place of D10 in Description 18 |

Examples 12, 13

(2R,6S)-2-[4-(5-Ethoxy-2-fluoro-phenyl)-6-methyl-pyrimidin-2-yl]-1,8-diazaspiro[4.5]decan-7-one hydrochloride (E12) (2S,6S)-2-[4-(5-Ethoxy-2-fluoro-phenyl)-6-methyl-pyrimidin-2-yl]-1,8-diazaspiro[4.5]decan-7-one hydrochloride (E13)

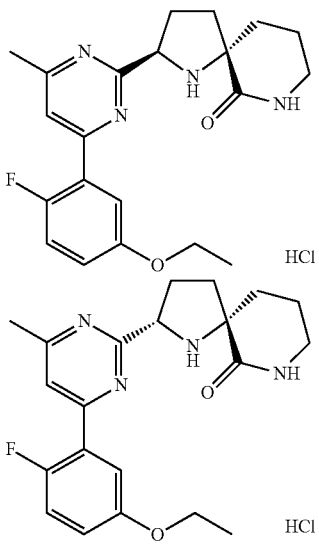

Concentrated aq. HCl (0.01 mL, 0.16 mmol) was added to a solution of (6S)-2-[4-(5-ethoxy-2-fluoro-phenyl)-6-methyl-pyrimidin-2-yl]-1,8-diazaspiro[4.5]dec-1-en-7-one (which may be prepared as described in Description 28) (61 mg, 0.16 mmol) at 0° C. Finally, sodium triacetoxyborohydride (101.42 mg, 0.48 mmol) was added in a single portion and the resulting mixture was stirred for 90 mins. TLC (10% MeOH/EtOAc): No SM remains. 2 diastereoisomers were observed, but with very poor separation (Rf=0.2 and 0.1) The reaction was quenched by the addition of satd. aq. Na₂CO₃ and the resultant mixture was stirred for 5 mins. The phases were separated, the organic layer was dried (Na₂SO₄) and the solvent was evaporated to afford a brown oil (49 mg) a 4:1 mixture of anti:syn diastereoisomers. This was purified using a chiral HPLC using an IA column eluting with 20% EtOH/Heptane. The minor isomer, the faster running component: (2R,6S)-2-[4-(5-ethoxy-2-fluoro-phenyl)-6-methyl-pyrimidin-2-yl]-1,8-diazaspiro[4.5]decan-7-one was isolated (6.5 mg);

300 MHz NMR $\delta_H$ (CDCl₃) 1.45 (3H, t), 1.60-2.08 (7H, m), 2.26-2.34 (1H, m), 2.42-2.51 (1H, m), 2.59 (3H, s), 3.31-3.48 (2H, m), 4.13 (2H, q), 4.45 (1H, dd), 5.75 (1H, br.s), 6.72-6.79 (1H, m), 7.07 (1H, dd), 7.58 (1H, d), 7.82 (1H, dd).

1M HCl in Et₂O (0.02 mL, 0.0200 mmol) was added to a solution of this material in DCM (1 mL) at 20° C. and the reaction was stirred for 2 mins. The solvent was evaporated to afford the (2R,6S)-2-[4-(5-ethoxy-2-fluoro-phenyl)-6-methyl-pyrimidin-2-yl]-1,8-diazaspiro[4.5]decan-7-one hydrochloride (E12) (6.8 mg, 0.0177 mmol) as a light brown solid; m/z: 385 (M+H⁺).

The major isomer (2S,6S)-2-[4-(5-ethoxy-2-fluoro-phenyl)-6-methyl-pyrimidin-2-yl]-1,8-diazaspiro-[4.5]decan-7-one (29 mg) was isolated as the slower running component from the chiral column.

300 MHz NMR δ$_H$ (CDCl$_3$) 1.28 (1H, br.s), 1.45 (3H, t), 1.85-2.20 (6H, m), 2.29-2.39 (1H, m), 2.51-2.64 (4H, m), 3.30-3.45 (2H, m), 4.09 (2H, q), 4.85 (1H, t), 5.78 (1H, br.s), 6.93-6.99 (1H, m), 7.08 (1H, t), 7.54 (1H, d), 7.71 (1H, dd).

1M HCl in Et$_2$O (0.08 mL, 0.0800 mmol) was added to a solution of this material in DCM (1 mL) at 20° C. and the reaction was stirred for 2 mins. The solvent was evaporated to afford the (2S,6S)-2-[4-(5-ethoxy-2-fluoro-phenyl)-6-methyl-pyrimidin-2-yl]-1,8-diazaspiro[4.5]-decan-7-one hydrochloride (E13) (31 mg, 0.0806 mmol) as a light brown solid;

m/z: 385 (M+H$^+$)

Examples 14-38

E14-E38

The compounds of Examples 14-38 were prepared using the methods referenced with modifications noted and alternative boronic acids where given.

| Example Number | Structure | Name | Analysis | Method |
|---|---|---|---|---|
| E14 | 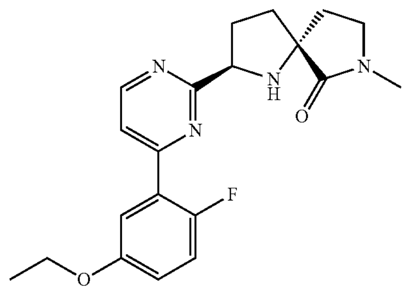 | (2R,5R)-2-[4-(5-Ethoxy-2-fluoro-phenyl)pyrimidin-2-yl]-7-methyl-1,7-diazaspiro[4.4]nonan-6-one hydrochloride | m/z: 371 (M + H$^+$) | Using the method described for Example 4 but using D10 and D17 in place of D4 and D6 in Description 7 |
| E15 | 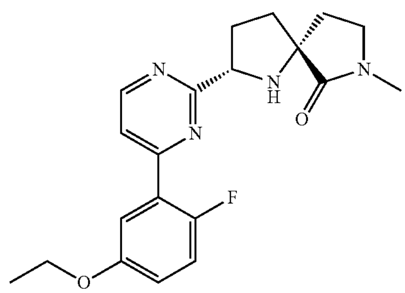 | (2S,5R)-2-[4-(5-Ethoxy-2-fluoro-phenyl)pyrimidin-2-yl]-7-methyl-1,7-diazaspiro[4.4]nonan-6-one hydrochloride | m/z: 371 (M + H$^+$) | Using the method described for Example 3 but using D10 and D17 in place of D4 and D6 in Description 7 |
| E16 | 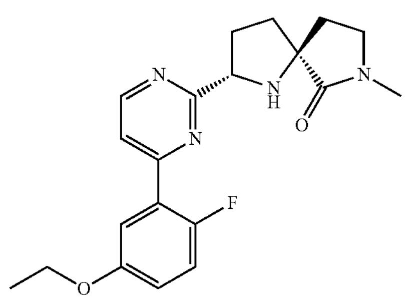 | (2S,5S)-2-[4-(5-Ethoxy-2-fluoro-phenyl)pyrimidin-2-yl]-7-methyl-1,7-diazaspiro[4.4]nonan-6-one hydrochloride | m/z: 371 (M + H$^+$) | Using the method described for Example 2 but using D17 in place of D6 in Description 7 |
| E17 | 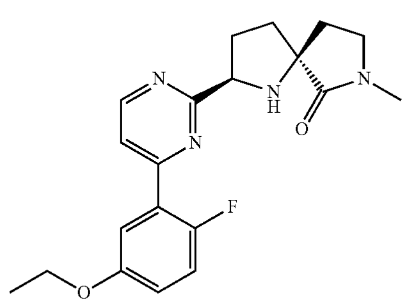 | (2R,5S)-2-[4-(5-Ethoxy-2-fluoro-phenyl)pyrimidin-2-yl]-7-methyl-1,7-diazaspiro[4.4]nonan-6-one hydrochloride | m/z: 371 (M + H$^+$) | Using the method described for Example 1 but using D17 in place of D6 in Description 7 |

-continued

| Example Number | Structure | Name | Analysis | Method |
|---|---|---|---|---|
| E18 | 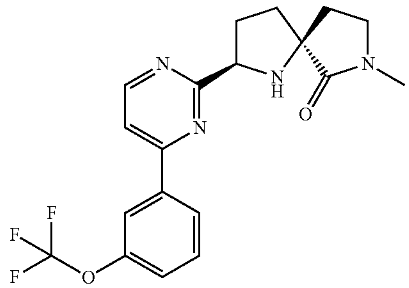 | (2R,5S)-7-Methyl-2-[4-[3-(trifluoromethoxy)phenyl]pyrimidin-2-yl]-1,7-diazaspiro[4.4]nonan-6-one hydrochloride | m/z: 393 (M + H$^+$) | Using the method described for Example 1 but using 3-trifluoromethoxy-phenylboronic acid |
| E19 | 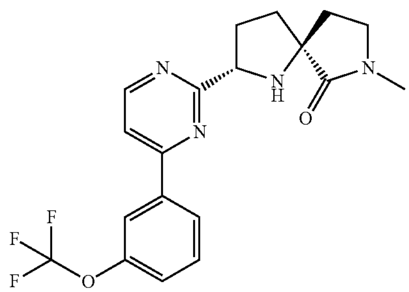 | (2S,5S)-7-Methyl-2-[4-[3-(trifluoromethoxy)phenyl]pyrimidin-2-yl]-1,7-diazaspiro[4.4]nonan-6-one hydrochloride | m/z: 393 (M + H$^+$) | Using the method described for Example 2 but using 3-trifluoromethoxy-phenylboronic acid |
| E20 | 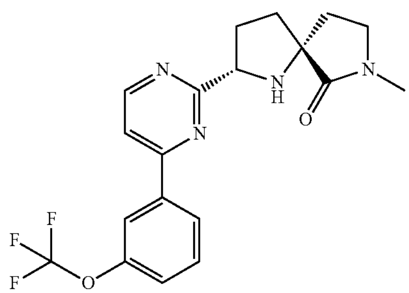 | (2S,5R)-7-Methyl-2-[4-[3-(trifluoromethoxy)phenyl]pyrimidin-2-yl]-1,7-diazaspiro[4.4]nonan-6-one hydrochloride | m/z: 393 (M + H$^+$) | Using the method described for Example 3 but using 3-trifluoromethoxy-phenylboronic acid |
| E21 | 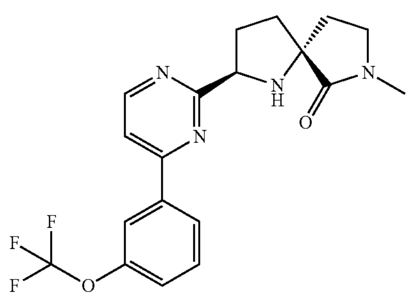 | (2R,5R)-7-Methyl-2-[4-[3-(trifluoromethoxy)phenyl]pyrimidin-2-yl]-1,7-diazaspiro[4.4]nonan-6-one hydrochloride | m/z: 393 (M + H$^+$) | Using the method described for Example 4 but using 3-trifluoromethoxy-phenylboronic acid |

-continued

| Example Number | Structure | Name | Analysis | Method |
|---|---|---|---|---|
| E22 | 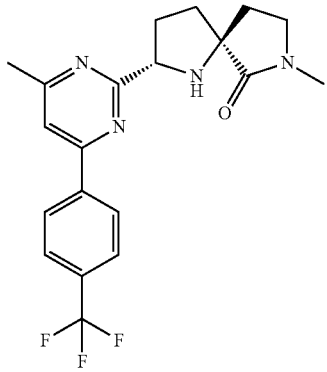 HCl | (2S,5S)-7-Methyl-2-[4-methyl-6-[4-(trifluoromethyl)-phenyl]pyrimidin-2-yl]-1,7-diazaspiro[4.4]nonan-6-one hydrochloride | m/z: 391 (M + H$^+$) | Using the method described for Example 7 but using syn isomer A in place of anti isomer B |
| E23 | 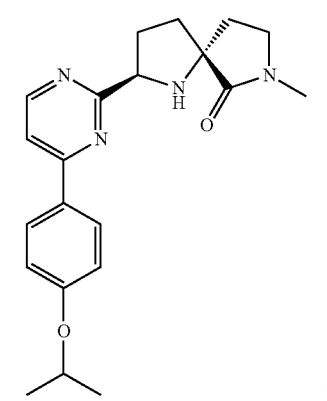 HCl | (2R,5R)-2-[4-(4-Isopropoxyphenyl)pyrimidin-2-yl]-7-methyl-1,7-diazaspiro[4.4]nonan-6-one hydrochloride | m/z: 367 (M + H$^+$) | Using the method described for Example 4 but using 4-isopropyloxyphenyl boronic acid |
| E24 | 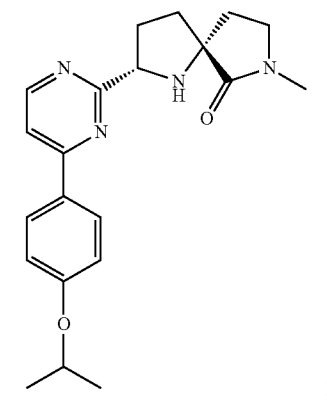 HCl | (2S,5R)-2-[4-(4-Isopropoxyphenyl)pyrimidin-2-yl]-7-methyl-1,7-diazaspiro[4.4]nonan-6-one hydrochloride | m/z: 367 (M + H$^+$) | Using the method described for Example 3 but using 4-isopropyloxyphenyl boronic acid |
| E25 | 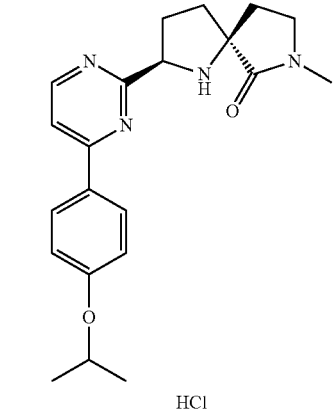 [SMILES: CC(C)Oc1ccc(-c2ccnc([C@H]3CC[C@@]4(CCN(C)C4=O)N3)n2)cc1 ; Cl] HCl | (2R,5S)-2-[4-(4-Isopropoxyphenyl)pyrimidin-2-yl]-7-methyl-1,7-diazaspiro[4.4]nonan-6-one hydrochloride | m/z: 367 (M + H$^+$) | Using the method described for Example 1 but using 4-isopropyloxyphenyl boronic acid |

| Example Number | Structure | Name | Analysis | Method |
|---|---|---|---|---|
| E26 | 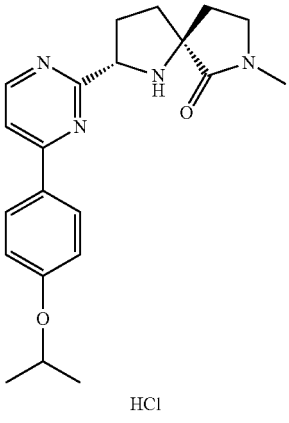 [SMILES: CC(C)Oc1ccc(-c2ccnc([C@@H]3CC[C@@]4(CCN(C)C4=O)N3)n2)cc1 ; Cl] HCl | (2S,5S)-2-[4-(4-Isopropoxyphenyl)pyrimidin-2-yl]-7-methyl-1,7-diazaspiro[4.4]nonan-6-one hydrochloride | m/z: 367 (M + H⁺) | Using the method described for Example 2 but using 4-isopropyloxyphenyl boronic acid |
| E27 | 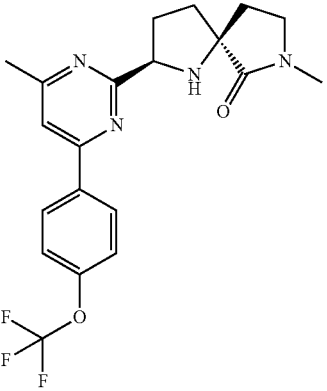 HCl | (2R,5S)-7-Methyl-2-[4-methyl-6-[4-(trifluoromethoxy)phenyl]pyrimidin-2-yl]-1,7-diazaspiro[4.4]nonan-6-one hydrochloride | m/z: 407 (M + H⁺) | Using the method of Example 10 but using 4-trifluoromethoxyphenyl boronic acid |
| E28 | 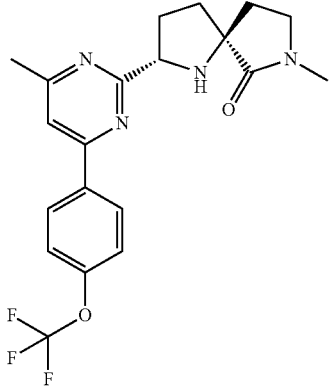 HCl | (2S,5S)-7-Methyl-2-[4-methyl-6-[4-(trifluoromethoxy)phenyl]pyrimidin-2-yl]-1,7-diazaspiro[4.4]nonan-6-one hydrochloride | m/z: 407 (M + H⁺) | Using the method of Example 11 but using 4-trifluoromethoxyphenyl boronic acid |

| Example Number | Structure | Name | Analysis | Method |
|---|---|---|---|---|
| E29 | 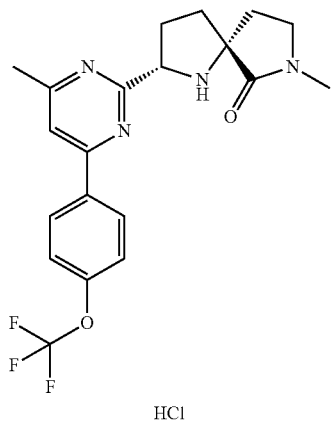 HCl | (2S,5R)-7-Methyl-2-[4-methyl-6-[4-(trifluoromethoxy)phenyl]pyrimidin-2-yl]-1,7-diazaspiro[4.4]nonan-6-one hydrochloride | m/z: 407 (M + H$^+$) | Using the method of Example 8 but using 4-trifluoromethoxyphenyl boronic acid |
| E30 | 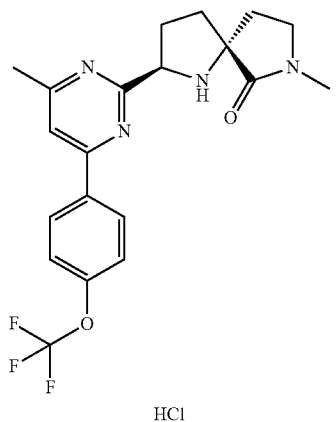 HCl | (2R,5R)-7-Methyl-2-[4-methyl-6-[4-(trifluoromethoxy)phenyl]pyrimidin-2-yl]-1,7-diazaspiro[4.4]nonan-6-one hydrochloride | m/z: 407 (M + H$^+$) | Using the method of Example 9 but using 4-trifluoromethoxyphenyl boronic acid |
| E31 | 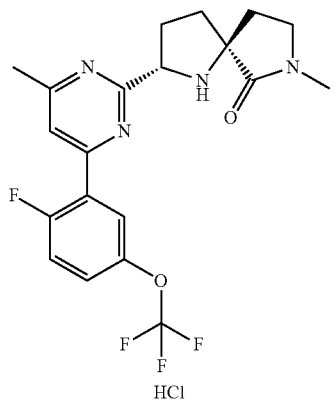 HCl | (2S,5S)-2-[4-[2-Fluoro-5-(trifluoromethoxy)phenyl]-6-methyl-pyrimidin-2-yl]-7-methyl-1,7-diazaspiro[4.4]nonan-6-one hydrochloride | m/z: 425 (M + H$^+$) | Using the method of Example 11 but using 2-fluoro-5-trifluoromethoxyphenyl boronic acid |

-continued

| Example Number | Structure | Name | Analysis | Method |
|---|---|---|---|---|
| E32 | 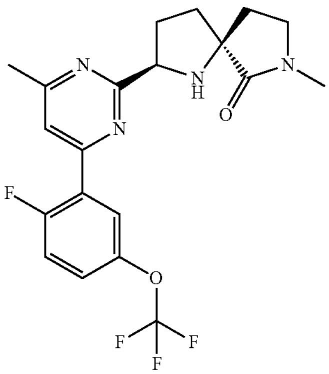 | (2R,5S)-2-[4-[2-Fluoro-5-(trifluoromethoxy)phenyl]-6-methyl-pyrimidin-2-yl]-7-methyl-1,7-diazaspiro[4.4]nonan-6-one hydrochloride | m/z: 425 (M + H$^+$) | Using the method of Example 10 but using 2-fluoro-5-trifluoromethoxyphenyl boronic acid |
| E33 | 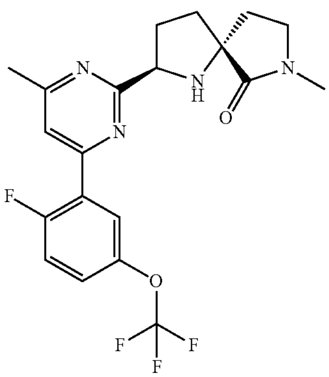 | (2R,5R)-2-[4-[2-Fluoro-5-(trifluoromethoxy)phenyl]-6-methyl-pyrimidin-2-yl]-7-methyl-1,7-diazaspiro[4.4]nonan-6-one hydrochloride | m/z: 425 (M + H$^+$) | Using the method of Example 9 but using 2-fluoro-5-trifluoromethoxyphenyl boronic acid |
| E34 | 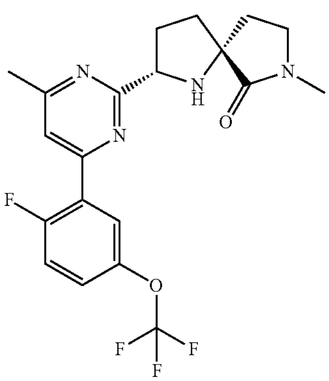 | (2S,5R)-2-[4-[2-Fluoro-5-(trifluoromethoxy)phenyl]-6-methyl-pyrimidin-2-yl]-7-methyl-1,7-diazaspiro[4.4]nonan-6-one hydrochloride | m/z: 425 (M + H$^+$) | Using the method of Example 8 but using 2-fluoro-5-trifluoromethoxyphenyl boronic acid |
| E35 | 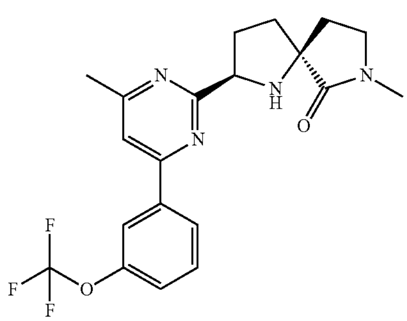 | (2R,5S)-7-Methyl-2-[4-methyl-6-[3-(trifluoromethoxy)phenyl]pyrimidin-2-yl]-1,7-diazaspiro[4.4]nonan-6-one hydrochloride | m/z: 407 (M + H$^+$) | Using the method of Example 10 but using 3-trifluoromethoxyphenyl boronic acid |

| Example Number | Structure | Name | Analysis | Method |
|---|---|---|---|---|
| E36 | 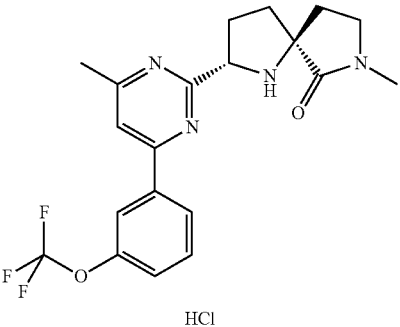 [SMILES: Cc1cc(-c2cccc(OC(F)(F)F)c2)nc([C@@H]2CC[C@@]3(CCN(C)C3=O)N2)n1 ; Cl] HCl | (2S,5S)-7-Methyl-2-[4-methyl-6-[3-(trifluoromethoxy)phenyl]pyrimidin-2-yl]-1,7-diazaspiro[4.4]nonan-6-one hydrochloride | m/z: 407 (M + H⁺) | Using the method of Example 11 but using 3-trifluoromethoxyphenyl boronic acid |
| E37 | 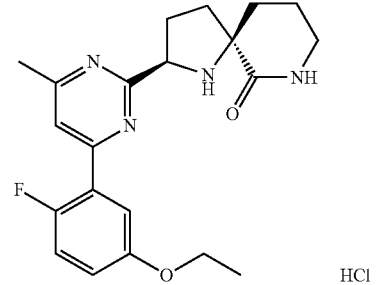 [SMILES: CCOc1ccc(F)c(-c2cc(C)nc([C@H]3CC[C@@]4(CCCNC4=O)N3)n2)c1 ; Cl] HCl | (2R,6R)-2-[4-(5-Ethoxy-2-fluoro-phenyl)-6-methyl-pyrimidin-2-yl]-1,8-diazaspiro[4.5]decan-7-one hydrochloride | m/z: 385 (M + H⁺) | Using the method of Example 13 but using but using D24R in place of D24S |
| E38 | 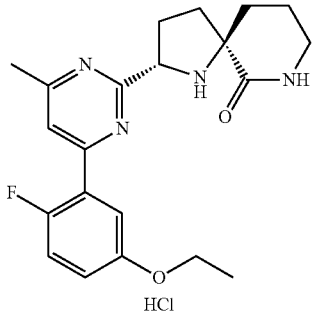 [SMILES: CCOc1ccc(F)c(-c2cc(C)nc([C@@H]3CC[C@@]4(CCCNC4=O)N3)n2)c1 ; Cl] HCl | (2S,6R)-2-[4-(5-Ethoxy-2-fluoro-phenyl)-6-methyl-pyrimidin-2-yl]-1,8-diazaspiro[4.5]decan-7-one hydrochloride | m/z: 385 (M + H⁺) | Using the method of Example 12 but using D24R in place of D24S |

Examples 39-42

(2R,5S)-2-[4-Methyl-6-[4-(trifluoromethyl)phenyl]pyrimidin-2-yl]-1,7-diazaspiro[4.4]-nonan-6-one hydrochloride (E39), (2S,5R)-2-[4-Methyl-6-[4-(trifluoromethyl)phenyl]-pyrimidin-2-yl]-1,7-diazaspiro[4.4]nonan-6-one hydrochloride (E40), (2S,5S)-2-[4-Methyl-6-[4(trifluoromethyl)-phenyl]-pyrimidin-2-yl]-1,7-diazaspiro[4.4]nonan-6-one hydrochloride (E41), (2R,5R)-2-[4-Methyl-6-[4-(trifluoromethyl)phenyl]pyrimidin-2-yl]-1,7-diazaspiro[4.4]nonan-6-one hydrochloride (E42)

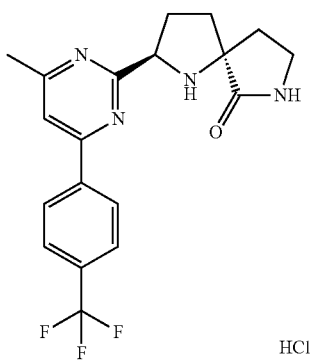

HCl

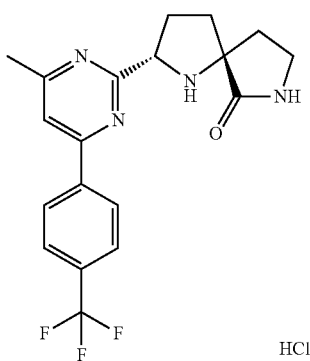

HCl

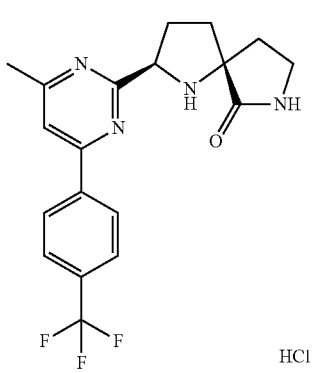

HCl

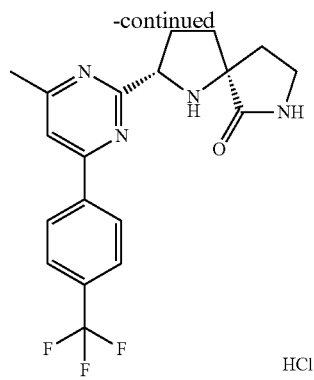

HCl

Concentrated aq. hydrochloric acid (0.19 mL, 2.25 mmol) was added to an ice-cooled, stirred solution of 2-[4-methyl-6-[4-(trifluoromethyl)phenyl]pyrimidin-2-yl]-1,7-diazaspiro[4.4]non-1-en-6-one (which may be prepared as described in Description 31) (765 mg, 2.04 mmol) in dry DCM (25 mL) under nitrogen. After leaving for approximately 4 minutes, sodium triacetoxyborohydride (1.73 g, 8.17 mmol) was added portionwise over 3 minutes. After stirring for 30 mins, the ice bath was removed and the mixture was stirred at ambient temperature for 1 h. The reaction was poured into sat. aq. NaHCO$_3$ solution (25 ml) and stirred for 5 minutes. DCM (30 ml) and water (25 ml) were added with shaking. The layers were separated and the aqueous phase further extracted with DCM (2×20 ml). The combined organic extracts were dried (Na$_2$SO$_4$) and evaporated to a foam. This was purified by silica gel KP-NH column chromatography: eluting with with a gradient of methanol in EtOAc. Two fractions were collected corresponding to cis and anti isomers;

Faster eluting diastereomers were racemic (2R,5R)- and (2S,5S)-2-[4-methyl-6-[4-(trifluoromethyl)phenyl]pyrimidin-2-yl]-1,7-diazaspiro[4.4]-nonan-6-one (127 mg);

300 MHz NMR δ$_H$ (CDCl$_3$) 1.7 (1H, br.s), 1.91 (1H, m), 2.08-2.26 (2H, m), 2.28-2.56 (2H, m), 2.62 (3H, s), 3.38 (1H, m), 3.47 (1H, td), 3.75 (1H, br.s), 4.52 (1H, t), 5.8 (1H br.s), 7.48 (1H, s), 7.76 (2H, d), 8.28 (2H, d).

The slower eluting diastereomers were racemic (2R,5S)- and (2S,5R)-2-[4-methyl-6-[4-(trifluoromethyl)phenyl]-pyrimidin-2-yl]-1,7-diazaspiro[4.4]-nonan-6-one (368 mg);

300 MHz NMR δ$_H$ (CDCl$_3$) 1.7 (1H, br.s), 1.97 (1H, m), 2.10-2.25 (2H, m), 2.26-2.43 (2H, m), 2.58-2.67 (1H, m), 2.62 (3H, s), 3.35 (1H, m), 3.44 (1H, td), 4.84 (1H, t), 5.86 (1H, br.s), 7.47 (1H, s), 7.68 (2H, d), 8.21 (2H, d).

The slower isomer mix was separated using a chiralPaK IA preparative column (20 mm×250 mm, 5 um) eluting with 20% EtOH/heptanes. Two fractions were collected:

First to elute (2R,5S)-2-[4-methyl-6-[4-(trifluoromethyl)phenyl]pyrimidin-2-yl]-1,7-diazaspiro[4.4]nonan-6-one (89 mg); Optical Rotation α[D/20)]=+16.7 deg (c=0.48, CHCl$_3$); Rt=12.1 minutes.

The second component (Rt=16.2 mins) co-eluted with a contaminant which was removed by further chromatography using KP-NH silica gel, eluting with acetone in dichloromethane, to give (2S,5R)-2-[4-methyl-6-[4-(trifluoromethyl)phenyl]pyrimidin-2-yl]-1,7-diazaspiro[4.4]nonan-6-one (68 mg); Optical Rotation α[D/20]=−12.5 (c=0.48, CHCl$_3$).

To a solution of this material (67 mg, 0.1800 mmol) in DCM (1 mL), was added hydrogen chloride in Et$_2$O (1M, 0.2 mL, 0.2000 mmol). The mixture was diluted with Et$_2$O (3 ml) and stirred for 0.5 h. The supernatant was decanted off to leave a cream solid, which was dried under vacuum to afford (2R,5S)-2-[4-methyl-6-[4-(trifluoromethyl)phenyl]pyrimidin-2-yl]-1,7-diazaspiro[4.4]nonan-6-one hydrochloride (E39) (72 mg); m/z: 376 (M+H$^+$).

The (2S,5R) free base antipode (67 mg) was treated similarly forming (2S,5R)-2-[4-methyl-6-[4-(trifluoromethyl)phenyl]pyrimidin-2-yl]-1,7-diazaspiro[4.4]nonan-6-one hydrochloride (E40) (72 mg); m/z: 376 (M+H$^+$).

The racemic mixture of (2R,5R) and (2S,5S) isomers was converted to their Boc derivatives to facilitate separation. A stirred solution of racemic (2R,5R)- and (2S,5S)-2-[4-methyl-6-[4-(trifluoromethyl)phenyl]pyrimidin-2-yl]-1,7-diazaspiro[4.4]nonan-6-one (127 mg, 0.3400 mmol) and tert-butoxycarbonyl tert-butyl carbonate (220.93 mg, 1.01 mmol) in DCE (3 mL) was heated under N$_2$ at block temp 50° C. for 18 h. The reaction mixture was cooled to ambient temperature and evaporated to an oil, which was applied to a 10 g cartridge and eluted on a Biotage SP4 system with a gradient of methanol in ethyl acetate. Relevant fractions were combined and evaporated to a solid, a racemic mixture of tert-butyl (2S,5S)- and (2R,5R)-2-[4-methyl-6-[4-(trifluoromethyl)phenyl]pyrimidin-2-yl]-6-oxo-1,7-diazaspiro[4.4]nonane-1-carboxylate (116 mg). This was separated by chiral chromatography using an IA chiralPak preparative column eluting with 10% EtOH in heptanes to give the first to elute isomer: tert-butyl (2S,5S)-2-[4-methyl-6-[4-(trifluoromethyl)phenyl]pyrimidin-2-yl]-6-oxo-1,7-diazaspiro[4.4]nonane-1-carboxylate (37 mg); m/z 477 (M+H$^+$). Also the second to elute: tert-butyl (2R,5R)-2-[4-methyl-6-[4-(trifluoromethyl)phenyl]pyrimidin-2-yl]-6-oxo-1,7-diazaspiro[4.4]nonane-1-carboxylate (37 mg); m/z 477 (M+H$^+$).

tert-Butyl (2S,5S)-2-[4-methyl-6-[4-(trifluoromethyl)phenyl]pyrimidin-2-yl]-6-oxo-1,7-diazaspiro[4.4]nonane-1-carboxylate (37 mg, 0.0800 mmol) was added to a stirred solution of 4M HCl in 1,4-dioxan (2 mL, 8 mmol) in DCM (2 mL) at ambient temperature. The colourless solution was stirred in a stoppered flask for 4 h. The solution was evaporated and re-evaporated with toluene (25 ml). The residue was dissolved in MeOH (2 ml) and passed through a 2 g SCX cartridge, eluting with MeOH then 1M NH$_3$-MeOH to give (2S,5S)-2-[4-methyl-6-[4-(trifluoromethyl)phenyl]pyrimidin-2-yl]-1,7-diazaspiro[4.4]nonan-6-one (31 mg); m/z 377 (M+H$^+$); Optical Rotation α[D/20]=−33.9 (c=0.56, CHCl$_3$).

1M hydrogen chloride in Et$_2$O (0.09 mL, 0.0900 mmol) was added to a stirred solution of (2S,5S)-2-[4-methyl-6-[4-(trifluoromethyl)phenyl]pyrimidin-2-yl]-1,7-diazaspiro[4.4]nonan-6-one (31 mg, 0.0800 mmol) in DCM (1 mL) at ambient temperature. The solution was evaporated to a gum with a stream of N$_2$ then Et$_2$O (1 ml) was added. The suspension was stirred for 5 mins and then evaporated with a stream of N$_2$ and dried under vacuum to give a solid: (2S,5S)-2-[4-methyl-6-[4-(trifluoromethyl)phenyl]pyrimidin-2-yl]-1,7-diazaspiro[4.4]-nonan-6-one hydrochloride (E41) (33 mg); m/z 377 (M+H$^+$).

In a similar manner, tert-butyl (2R,5R)-2-[4-methyl-6-[4-(trifluoromethyl)phenyl]pyrimidin-2-yl]-6-oxo-1,7-diazaspiro[4.4]nonane-1-carboxylate (37 mg) was converted first to the free base (2R,5R)-2-[4-methyl-6-[4-(trifluoromethyl)phenyl]pyrimidin-2-yl]-1,7-diazaspiro[4.4]-nonan-6-one (27 mg); m/z 377 (M+H$^+$); Optical Rotation α[D/20)]=+32.1 (c=0.56, CHCl$_3$). This material was subsequently treated with HCl in ether to form (2R,5R)-2-[4-methyl-6-[4-(trifluoromethyl)-phenyl]pyrimidin-2-yl]-1,7-diazaspiro[4.4]nonan-6-one hydrochloride (E42) (32 mg); m/z 377 (M+H$^+$).

Examples 43-46

E43-E46

Examples 43-46 were prepared using the route described for Examples 5 and 6 with modifications noted.

| Example Number | Structure | Name | Analysis | Modifications |
|---|---|---|---|---|
| E43 | 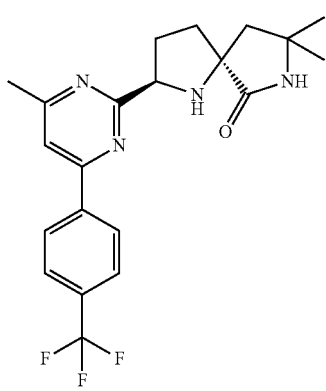 | (2R,5S)-8,8-Dimethyl-2-[4-methyl-6-[4-(trifluoromethyl)phenyl]pyrimidin-2-yl]-1,7-diazaspiro[4.4]nonan-6-one hydrochloride | m/z: 405 (M + H+) | Using D38S in place of D15 |

| Example Number | Structure | Name | Analysis | Modifications |
|---|---|---|---|---|
| E44 | 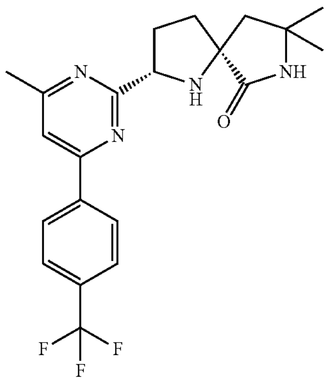 | (2S,5S)-8,8-Dimethyl-2-[4-methyl-6-[4-(trifluoromethyl)phenyl]pyrimidin-2-yl]-1,7-diazaspiro[4.4]nonan-6-one hydrochloride | m/z: 405 (M + H+) | Using D38S in place of D15 |
| E45 | 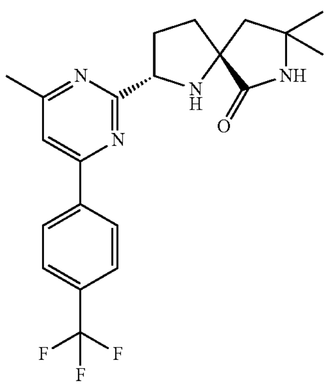 | (2S,5R)-8,8-Dimethyl-2-[4-methyl-6-[4-(trifluoromethyl)phenyl]pyrimidin-2-yl]-1,7-diazaspiro[4.4]nonan-6-one hydrochloride | m/z: 405 (M + H+) | Using D38R in place of D15 |
| E46 | 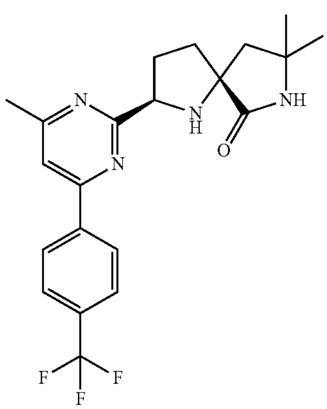 | (2R,5R)-8,8-Dimethyl-2-[4-methyl-6-[4-(trifluoromethyl)phenyl]pyrimidin-2-yl]-1,7-diazaspiro[4.4]nonan-6-one hydrochloride | m/z: 405 (M + H+) | Using D38R in place of D15 |

Biological Assays

The compounds of the invention were tested in a QPatch NaV1.7 assay.

QPatch NaV1.7 Assay

HEK293-hNaV1.7 cells were grown in DMEM-F12+10% FBS culture media at 37° C. At a confluency of 50-70% cells were dissociated from culture flasks & triturated to ensure unicellular cell suspension; cell density was measured & adjusted to 2-3×10$^6$ cells/ml. Recordings were obtained using QPatch16x. The external solution was (in mM): NaCl, 128; KCl, 5; MgCl$_2$, 2; CaCl$_2$, 2; Glucose, 30; HEPES, 15; pH 7.3, 305-315 mOsm. Following seal formation and whole-cell access using internal solution (containing in mM: CsF, 135; EGTA/CsOH, 1/5; HEPES 10; NaCl, 10; pH 7.3, 310-320mOsM), voltage pulse protocols were applied. Initially a steady state inactivation voltage protocol was used to determine the half-maximal voltage for steady state inactivation (V1/2 SSI). Two holding voltages were used to determine test drug inhibition: −90 mV, where most of the channels are in a closed state; and V1/2 SSI, where half of the channels are inactivated. Currents were elicited every 10 seconds by stepping to a membrane potential of 0 mV for 20 ms. Four-point cumulative concentration responses were derived by determining the peak current amplitude at each concentration of test drug over 120 second application. Curves were fitted with the Hill equation yielding pIC50 values at −90 mV and V1/2 SSI holding potentials.

| Example Number | QP Nav1.7 - 90 mV pIC50 | QP Nav1.7 SSI vhalf pIC50 |
| --- | --- | --- |
| 1 | 3.9 | 5.0 |
| 2 | 3.4 | 4.2 |
| 3 | 3.8 | 4.5 |
| 4 | 3.6 | 4.4 |
| 5 | 4.1 | 4 |
| 6 | 3.5 | 4.1 |
| 7 | 3.9 | 5.7 |
| 8 | 4.4 | 5.6 |
| 9 | 4.9 | 5.8 |
| 10 | 4.7 | 5.8 |
| 11 | 4.1 | 5.4 |
| 12 | 4.7 | 5.7 |
| 13 | 5.1 | 5.8 |
| 14 | 4.7 | 5.9 |
| 15 | 3.9 | 4.9 |
| 16 | 3.9 | 4.9 |
| 17 | 4.2 | 5 |
| 18 | 3.9 | 4.9 |
| 19 | 3.7 | 4.7 |
| 20 | 3.7 | 4.6 |
| 21 | 3.7 | 4.8 |
| 22 | 2.1 | 4.2 |
| 23 | 2.8 | 4.2 |
| 24 | 3.8 | 4.7 |
| 25 | 4.3 | 5.1 |
| 26 | 3.2 | 4.3 |
| 27 | 4.2 | 5.0 |
| 28 | 3.2 | 4.3 |
| 29 | 3.9 | 4.9 |
| 30 | 3.5 | 4.7 |
| 31 | 4.0 | 5.5 |
| 32 | 4.4 | 5.6 |
| 33 | 4.7 | 5.7 |
| 34 | 4.1 | 5.1 |
| 37 | 4.8 | 5.8 |
| 38 | 4.3 | 5.5 |
| 39 | 3.9 | 4.8 |
| 40 | 3.8 | 4.5 |
| 41 | 4.6 | 5.6 |
| 42 | 3.3 | 4.3 |
| 43 | 4.5 | 5.3 |
| 44 | 3.8 | 4.4 |
| 45 | 4.0 | 4.7 |
| 46 | 4.6 | 5.5 |

The invention claimed is:

1. A compound of formula (I) or a pharmaceutically acceptable salt thereof:

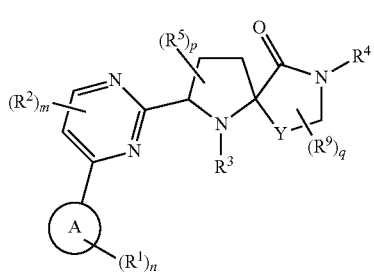

(I)

wherein:
Ring A represents a phenyl ring, a 5- or 6-membered aromatic heterocyclic ring or a 5- to 12-membered aromatic or non-aromatic bicyclic heterocyclic group;
n represents an integer selected from 0 to 4;
each $R^1$ independently represents $C_{1-6}$ alkyl, $C_{2-6}$ alkenyl, $C_{2-6}$ alkynyl, -Z—$C_{3-6}$ cycloalkyl, halogen, halo$C_{1-6}$ alkyl, $C_{1-6}$ alkoxy, halo$C_{1-6}$ alkoxy, -Z-phenyl, -Z-Het, —CN, —CONR$^6$R$^7$, —NR$^6$R$^7$, -Z—$C_{1-3}$ alkyl, wherein said Het group represents a 5- or 6-membered aromatic heterocyclic ring or a 4- to 7-membered non-aromatic heterocyclic ring, wherein said phenyl or Het group of $R^1$ may be optionally substituted by one or more $R^8$ groups and wherein n represents an integer greater than 1, said $R^1$ groups represent no more than one -Z-phenyl or one -Z-Het group;
Z represents a bond or a linker selected from —O—, —CH$_2$—, —CH$_2$—O— or —O—CH$_2$—;
$R^6$ and $R^7$ independently represent hydrogen or $C_{1-6}$ alkyl or $R^6$ and $R^7$ together with the nitrogen atom to which they are attached join to form a 4- to 7-membered nitrogen containing non-aromatic heterocyclic ring;
$R^8$ represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —CN or -NR$^6$R$^7$;
m represents an integer selected from 0 to 2;
each $R^2$ independently represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —CN or —NR$^7$R$^8$;
$R^3$ represents hydrogen or $C_{1-6}$ alkyl;
$R^4$ represents hydrogen or $C_{1-6}$ alkyl;
p represents an integer from 0 to 3;
each $R^5$ independently represents $C_{1-3}$ alkyl or fluoro;
Y represents —CH$_2$— or —(CH$_2$)$_2$—;
q represents an integer selected from 0 to 2; and
$R^9$ represents $C_{1-3}$ alkyl.

2. A compound as defined in claim 1 or a pharmaceutically acceptable salt thereof, which is other than 7-methyl-2-[4-methyl-6-[4-(trifluoromethyl)-phenyl]pyrimidin-2-yl]-1,7-diazaspiro[4.4]nonan-6-one.

3. A compound as defined in claim 1 or a pharmaceutically acceptable salt thereof, wherein q represents 0.

4. A compound as defined in claim 1 or a pharmaceutically acceptable salt thereof, wherein Ring A represents a phenyl ring.

5. A compound as defined in claim 1 or a pharmaceutically acceptable salt thereof, wherein n represents an integer selected from 1 or 2.

6. A compound as defined in claim 1 or a pharmaceutically acceptable salt thereof, wherein $R^1$ independently represents halogen, halo$C_{1-6}$ alkyl, $C_{1-6}$ alkoxy or halo$C_{1-6}$ alkoxy.

7. A compound as defined in claim 1 or a pharmaceutically acceptable salt thereof, wherein m represents an integer selected from 0 or 1.

8. A compound as defined in claim 1 or a pharmaceutically acceptable salt thereof, wherein $R^2$ represents $C_{1-6}$ alkyl.

9. A compound as defined in claim 1 of a pharmaceutically acceptable salt thereof, wherein $R^3$ represents hydrogen.

10. A compound as defined in claim 1 or a pharmaceutically acceptable salt thereof, wherein $R^4$ represents hydrogen or methyl.

11. A compound as defined in claim 1 or a pharmaceutically acceptable salt thereof, wherein p represents 0.

12. A compound as defined in claim 1 or a pharmaceutically acceptable salt thereof, wherein Y represents CH$_2$.

13. A compound selected from a compound of
(2R,5S)-7-Methyl-2-[4-[4-(trifluoromethyl)phenyl]pyrimidin-2-yl]-1,7-diazaspiro[4.4]nonan-6-one hydrochloride;
(2S,5S)-7-Methyl-2-[4-[4-(trifluoromethyl)phenyl]pyrimidin-2-yl]-1,7-diazaspiro[4.4]nonan-6-one hydrochloride;

(2S,5R)-7-Methyl-2-[4-[4-(trifluoromethyl)phenyl]pyrimidin-2-yl]-1,7-diazaspiro[4.4]nonan-6-one hydrochloride;
(2R,5R)-7-methyl-2-[4-[4-(trifluoromethyl)-phenyl]-pyrimidin-2-yl]-1,7-diazaspiro[4.4]nonan-6-one hydrochloride;
(2S,5R)-7-Methyl-2-[4-methyl-6-[4-(trifluoromethyl) phenyl]pyrimidin-2-yl]-1,7-diazaspiro[4.4]nonan-6-one hydrochloride;
(2R,5R)-7-Methyl-2-[4-methyl-6-[4-(trifluoromethyl) phenyl]pyrimidin-2-yl]-1,7-diazaspiro[4.4]nonan-6-one hydrochloride;
(2S,5R)-2-[4-(5-Ethoxy-2-fluoro-phenyl)-6-methyl-pyrimidin-2-yl]-7-methyl-1,7-diazaspiro[4.4]nonan-6-one hydrochloride;
(2R,5R)-2-[4-(5-Ethoxy-2-fluoro-phenyl)-6-methyl-pyrimidin-2-yl]-7-methyl-1,7-diazaspiro[4.4]nonan-6-one hydrochloride;
(2R,5S)-2-[4-(5-Ethoxy-2-fluoro-phenyl)-6-methyl-pyrimidin-2-yl]-7-methyl-1,7-diazaspiro[4.4]nonan-6-one hydrochloride;
(2S,5S)-2-[4-(5-Ethoxy-2-fluoro-phenyl)-6-methyl-pyrimidin-2-yl]-7-methyl-1,7-diazaspiro[4.4]nonan-6-one hydrochloride;
(2R,6S)-2-[4-(5-Ethoxy-2-fluoro-phenyl)-6-methyl-pyrimidin-2-yl]-1,8-diazaspiro[4.5]decan-7 one hydrochloride;
(2S,6S)-2-[4-(5-Ethoxy-2-fluoro-phenyl)-6-methyl-pyrimidin-2-yl]-1,8-diazaspiro[4.5]decan-7-one hydrochloride;
(2R,5R)-2-[4-(5-Ethoxy-2-fluoro-phenyl)pyrimidin-2-yl]-7-methyl-1,7-diazaspiro[4.4]nonan-6-one hydrochloride;
(2S,5R)-2-[4-(5-Ethoxy-2-fluoro-phenyl)pyrimidin-2-yl]-7-methyl-1,7-diazaspiro[4.4]nonan-6-one hydrochloride;
(2S,5S)-2-[4-(5-Ethoxy-2-fluoro-phenyl)pyrimidin-2-yl]-7-methyl-1,7-diazaspiro[4.4]nonan-6-one hydrochloride;
(2R,5S)-2-[4-(5-Ethoxy-2-fluoro-phenyl)pyrimidin-2-yl]-7-methyl-1,7-diazaspiro[4.4]nonan-6-one hydrochloride;
(2R,5S)-7-Methyl-2-[4-[3-(trifluoromethoxy)phenyl]pyrimidin-2-yl]-1,7-diazaspiro[4.4]nonan-6 one hydrochloride;
(2S,5S)-7-Methyl-2-[4-[3-(trifluoromethoxy)phenyl]pyrimidin-2-yl]-1,7-diazaspiro[4.4]nonan-6 one hydrochloride;
(2S,5R)-7-Methyl-2-[4-[3-(trifluoromethoxy)phenyl]pyrimidin-2-yl]-1,7-diazaspiro[4.4]nonan-6 one hydrochloride;
(2R,5R)-7-Methyl-2-[4-[3-(trifluoromethoxy)phenyl]pyrimidin-2-yl]-1,7-diazaspiro[4.4]nonan-6 one hydrochloride;
(2S,5S)-7-Methyl-2-[4-methyl-6-[4-(trifluoromethyl)-phenyl]pyrimidin-2-yl]-1,7-diazaspiro[4.4]nonan-6-one hydrochloride;
(2R,5R)-2-[4-(4-Isopropoxyphenyl)pyrimidin-2-yl]-7-methyl-1,7-diazaspiro[4.4]nonan-6-one hydrochloride;
(2S,5R)-2-[4-(4-Isopropoxyphenyl)pyrimidin-2-yl]-7-methyl-1,7-diazaspiro[4.4]nonan-6-one hydrochloride;
(2S,5R)-2-[4-(4-Isopropoxyphenyl)pyrimidin-2-yl]-7-methyl-1,7-diazaspiro[4.4]nonan-6-one hydrochloride;
(2S,5S)-2-[4-(4-Isopropoxyphenyl)pyrimidin-2-yl]-7-methyl-1,7-diazaspiro[4.4]nonan-6-one hydrochloride;
(2R,5S)-7-Methyl-2-[4-methyl-6-[4-(trifluoromethoxy) phenyl]pyrimidin-2-yl]-1,7-diazaspiro[4.4]nonan-6-one hydrochloride;
(2S,5S)-7-Methyl-2-[4-methyl-6-[4-(trifluoromethoxy) phenyl]pyrimidin-2-yl]-1,7-diazaspiro[4.4]nonan-6-one hydrochloride;
(2S,5R)-7-Methyl-2-[4-methyl-6-[4-(trifluoromethoxy) phenyl]pyrimidin-2-yl]-1,7-diazaspiro[4.4]nonan-6-one hydrochloride;
(2R,5R)-7-Methyl-2-[4-methyl-6-[4-(trifluoromethoxy) phenyl]pyrimidin-2-yl]-1,7-diazaspiro[4.4]nonan-6-one hydrochloride;
(2S,5S)-2-[4-[2-Fluoro-5-(trifluoromethoxy)phenyl]-6-methyl-pyrimidin-2-yl]-7-methyl-1,7-diazaspiro[4.4]nonan-6-one hydrochloride;
(2R,5S)-2-[4-[2-Fluoro-5-(trifluoromethoxy)phenyl]-6-methyl-pyrimidin-2-yl]-7-methyl-1,7-diazaspiro[4.4]nonan-6-one hydrochloride;
(2R,5R)-2-[4-[2-Fluoro-5-(trifluoromethoxy)phenyl]-6-methyl-pyrimidin-2-yl]-7-methyl-1,7-diazaspiro[4.4]nonan-6-one hydrochloride;
(2S,5R)-2-[4-[2-Fluoro-5-(trifluoromethoxy)phenyl]-6-methyl-pyrimidin-2-yl]-7-methyl-1,7-diazaspiro[4.4]nonan-6-one hydrochloride;
(2R,5S)-7-Methyl-2-[4-methyl-6-[3-(trifluoromethoxy) phenyl]pyrimidin-2-yl]-1,7-diazaspiro[4.4]nonan-6-one hydrochloride;
(2S,5S)-7-Methyl-2-[4-methyl-6-[3-(trifluoromethoxy) phenyl]pyrimidin-2-yl]-1,7-diazaspiro[4.4]nonan-6-one hydrochloride;
(2R,6R)-2-[4-(5-Ethoxy-2-fluoro-phenyl)-6-methyl-pyrimidin-2-yl]-1,8-diazaspiro[4.5]decan-7-one hydrochloride;
(2S,6R)-2-[4-(5-Ethoxy-2-fluoro-phenyl)-6-methyl-pyrimidin-2-yl]-1,8-diazaspiro[4.5]decan-7-one hydrochloride;
(2R,5S)-2-[4-Methyl-6-[4-(trifluoromethyl)phenyl]pyrimidin-2-yl]-1,7-diazaspiro[4.4]nonan-6-one hydrochloride;
(2S,5R)-2-[4-Methyl-6-[4-(trifluoromethyl)phenyl]-pyrimidin-2-yl]-1,7-diazaspiro[4.4]nonan-6-one hydrochloride;
(2S,5S)-2-[4-Methyl-6-[4(trifluoromethyl)-phenyl]-pyrimidin-2-yl]-1,7-diazaspiro[4.4]nonan-6-one hydrochloride;
(2R,5R)-2-[4-Methyl-6-[4-(trifluoromethyl)phenyl]pyrimidin-2-yl]-1,7-diazaspiro[4.4]nonan-6-one hydrochloride;
(2R,5S)-8,8-Dimethyl-2-[4-methyl-6-[4-(trifluoromethyl)phenyl]pyrimidin-2-yl]-1,7-diazaspiro[4.4] nonan-6-one hydrochloride;
(2S,5S)-8,8-Dimethyl-2-[4-methyl-6-[4-(trifluoromethyl) phenyl]pyrimidin-2-yl]-1,7-diazaspiro[4.4]nonan-6-one hydrochloride;
(2S,5R)-8,8-Dimethyl-2-[4-methyl-6-[4-(trifluoromethyl)phenyl]pyrimidin-2-yl]-1,7-diazaspiro[4.4] nonan-6-one hydrochloride; and
(2R,5R)-8,8-Dimethyl-2-[4-methyl-6-[4-(trifluoromethyl)phenyl]pyrimidin-2-yl]-1,7-diazaspiro[4.4] nonan-6-one hydrochloride
or free base preparation thereof.

14. A pharmaceutical composition comprising a compound of formula (I) as defined in claim 1, or a pharmaceutically acceptable salt thereof with one or more pharmaceutically acceptable carrier(s), diluents(s) and/or excipient(s).

15. A process for preparing a compound of formula (I) as defined in claim 1, which comprises:
(a) forming a compound of formula (I) wherein p represents 0 and $R^3$ represents hydrogen by performing a ring closure reaction of a compound of formula (II) followed by Reduction of the resulting imine (IIA);

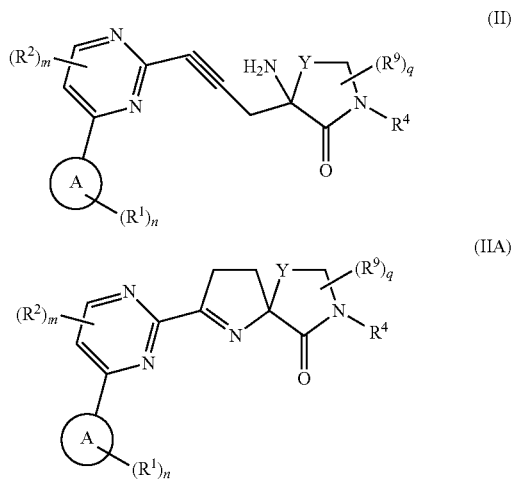

or a protected derivative thereof, wherein A, $R^1$, $R^2$, $R^4$, $R^9$, n m, q and Y are as defined in claim 1;
(b) deprotection of a protected derivative of a compound of formula (I);
(c) interconversion of a compound of formula (I) or protected derivative thereof to a further compound of formula (I) or protected derivative thereof; and
(d) optional formation of a pharmaceutically acceptable salt of a compound of formula (I).

16. A method for treating neuropathic pain, comprising: administering to the patient an effective amount of the compound of claim 1 or a pharmaceutically acceptable salt thereof.

17. A compound selected from a compound of
(2R,5S)-7-Methyl-2-[4-[4-(trifluoromethyl)phenyl]pyrimidin-2-yl]-1,7-diazaspiro[4.4]nonan-6-one hydrochloride;
(2S,5S)-7-Methyl-2-[4-[4-(trifluoromethyl)phenyl]pyrimidin-2-yl]-1,7-diazaspiro[4.4]nonan-6-one hydrochloride;
(2S,5R)-7-Methyl-2-[4-[4-(trifluoromethyl)phenyl]pyrimidin-2-yl]-1,7-diazaspiro[4.4]nonan-6-one hydrochloride;
(2R,5R)-7-Methyl-2-[4-[4-(trifluoromethyl)-phenyl]-pyrimidin-2-yl]-1,7-diazaspiro[4.4]nonan-6-one hydrochloride;
(2S,5R)-7-Methyl-2-[4-methyl-6-[4-(trifluoromethyl)phenyl]pyrimidin-2-yl]-1,7-diazaspiro[4.4]nonan-6-one hydrochloride;
(2R,5R)-7-Methyl-2-[4-methyl-6-[4-(trifluoromethyl)phenyl]pyrimidin-2-yl]-1,7-diazaspiro[4.4]nonan-6-one hydrochloride;
(2S,5R)-2-[4-(5-Ethoxy-2-fluoro-phenyl)-6-methyl-pyrimidin-2-yl]-7-methyl-1,7-diazaspiro[4.4]nonan-6-one hydrochloride;
(2R,5R)-2-[4-(5-Ethoxy-2-fluoro-phenyl)-6-methyl-pyrimidin-2-yl]-7-methyl-1,7-diazaspiro[4.4]nonan-6-one hydrochloride;
(2R,5S)-2-[4-(5-Ethoxy-2-fluoro-phenyl)-6-methyl-pyrimidin-2-yl]-7-methyl-1,7-diazaspiro[4.4]nonan-6-one hydrochloride;
(2S,5S)-2-[4-(5-Ethoxy-2-fluoro-phenyl)-6-methyl-pyrimidin-2-yl]-7-methyl-1,7-diazaspiro[4.4]nonan-6-one hydrochloride;
(2R,6S)-2-[4-(5-Ethoxy-2-fluoro-phenyl)-6-methyl-pyrimidin-2-yl]-1,8-diazaspiro[4.5]decan-7 one hydrochloride;
(2S,6S)-2-[4-(5-Ethoxy-2-fluoro-phenyl)-6-methyl-pyrimidin-2-yl]-1,8-diazaspiro[4.5]decan-7-one hydrochloride;
(2R,5R)-2-[4-(5-Ethoxy-2-fluoro-phenyl)pyrimidin-2-yl]-7-methyl-1,7-diazaspiro[4.4]nonan-6-one hydrochloride;
(2S,5R)-2-[4-(5-Ethoxy-2-fluoro-phenyl)pyrimidin-2-yl]-7-methyl-1,7-diazaspiro[4.4]nonan-6-one hydrochloride;
(2S,5S)-2-[4-(5-Ethoxy-2-fluoro-phenyl)pyrimidin-2-yl]-7-methyl-1,7-diazaspiro[4.4]nonan-6-one hydrochloride;
(2R,5S)-2-[4-(5-Ethoxy-2-fluoro-phenyl)pyrimidin-2-yl]-7-methyl-1,7-diazaspiro[4.4]nonan-6-one hydrochloride;
(2R,5S)-7-Methyl-2-[4-[3-(trifluoromethoxy)phenyl]pyrimidin-2-yl]-1,7-diazaspiro[4.4]nonan-6-one hydrochloride;
(2S,5S)-7-Methyl-2-[4-[3-(trifluoromethoxy)phenyl]pyrimidin-2-yl]-1,7-diazaspiro[4.4]nonan-6-one hydrochloride;
(2S,5R)-7-Methyl-2-[4-[3-(trifluoromethoxy)phenyl]pyrimidin-2-yl]-1,7-diazaspiro[4.4]nonan-6-one hydrochloride;
(2R,5R)-7-Methyl-2-[4-[3-(trifluoromethoxy)phenyl]pyrimidin-2-yl]-1,7-diazaspiro[4.4]nonan-6-one hydrochloride; and
(2S,5S)-7-Methyl-2-[4-methyl-6-[4-(trifluoromethyl)-phenyl]pyrimidin-2-yl]-1,7-diazaspiro[4.4]nonan-6-one hydrochloride.

18. A pharmaceutical composition comprising a compound of claim 13 with one or more pharmaceutically acceptable carrier(s), diluents(s) and/or excipient(s).

19. A pharmaceutical composition comprising a compound of claim 17 with one or more pharmaceutically acceptable carrier(s), diluents(s) and/or excipient(s).

20. A method for treating neuropathic pain, comprising: administering to the patient an effective amount of the compound of claim 13.

21. A method for treating neuropathic pain, comprising: administering to the patient an effective amount of the compound of claim 17.

22. A compound selected from a compound of
(2R,5S)-7-Methyl-2-[4-[4-(trifluoromethyl)phenyl]pyrimidin-2-yl]-1,7-diazaspiro[4.4]nonan-6-one;
(2S,5S)-7-Methyl-2-[4-[4-(trifluoromethyl)phenyl] pyrimidin-2-yl]-1,7-diazaspiro[4.4]nonan-6-one;
(2S,5R)-7-Methyl-2-[4-[4-(trifluoromethyl)phenyl]pyrimidin-2-yl]-1 ,7-diazaspiro[4.4]nonan-6-one;
(2R,5R)-7-Methyl-2-[4[4-(trifluoromethyl)-phenyl]-pyrimidin-2-yl]-1,7-diazaspiro [4.4]nonan -6- one;
(2S,5R)-7-Methyl-2-[4-methyl-6-[4-(trifluoromethyl)phenyl]pyrimidin-2-yl]-1,7-diazaspiro[4.4]nonan-6-one;
(2R,5R)-7-Methyl-2-[4-methyl-6-[4-(trifluoromethyl)phenyl]pyrimidin-2-yl]-1,7-diazaspiro[4.4]nonan-6-one;

(2S,5R)-2-[4-(5-Ethoxy-2-fluoro-phenyl)-6-methyl-pyrimidin-2-yl]-7-methyl-1,7-diazaspiro [4.4]nonan-6-one;
(2R,5R)-2-[4-(5-Ethoxy-2-fluoro-phenyl)-6-methyl-pyrimidin-2-yl]-7-methyl-1,7-diazaspiro [4.4]nonan-6-one;
2R,5S)-2-[4-(5-Ethoxy-2-fluoro-phenyl)-6-methyl-pyrimidin-2-yl]-7-methyl-1,7-diazaspiro[4.4]nonan-6-one;
(2S,5S)-2-[4-(5-Ethoxy-2-fluoro-phenyl)-6-methyl-pyrimidin-2-yl]-7-methyl- 1,7-diazaspiro[4.4]nonan-6-one;
(2R,6S)-2-[4-(5-Ethoxy-2-fluoro-phenyl)-6-methyl-pyrimidin-2-yl]-1,8-diazaspiro[4.5]decan-7 one;
(2S,6S)-2-[4-(5-Ethoxy-2-fluoro-phenyl)-6-methyl-pyrimidin-2-yl]-1 ,8-diazaspiro[4.5]decan-7-one;
(2R,5R)-2-[4-(5-Ethoxy-2-fluoro-phenyl)pyrimidin-2-yl]-7-methyl-1,7-diazaspiro[4.4]nonan-6-one;
(2S,5R)-2-[4-(5-Ethoxy-2-fluoro-phenyl)pyrimidin-2-yl]-7-methyl-1,7-diazaspiro [4.4]nonan-6-one;
(2S,5S)-2-[4-(5-Ethoxy-2-fluoro-phenyl)pyrimidin-2-yl]-7-methyl-1,7-diazaspiro [4.4]nonan-6-one;
(2R,5S)-2-[4-(5-Ethoxy-2-fluoro-phenyl)pyrimidin-2-yl]-7-methyl-1,7-diazaspiro [4. 4]nonan-6-one;
(2R,5S)-7-Methyl-2- [4- [3-(trifluoromethoxy)phenyl]pyrimidin-2-yl]-1,7-diazaspiro[4.4]nonan-6 one;
(2S,5S)-7-Methyl-2- [4- [3-(trifluoromethoxy)phenyl]pyrimidin-2-yl]-1,7-diazaspiro[4.4]nonan-6 one;
(2S,5R)-7-Methyl-2- [4-[3 -(trifluoromethoxy)phenyl]pyrimidin-2-yl-1,7-diazaspiro[4.4]nonan-6 one;
(2R,5R)-7-Methyl-2-[4-[3-(trifluoromethoxy)phenyl]pyrimidin-2-yl]-1,7-diazaspiro[4.4]nonan-6 one;
(2S,5S)-7-Methyl-2-[4-methyl-6-[4-(trifluoromethyl)-phenyl]pyrimidin-2-yl]-1,7-diazaspiro[4.4]nonan-6-one;
(2R,5R)-2-[4-(4-Isopropoxyphenyl)pyrimidin-2-yl]-7-methyl-1,7-diazaspiro[4.4]nonan-6-one;
(2S,5R)-2-[4-(4-Isopropoxyphenyl)pyrimidin-2-yl]-7-methyl-1,7-diazaspiro[4.4]nonan-6-one;
(2S,5R)-2-[4-(4-Isopropoxyphenyl)pyrimidin-2-yl]-7-methyl-1,7-diazaspiro[4.4]nonan-6-one;
(2S,5S)-2-[4-(4-Isopropoxyphenyl)pyrimidin-2-yl]-7-methyl-1,7-diazaspiro[4.4]nonan-6-one;
(2R,5S)-7-Methyl-2-[4-methyl-6-[4-(trifluoromethoxy)phenyl]pyrimidin-2-yl]-1,7-diazaspiro[4.4]nonan-6-one;
(2S,5S)-7-Methyl-2-[4-methyl-6-[4-(trifluoromethoxy)phenyl]pyrimidin-2-yl]-1,7-diazaspiro[4.4]nonan-6-one;
(2S,5R)-7-Methyl-2-[4-methyl-6-[4-(trifluoromethoxy)phenyl]pyrimidin-2-yl]- 1,7-diazaspiro[4.4]nonan-6-one;
(2R,5R)-7-Methyl-2-[4-methyl-6-[4-(trifluoromethoxy)phenyl]pyrimidin-2-yl]-1,7-diazaspiro[4.4]nonan-6-one;
(2S,5S)-2-[4-[2-Fluoro-5-(trifluoromethoxy)phenyl]-6-methyl-pyrimidin-2-yl]-7-methyl-1,7-diazaspiro [4.4] nonan-6-one;
(2R,5S)-2-[4-[2-Fluoro-5-(trifluoromethoxy)phenyl]-6-methyl-pyrimidin-2-yl]-7-methyl-1,7-diazaspiro[4.4] nonan-6-one;
(2R,5R)-2-[4-[2-Fluoro-5-(trifluoromethoxy)phenyl]-6-methyl-pyrimidin-2-yl]-7-methyl-1,7-diazaspiro[4.4] nonan-6-one;
(2S,5R)-2-[4-[2-Fluoro-5-(trifluoromethoxy)phenyl]-6-methyl-pyrimidin-2-yl]-7-methyl-1,7-diazaspiro [4.4] nonan-6-one;
(2R,5S)-7-Methyl-2-[4-methyl-6-[3-(trifluoromethoxy)phenyl]pyrimidin-2-yl]- 1,7-diazaspiro [4.4]nonan-6-one;
(2S,5S)-7-Methyl-2-[4-methyl-6-[3-(trifluoromethoxy)phenyl]pyrimidin-2-yl]-1,7-diazaspiro[4.4]nonan-6-one;
(2R,6R)-2-[4-(5-Ethoxy-2-fluoro-phenyl)-6-methyl-pyrimidin-2-yl]-1,8-diazaspiro[4.5]decan-7-one;
(2S,6R)-2-[4-(5-Ethoxy-2-fluoro-phenyl)-6-methyl-pyrimidin-2-yl]-1,8-diazaspiro[4.5]decan-7-one;
(2R,5S)-2-[4-Methyl-6-[4-(trifluoromethyl)phenyl]pyrimidin-2-yl]-1,7-diazaspiro[4.4]nonan-6-one;
one;
(2S,5R)-2-[4-Methyl-6-[4-(trifluoromethyl)phenyl]-pyrimidin-2-yl]-1,7-diazaspiro[4.4]nonan-6-one;
(2S,5S)-2-[4-Methyl-6-[4(trifluoromethyl)-phenyl]-pyrimidin-2-yl]-1,7-diazaspiro[4.4]nonan-6-one;
(2R,5R)-2-[4-Methyl-6-[4-(trifluoromethyl)phenyl]pyrimidin-2-yl]-1,7-diazaspiro [4.4]nonan-6-one;
(2R,5S)-8,8-Dimethyl-2-[4-methyl-6-[4-(trifluoromethyl)phenyl]pyrimidin-2-yl]-1,7-diazaspiro[4.4] nonan-6-one;
(2S,5S)-8,8-Dimethyl-2-[4-methyl-6-[4-(trifluoromethyl)phenyl]pyrimidin-2-yl]-1,7-diazaspiro[4.4]nonan-6-one;
(2S,5R)-8,8-Dimethyl-2-[4-methyl-6-[4-(trifluoromethyl)phenyl]pyrimidin-2-yl]-1,7-diazaspiro[4.4] nonan-6-one; and
(2R,5R)-8,8-Dimethyl-2-[4-methyl-6-[4-(trifluoromethyl)phenyl]pyrimidin-2-yl]-1,7-diazaspiro[4.4] nonan-6-one or a pharmaceutically acceptable salt thereof.

23. A pharmaceutical composition comprising a compound of claim 22 or a pharmaceutically acceptable salt thereof with one or more pharmaceutically acceptable carrier (s), diluents(s) and/or excipient(s).

24. A method for treating neuropathic pain, comprising: administering to the patient an effective amount of the compound of claim 22 or a pharmaceutically acceptable salt thereof.

* * * * *

UNITED STATES PATENT AND TRADEMARK OFFICE
CERTIFICATE OF CORRECTION

PATENT NO. : 9,309,254 B2  
APPLICATION NO. : 14/403480  
DATED : April 12, 2016  
INVENTOR(S) : Gerard M. P. Giblin et al.

Page 1 of 1

It is certified that error appears in the above-identified patent and that said Letters Patent is hereby corrected as shown below:

In the claims,

• In claim 9, column 88, line 52, please replace:

"...A compound as defined in claim 1 of a pharmaceutically..."

with:

--A compound as defined in claim 1 or a pharmaceutically...--

• In claim 22, column 93, line 27, please replace:

""...rimidin-2-yl-1, 7-diazaspiro[4.4]nonan-6 one;..."

with:

--...rimidin-2-yl]-1, 7-diazaspiro[4.4]nonan-6 one;...--

Signed and Sealed this  
Twenty-sixth Day of July, 2016

Michelle K. Lee  
*Director of the United States Patent and Trademark Office*